(12) United States Patent
Larsen et al.

(10) Patent No.: US 8,642,727 B2
(45) Date of Patent: Feb. 4, 2014

(54) SELECTIVE GLUCAGON-LIKE-PEPTIDE-2 (GLP-2) ANALOGUES

(75) Inventors: Bjarne Due Larsen, Roskilde (DK); Yvette Miata Petersen, Bagsvaerd (DK)

(73) Assignee: Zealand Pharma A/S, Glostrup (DK)

( * ) Notice: Subject to any disclaimer, the term of this patent is extended or adjusted under 35 U.S.C. 154(b) by 837 days.

(21) Appl. No.: 12/514,042

(22) PCT Filed: Nov. 8, 2007

(86) PCT No.: PCT/GB2007/004273
§ 371 (c)(1),
(2), (4) Date: Nov. 17, 2009

(87) PCT Pub. No.: WO2008/056155
PCT Pub. Date: May 15, 2008

(65) Prior Publication Data
US 2012/0004392 A1   Jan. 5, 2012

Related U.S. Application Data

(60) Provisional application No. 60/859,313, filed on Nov. 15, 2006.

(30) Foreign Application Priority Data

Nov. 8, 2006 (DK) .................. 2006 01456

(51) Int. Cl.
*A61K 38/26* (2006.01)
*C07K 14/605* (2006.01)

(52) U.S. Cl.
USPC .......................................... 530/324; 530/308

(58) Field of Classification Search
None
See application file for complete search history.

(56) References Cited

U.S. PATENT DOCUMENTS

| | | | |
|---|---|---|---|
| 5,432,156 A | 7/1995 | Matsuno et al. | |
| 5,789,379 A | 8/1998 | Drucker et al. | |
| 5,834,428 A | 11/1998 | Drucker | |
| 5,912,229 A | 6/1999 | Thim et al. | |
| 5,952,301 A | 9/1999 | Drucker | |
| 5,990,077 A | 11/1999 | Drucker | |
| 5,994,500 A | 11/1999 | Drucker et al. | |
| 6,051,557 A | 4/2000 | Drucker | |
| 6,184,201 B1 | 2/2001 | Drucker et al. | |
| 6,184,208 B1 | 2/2001 | Deigin et al. | |
| 6,297,214 B1 | 10/2001 | Drucker | |
| 6,489,295 B1 | 12/2002 | Drucker et al. | |
| 6,586,399 B1 | 7/2003 | Drucker | |
| 6,770,620 B2 | 8/2004 | Henriksen | |
| 7,049,284 B2 | 5/2006 | Drucker | |
| 7,176,182 B2 | 2/2007 | Drucker | |
| 7,186,683 B2 | 3/2007 | Henriksen et al. | |
| 7,371,721 B2 | 5/2008 | Henriksen et al. | |
| 7,411,039 B2 | 8/2008 | Thim et al. | |
| 7,563,770 B2 | 7/2009 | Larsen et al. | |
| 7,745,403 B2 | 6/2010 | Larsen et al. | |
| 8,163,696 B2 | 4/2012 | Larsen et al. | |
| 8,263,552 B2 | 9/2012 | Larsen et al. | |
| 2002/0025933 A1 | 2/2002 | Knudsen et al. | |
| 2003/0040478 A1 | 2/2003 | Drucker et al. | |
| 2003/0109449 A1 | 6/2003 | Drucker et al. | |
| 2003/0158101 A1 | 8/2003 | Drucker | |
| 2003/0162703 A1 | 8/2003 | Drucker et al. | |
| 2003/0207809 A1 | 11/2003 | Drucker | |
| 2004/0052862 A1 | 3/2004 | Henriksen et al. | |
| 2004/0122210 A1 | 6/2004 | Thim et al. | |
| 2004/0127418 A1 | 7/2004 | Knudsen et al. | |
| 2004/0198642 A1 | 10/2004 | Drucker et al. | |
| 2005/0282749 A1 | 12/2005 | Henriksen et al. | |
| 2006/0105954 A1 | 5/2006 | Drucker | |
| 2007/0117752 A1 | 5/2007 | Larsen et al. | |
| 2009/0082309 A1 | 3/2009 | Bachovchin et al. | |
| 2012/0289466 A1 | 11/2012 | Larsen et al. | |

FOREIGN PATENT DOCUMENTS

| | | |
|---|---|---|
| EP | 1231219 A1 | 8/2002 |
| WO | WO-96/32414 A1 | 10/1996 |
| WO | WO-97/39031 A1 | 10/1997 |
| WO | WO-98/03547 A1 | 1/1998 |
| WO | WO-98/11125 A1 | 3/1998 |
| WO | WO-99/46283 A1 | 9/1999 |
| WO | WO-01/04156 A1 | 1/2001 |
| WO | WO-01/41779 A2 | 6/2001 |
| WO | WO-02/066511 A2 | 8/2002 |
| WO | WO-02/098348 A2 | 12/2002 |
| WO | WO-2005/027978 A2 | 3/2005 |
| WO | WO-2006/117565 A2 | 11/2006 |

OTHER PUBLICATIONS

Bowie et al., 1990, Science 247: 1306-1310.*
Wells, 1990, Biochemistry 29:8509-8517.*

(Continued)

*Primary Examiner* — Gyan Chandra
(74) *Attorney, Agent, or Firm* — Clark & Elbing LLP; Kristina Bieker-Brady

(57) ABSTRACT

GLP-2 analogues are disclosed which comprise one of more substitutions as compared to h[Gly2]GLP-2 and which may have the property of an increased small intestine/colon and stomach/colon selectivity. More particularly, preferred GLP-2 analogues disclosed herein comprise substitutions at one or more of positions 11, 16, 20, 24 and/or 28 of the wild-type GLP-2 sequence, optionally in combination with further substitutions at position 2 and one or more of positions 3, 5, 7, and 10, and/or a deletion of one or more of amino acids 31 to 33 and/or the addition of a N-terminal or C-terminal stabilizing peptide sequence. The analogues are particularly useful for the prophylaxis or treatment of stomach and bowel-related disorders and for ameliorating side effects of chemotherapy.

6 Claims, 8 Drawing Sheets

(56) References Cited

OTHER PUBLICATIONS

Alison et al., "The Role of Growth Factors in Gastrointestinal Cell Proliferation," *Cell Biol. Int.* 18(1):1-10, 1994.
Baldwin et al., "Gut Hormones, Growth and Malignancy," *Bailliére's Clin. Endocrinol. Metab.* 8(1):185-214, 1994.
Bamba et al., "Enteroglucagon. A Putative Humoral Factor Including Pancreatic Hyperplasia After Proximal Small Bowel Resection," *Dig. Dis. Sci.* 39(7):1532-1536, 1994.
Barragán et al., "Changes in Arterial Blood Pressure and Heart Rate Induced by Glucagon-Like Peptide-1-(7-36) Amide in Rats," *Am. J. Physiol.* 266:E459-E466, 1994.
Benjamin et al., "Glucagon-Like Peptide-2 Enhances Intestinal Epithelial Barrier Function of Both Transcellular and Paracellular Pathways in the Mouse," *Gut* 47:112-119, 2000.
Bloom, S.R., "Gut Hormones in Adaptation," *Gut* 28(Suppl):31-35, 1987.
Booth et al., "Teduglutide ([Gly2]GLP-2) Protects Small Intestinal Stem Cells from Radiation Damage," *Cell Prolif.* 37:385-400, 2004.
Boushey et al., "Glucagon-Like Peptide (GLP)-2 Reduces Chemotherapy-Associated Mortality and Enhances Cell Survival in Cells Expressing a Transfected GLP-2 Receptor," *Cancer Res.* 61:687-693, 2001.
Brubaker et al., "Alterations in Proglucagon Processing and Inhibition of Proglucagon Gene Expression in Transgenic Mice Which Contain a Chimeric Proglucagon-SV40 T Antigen Gene," *J. Biol. Chem.* 267(29):20728-20733, 1992.
Cheeseman, "Upregulation of SGLT-1 Transport Activity in Rat Jejunum Induced by GLP-2 Infusion In Vivo," *Am. J. Physiol.* 273:R1965-R1971, 1997.
Code, Charles F., "The Digestive System," *Annu. Rev. Physiol.* 15:107-138, 1953.
Creson et al., "Powdered Duodenal Extract in the Treatment of Peptic Ulcer," *Am. J. Gastroenterol.* 33:359-365, 1960.
DaCambra et al., "Structural Determinants for Activity of Glucagon-Like Peptide-2," *Biochemistry* 39:8888-8894, 2000.
Drucker, "Glucagon-Like Peptide 2," *J Clin. Endocrinol. Metab.* 86(4):1759-1764, 2001.
Drucker et al., "Induction of Intestinal Epithelial Proliferation by Glucagon-Like Peptide 2," *Proc. Nat. Acad. Sci. U.S.A.* 93:7911-7916, 1996.
Drucker, "Minireview: The Glucagon-Like Peptides," *Endocrinology* 142(2):521-527, 2001.
Drucker et al., "Regulation of the Biological Activity of Glucagon-like Peptide 2 In Vivo by Dipeptidyl Peptidase IV" *Nature Biotechnology* 15:673-677, 1997.
Feinberg et al., "Period and Amplitude Analysis of 0.5-3 c/sec Activity in NREM Sleep of Young Adults," *Electroencephalogr. Clin. Neurophysiol.* 44(2):202-213, 1978.
Ferrone et al., "Teduglutide for the Treatment of Short Bowel Syndrome," *Ann. Pharmacother.* 40:1105-1109, 2006.
Gadermann et al., "Zur Behandlung von Gastroduodenalen Ulcerationen und Entzündungen mit dem Gewebsextrakt Robadin," *Med. Klin.* 54(16):774-778, 1959. (In German).
Gadermann et al., "Treatment of gastroduodenal ulcerations and inflammations with the tissue extract robadin," *Med. Clin.* 54(16):774-778, 1959. (English translation).
Gibson et al., "Irinotecan Causes Severe Small Intestinal Damage, as well as Colonic Damage, in the Rat with Implanted Breast Cancer," *J. Gastroenterol. Hepatol.* 18(9):1095-1100, 2003.
Gibson et al., "Relative Roles of Spatial and Intensive Cues in the Discrimination of Spatial Tactile Stimuli," *Percept. Physchophys.* 64:1095-1107, 2002.
Glass et al., "Studies on Robuden, Extract from Stomach and Duodenum: Its Effects Upon Gastric Secretion and Clinical Course of Peptic Ulcer," *Am. J. Dig. Dis.* 4(12):988-1013, 1959.
Gregor et al., "The Role of Gut-Glucagon-Like Immunoreactants in the Control of Gastrointestinal Epithelial Cell Renewal," *Digestion* 46(Suppl 2):59-65, 1990.
Grey et al., "A Growth-Stimulating Activity Derived from the Proximal Small Intestine is Associated with an Adaptive Response," *Can. J. Physiol. Pharmacol.* 68(5):646-649, 1990.
Grey et al., "Detection of Growth-Stimulating Activity in the Proximal Small Intestine During Weaning in the Suckling Rat," *Biol. Neonate* 59(1):37-45, 1991.
Grey et al., "Evidence for a Growth-Stimulating Fraction in the Rat Proximal Intestine After Small Bowel Resection," *Gastroenterology* 89(6):1305-1312, 1985.
Guan et al., "GLP-2-Mediated Up-Regulation of Intestinal Blood Flow and Glucose Uptake Is Nitric Oxide-Dependent in TPN-Fed Piglets," *Gastroenterology* 125:136-147, 2003.
Irwin et al., "Trout and Chicken Proglucagon: Alternative Splicing Generates mRNA Transcripts Encoding Glucagon-Like Peptide 2," *Mol. Endocrinol.* 9(3):267-277, 1995.
Jenkins et al., "Mechanisms of Small Intestinal Adaptation," *Dig. Dis.* 12(1):15-27, 1994.
Jeppesen, "The Use of Hormonal Growth Factors in the Treatment of Patients with Short-Bowel Syndrome," *Drugs* 66:581-589, 2006.
Keefe et al., "Chemotherapy for Cancer Causes Apoptosis that Precedes Hypoplasia in Crypts of the Small Intestine in Humans," *Gut* 47:632-637, 2000.
Kieffer et al., "The Glucagon-Like Peptides," *Endocr. Rev.* 20(6):876-913, 1999.
Lentze, M.J., "Intestinal Adaptation in Short-Bowel Syndrome," *Eur. J. Pediatr.* 148(4):294-299, 1989.
Lopez et al., "Mammalian Pancreatic Preproglucagon Contains Three Glucagon-Related Peptides," *Proc. Natl. Acad. Sci. U.S.A.* 80(18):5485-5489, 1983.
Meier et al., "Glucagon-Like Peptide 2 Stimulates Glucagon Secretion, Enhances Lipid Adsorption, and Inhibits Gastric Acid Secretion in Humans," *Gastroenterology* 130:44-54, 2006.
Mentlein et al., "Dipeptidyl-Peptidase IV Hydrolyses Gastric Inhibitory Polypeptide, Glucagon-Like Peptide-1(7-36)Amide, Peptide Histidine Methionine and is Responsible for Their Degradation in Human Serum," *Eur. J. Biochem.* 214(3):829-835, 1993.
Miazza et al., "Hyperenteroglucagonaemia and Small Intestinal Mucosal Growth After Colonic Perfusion of Glucose in Rats," *Gut* 26(5):518-524, 1985.
Neumann, H. W., "Erfahrungen mit Präparaten. Rüekblick auf 12 Jahre Robudon-Behandlaug Peptischer Ulcera," *Schweiz. Med. Wochenschr.* 87(32):1049-1051, 1957 (In German).
Neumann, H. W., "Experiences with medications: A review of 12 years of peptic ulcer treatment with Robuden," *Schweiz. Med. Wochenschr.* 87(32):1049-1051, 1957 (English translation).
Notkin et al., "Gastroduodenal Tissue Extracts in the Treatment of Peptic Ulcer with Special Reference to the Effectiveness of Robuden," *Am. J. Dig. Dis.* 21(9):251-261, 1954.
Oben et al., "Effect of the Entero-Pancreatic Hormones, Gastric Inhibitory Polypeptide and Glucagon-Like Polypeptide-1(7-36) Amide, on Fatty Acid Synthesis in Explants of Rat Adipose Tissue," *J. Endocrinol.* 130(2):267-272, 1991.
Ørskov et al., "Glucagon-Like Peptides GLP-1 and GLP-2, Predicted Products of the Glucagon Gene, are Secreted Separately from Pig Small Intestine but Not Pancreas," *Endocrinology* 119(4):1467-1475, 1986.
Pouliot et al., "Follow-Up Studies on Peptic Ulcer Patients Treated with Robuden," *Can. Med. Assoc. J.* 82:524-528, 1960.
Richter et al., "GLP-1 Stimulates Secretion of Macromolecules from Airways and Relaxes Pulmonary Artery," *Am. J. Physiol.* 265:L374-L381, 1993.
Ruiz-Grande et al., "Lipolytic Action of Glucagon-Like Peptides in Isolated Rat Adipocytes," *Peptides* 13(1):13-16, 1992.
Sasaki et al., "Enteroglucagon, but not CCK, Plays an Important Role in Pancreatic Hyperplasia After Proximal Small Bowel Resection," *J. Gastroenterol. Hepatol.* 9(6):576-581, 1994.
Sinclair et al., "Proglucagon-Derived Peptides: Mechanisms of Action and Therapeutic Potential," *Physiology* 20:357-365, 2005.
Singh et al. "Use of $^{125}$I-[Y$^{39}$]Exendin-4 to Characterize Exendin Receptors on Dispersed Pancreatic Acini and Gastric Chief Cells from Guinea Pig," *Regul. Pept.* 53(1):47-59, 1994.

(56) References Cited

OTHER PUBLICATIONS

Suda, K., "The Organ Distribution and Molecular Forms of Glucagon-Related Peptides," *Yamagata Med. J.* 6(2):149-161, 1988 (In Japanese).

Suda, K., "The Organ Distribution and Molecular Forms of Glucagon-Related Peptides," *Yamagata Med. J.* 6(2):149-161, 1988 (English translation).

Tamaki et al., "Apoptosis in Normal Tissues by Anti-Cancer Drugs," *J. Int. Med. Res.* 31:6-16, 2003.

Tavares et al., "Enzymatic- and Renal-Dependent Catabolism of the Intestinotropic Hormone Glucagon-Like Peptide-2 in Rats," *Am. J. Physiol. Endocrinol. Metab.* 278:E134-E139, 2000.

Thulesen et al., "Glucagon-Like Peptide 2 (GLP-2) Accelerates the Growth of Colonic Neoplasms in Mice," *Gut* 53:1145-1150, 2004.

Valverde et al., "Presence and Characterization of Glucagon-Like Peptide-1(7-36) Amide Receptors in Solubilized Membranes of Rat Adipose Tissue," *Endocrinology* 132(1):75-79, 1993.

Wøjdemann et al., "Inhibition of Sham Feeding-Stimulated Human Gastric Acid Secretion by Glucagon-Like Peptide-2," *J. Clin. Endocrinol. Metab.* 84:2513-2517, 1999.

Yusta et al., "Enteroendocrine Localization of GLP-2 Receptor Expression in Humans and Rodents," *Gastroenterology* 119:744-755, 2000.

International Search Report from PCT/GB2006/001633, completed Sep. 19, 2006, mailed Oct. 24, 2006.

International Preliminary Report on Patentability from PCT/GB2006/001633, issued Nov. 6, 2007.

Written Opinion of the International Searching Authority from PCT/GB2006/001633, completed Sep. 19, 2006, mailed Oct. 24, 2006.

International Search Report from PCT/GB2007/004273, completed Apr. 8, 2008, mailed Apr. 14, 2008.

International Preliminary Report on Patentability from PCT/GB2007/004273, issued May 12, 2009.

Written Opinion of the International Searching Authority from PCT/GB2007/004273, competed Apr. 8, 2008, mailed Apr. 14, 2008.

\* cited by examiner

SEQUENCE LISTING

<160> NUMBER OF SEQ ID NOS: 130

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

```
<210> SEQ ID NO 2
<211> LENGTH: 53
<212> TYPE: PRT
<213> ORGANISM: Artificial sequence
<220> FEATURE:
<223> OTHER INFORMATION: Synthetic sequence: General Formula I of Claim
      1 of PCT/GB2007/004273
<220> FEATURE:
<221> NAME/KEY: VARIANT
<222> LOCATION: (1)..(10)
<223> OTHER INFORMATION: May be present or absent. If present,
      represents a peptide sequence of 1 - 10 amino acids wherein each
      Xaa may be absent or is selected from the group consisting of Ala,
      Leu, Ser, Thr, Tyr, Asn, Gln, Asp, Glu, Lys, Arg, His, Met, and
      Orn
<220> FEATURE:
<221> NAME/KEY: VARIANT
<222> LOCATION: (12)..(12)
<223> OTHER INFORMATION: Xaa is Gly, Ala or Sar
<220> FEATURE:
<221> NAME/KEY: VARIANT
<222> LOCATION: (13)..(13)
<223> OTHER INFORMATION: Xaa is Glu or Asp
<220> FEATURE:
<221> NAME/KEY: VARIANT
<222> LOCATION: (15)..(15)
<223> OTHER INFORMATION: Xaa is Ser or Thr
<220> FEATURE:
<221> NAME/KEY: VARIANT
<222> LOCATION: (16)..(16)
<223> OTHER INFORMATION: Xaa is Phe or Pro or a conservative
      substitution
<220> FEATURE:
<221> NAME/KEY: VARIANT
<222> LOCATION: (17)..(17)
<223> OTHER INFORMATION: Xaa is Ser or Thr
<220> FEATURE:
<221> NAME/KEY: VARIANT
<222> LOCATION: (18)..(18)
<223> OTHER INFORMATION: Xaa is Asp or Ser or a conservative
      substitution
<220> FEATURE:
<221> NAME/KEY: VARIANT
<222> LOCATION: (19)..(19)
<223> OTHER INFORMATION: Xaa is Glu or Asp or a conservative
      substitution
<220> FEATURE:
<221> NAME/KEY: VARIANT
<222> LOCATION: (20)..(20)
<223> OTHER INFORMATION: Xaa is Met, Leu, Nle or an oxidatively stable
      Met-replacement amino acid
<220> FEATURE:
<221> NAME/KEY: VARIANT
<222> LOCATION: (21)..(21)
<223> OTHER INFORMATION: Xaa can individually be selected from the group
      consisting of Asn, Asp, Glu, Gln, Lys, His, Arg, Ala, Ser, Thr,
      Pro, Gly, Leu, Ile, Val, Met or Phe
<220> FEATURE:
<221> NAME/KEY: VARIANT
<222> LOCATION: (22)..(22)
<223> OTHER INFORMATION: Xaa is Thr or Lys or a conservative
      substitution
<220> FEATURE:
<221> NAME/KEY: VARIANT
<222> LOCATION: (23)..(23)
<223> OTHER INFORMATION: Xaa is Ile, Glu or Gln or a conservative
      substitution
<220> FEATURE:
<221> NAME/KEY: VARIANT
<222> LOCATION: (24)..(24)
<223> OTHER INFORMATION: Xaa is Leu, Met or Nle or a conservative
      substitution
<220> FEATURE:
<221> NAME/KEY: VARIANT
<222> LOCATION: (25)..(25)
<223> OTHER INFORMATION: Xaa is Asp or Glu or a conservative
      substitution
<220> FEATURE:
```

```
<221> NAME/KEY: VARIANT
<222> LOCATION: (26)..(26)
<223> OTHER INFORMATION: Xaa can individually be selected from the group
      consisting of Asn, Asp, Glu, Gln, Lys, His, Arg, Ala, Ser, Thr,
      Pro, Gly, Leu, Ile, Val, Met or Phe
<220> FEATURE:
<221> NAME/KEY: VARIANT
<222> LOCATION: (27)..(27)
<223> OTHER INFORMATION: Xaa is Leu or Glu or a conservative
      substitution
<220> FEATURE:
<221> NAME/KEY: VARIANT
<222> LOCATION: (28)..(28)
<223> OTHER INFORMATION: Xaa is Ala or Aib or a non-conservative
      substitution
<220> FEATURE:
<221> NAME/KEY: VARIANT
<222> LOCATION: (29)..(29)
<223> OTHER INFORMATION: Xaa is Ala or Thr or a conservative
      substitution
<220> FEATURE:
<221> NAME/KEY: VARIANT
<222> LOCATION: (30)..(30)
<223> OTHER INFORMATION: Xaa can be selected from the group consisting
      of Asn, Asp, Glu, Gln, His, Ala, Ser, Thr, Pro, Gly, Leu, Ile,
      Val, Met or Phe
<220> FEATURE:
<221> NAME/KEY: VARIANT
<222> LOCATION: (31)..(31)
<223> OTHER INFORMATION: Xaa is Asp or Ile or a conservative
      substitution
<220> FEATURE:
<221> NAME/KEY: VARIANT
<222> LOCATION: (34)..(34)
<223> OTHER INFORMATION: Xaa can individually be selected from the group
      consisting of Asn, Asp, Glu, Gln, Lys, His, Arg, Ala, Ser, Thr,
      Pro, Gly, Leu, Ile, Val, Met or Phe
<220> FEATURE:
<221> NAME/KEY: VARIANT
<222> LOCATION: (38)..(38)
<223> OTHER INFORMATION: Xaa can individually be selected from the group
      consisting of Asn, Asp, Glu, Gln, Lys, His, Arg, Ala, Ser, Thr,
      Pro, Gly, Leu, Ile, Val, Met or Phe
<220> FEATURE:
<221> NAME/KEY: VARIANT
<222> LOCATION: (41)..(41)
<223> OTHER INFORMATION: Xaa is Pro, Ile or deleted
<220> FEATURE:
<221> NAME/KEY: VARIANT
<222> LOCATION: (42)..(42)
<223> OTHER INFORMATION: Xaa is Thr or deleted
<220> FEATURE:
<221> NAME/KEY: VARIANT
<222> LOCATION: (43)..(43)
<223> OTHER INFORMATION: Xaa is Asp, Asn or deleted
<220> FEATURE:
<221> NAME/KEY: VARIANT
<222> LOCATION: (44)..(53)
<223> OTHER INFORMATION: May be present or absent. If present,
      represents a peptide sequence of 1 - 10 amino acids wherein each
      Xaa may be absent or is selected from the group consisting of Ala,
      Leu, Ser, Thr, Tyr, Asn, Gln, Asp, Glu, Lys, Arg, His, Met,
      and Orn

<400> SEQUENCE: 2

Xaa Xaa Xaa Xaa Xaa Xaa Xaa Xaa Xaa Xaa His Xaa Xaa Gly Xaa Xaa
1               5                   10                  15

Xaa Xaa Xaa Xaa Xaa Xaa Xaa Xaa Xaa Xaa Xaa Xaa Xaa Xaa Phe
            20                  25                  30

Ile Xaa Trp Leu Ile Xaa Thr Lys Xaa Xaa Xaa Xaa Xaa Xaa Xaa Xaa
        35                  40                  45

Xaa Xaa Xaa Xaa Xaa
    50

<210> SEQ ID NO 3
```

```
<211> LENGTH: 44
<212> TYPE: PRT
<213> ORGANISM: Artificial sequence
<220> FEATURE:
<223> OTHER INFORMATION: Synthetic sequence: Glucagon-like peptide 2
      (GLP-2)
<220> FEATURE:
<221> NAME/KEY: VARIANT
<222> LOCATION: (1)..(10)
<223> OTHER INFORMATION: May be present or absent. If present,
      represents a peptide sequence of 1 - 10 amino acids wherein each
      Xaa may be absent or is selected from the group consisting of Ala,
      Leu, Ser, Thr, Tyr, Asn, Gln, Asp, Glu, Lys, Arg, His, Met,
      and Orn
<220> FEATURE:
<221> NAME/KEY: VARIANT
<222> LOCATION: (12)..(12)
<223> OTHER INFORMATION: Xaa is Gly, Ala or Sar
<220> FEATURE:
<221> NAME/KEY: VARIANT
<222> LOCATION: (13)..(13)
<223> OTHER INFORMATION: Xaa is Glu or Asp
<220> FEATURE:
<221> NAME/KEY: VARIANT
<222> LOCATION: (15)..(15)
<223> OTHER INFORMATION: Xaa is Ser or Thr
<220> FEATURE:
<221> NAME/KEY: VARIANT
<222> LOCATION: (16)..(16)
<223> OTHER INFORMATION: Xaa is Phe or Pro or a conservative
      substitution
<220> FEATURE:
<221> NAME/KEY: VARIANT
<222> LOCATION: (17)..(17)
<223> OTHER INFORMATION: Xaa is Ser or Thr
<220> FEATURE:
<221> NAME/KEY: VARIANT
<222> LOCATION: (18)..(18)
<223> OTHER INFORMATION: Xaa is Asp or Ser or a conservative
      substitution
<220> FEATURE:
<221> NAME/KEY: VARIANT
<222> LOCATION: (19)..(19)
<223> OTHER INFORMATION: Xaa is Glu or Asp or a conservative
      substitution
<220> FEATURE:
<221> NAME/KEY: VARIANT
<222> LOCATION: (20)..(20)
<223> OTHER INFORMATION: Xaa is Met, Leu, Nle or an oxidatively stable
      Met-replacement amino acid
<220> FEATURE:
<221> NAME/KEY: VARIANT
<222> LOCATION: (22)..(22)
<223> OTHER INFORMATION: Xaa is Thr or Lys or a conservative
      substitution
<220> FEATURE:
<221> NAME/KEY: VARIANT
<222> LOCATION: (23)..(23)
<223> OTHER INFORMATION: Xaa is Ile, Glu or Gln or a conservative
      substitution
<220> FEATURE:
<221> NAME/KEY: VARIANT
<222> LOCATION: (24)..(24)
<223> OTHER INFORMATION: Xaa is Leu, Met or Nle or a conservative
      substitution
<220> FEATURE:
<221> NAME/KEY: VARIANT
<222> LOCATION: (25)..(25)
<223> OTHER INFORMATION: Xaa is Asp or Glu or a conservative
      substitution
<220> FEATURE:
<221> NAME/KEY: VARIANT
<222> LOCATION: (27)..(27)
<223> OTHER INFORMATION: Xaa is Leu or Glu or a conservative
      substitution
<220> FEATURE:
<221> NAME/KEY: VARIANT
<222> LOCATION: (28)..(28)
<223> OTHER INFORMATION: Xaa is Ala or Aib or a non-conservative
      substitution
```

```
-continued

<220> FEATURE:
<221> NAME/KEY: VARIANT
<222> LOCATION: (29)..(29)
<223> OTHER INFORMATION: Xaa is Ala or Thr or a conservative
      substitution
<220> FEATURE:
<221> NAME/KEY: VARIANT
<222> LOCATION: (31)..(31)
<223> OTHER INFORMATION: Xaa is Asp or Ile or a conservative
      substitution
<220> FEATURE:
<221> NAME/KEY: VARIANT
<222> LOCATION: (41)..(41)
<223> OTHER INFORMATION: Xaa is Pro, Ile or deleted
<220> FEATURE:
<221> NAME/KEY: VARIANT
<222> LOCATION: (42)..(42)
<223> OTHER INFORMATION: Xaa is Thr or deleted
<220> FEATURE:
<221> NAME/KEY: VARIANT
<222> LOCATION: (43)..(43)
<223> OTHER INFORMATION: Xaa is Asp, Asn or deleted

<400> SEQUENCE: 3

Xaa Xaa Xaa Xaa Xaa Xaa Xaa Xaa Xaa Xaa His Xaa Xaa Gly Xaa Xaa
1               5                   10                  15

Xaa Xaa Xaa Xaa Ser Xaa Xaa Xaa Ala Xaa Xaa Xaa Arg Xaa Phe
            20                  25                  30

Ile Ala Trp Leu Ile Ala Thr Lys Xaa Xaa Xaa Lys
        35                  40

<210> SEQ ID NO 4
<211> LENGTH: 53
<212> TYPE: PRT
<213> ORGANISM: Artificial sequence
<220> FEATURE:
<223> OTHER INFORMATION: Synthetic sequence: General Formula II of Claim
      4 of PCT/GB2007/004273
<220> FEATURE:
<221> NAME/KEY: VARIANT
<222> LOCATION: (1)..(10)
<223> OTHER INFORMATION: May be present or absent. If present,
      represents a peptide sequence of 1 - 10 amino acids wherein each
      Xaa may be absent or is selected from the group consisting of Ala,
      Leu, Ser, Thr, Tyr, Asn, Gln, Asp, Glu, Lys, Arg, His, Met,
      and Orn
<220> FEATURE:
<221> NAME/KEY: VARIANT
<222> LOCATION: (12)..(12)
<223> OTHER INFORMATION: Xaa is Gly, Ala or Sar
<220> FEATURE:
<221> NAME/KEY: VARIANT
<222> LOCATION: (13)..(13)
<223> OTHER INFORMATION: Xaa is Glu or Asp
<220> FEATURE:
<221> NAME/KEY: VARIANT
<222> LOCATION: (15)..(15)
<223> OTHER INFORMATION: Xaa is Ser or Thr
<220> FEATURE:
<221> NAME/KEY: VARIANT
<222> LOCATION: (16)..(16)
<223> OTHER INFORMATION: Xaa is Phe or Pro
<220> FEATURE:
<221> NAME/KEY: VARIANT
<222> LOCATION: (17)..(17)
<223> OTHER INFORMATION: Xaa is Ser or Thr
<220> FEATURE:
<221> NAME/KEY: VARIANT
<222> LOCATION: (18)..(18)
<223> OTHER INFORMATION: Xaa is Asp or Ser
<220> FEATURE:
<221> NAME/KEY: VARIANT
<222> LOCATION: (19)..(19)
<223> OTHER INFORMATION: Xaa is Glu or Asp
<220> FEATURE:
<221> NAME/KEY: VARIANT
```

```
<222> LOCATION: (20)..(20)
<223> OTHER INFORMATION: Xaa is Met, Leu, Nle or an oxidatively stable
      Met-replacement amino acid
<220> FEATURE:
<221> NAME/KEY: VARIANT
<222> LOCATION: (21)..(21)
<223> OTHER INFORMATION: Xaa is Asn, Ala, Glu, Gly, Ile, Leu, Lys, Met,
      Phe, Ser, Thr or Val
<220> FEATURE:
<221> NAME/KEY: VARIANT
<222> LOCATION: (22)..(22)
<223> OTHER INFORMATION: Xaa is Thr or Lys
<220> FEATURE:
<221> NAME/KEY: VARIANT
<222> LOCATION: (23)..(23)
<223> OTHER INFORMATION: Xaa is Ile, Glu or Gln
<220> FEATURE:
<221> NAME/KEY: VARIANT
<222> LOCATION: (24)..(24)
<223> OTHER INFORMATION: Xaa is Leu, Met or Nle
<220> FEATURE:
<221> NAME/KEY: VARIANT
<222> LOCATION: (25)..(25)
<223> OTHER INFORMATION: Xaa is Asp or Glu
<220> FEATURE:
<221> NAME/KEY: VARIANT
<222> LOCATION: (26)..(26)
<223> OTHER INFORMATION: Xaa is Asn, Ala, Glu, Gly, Ile, Leu, Lys, Met,
      Phe, Ser, Thr or Val
<220> FEATURE:
<221> NAME/KEY: VARIANT
<222> LOCATION: (27)..(27)
<223> OTHER INFORMATION: Xaa is Leu or Glu
<220> FEATURE:
<221> NAME/KEY: VARIANT
<222> LOCATION: (28)..(28)
<223> OTHER INFORMATION: Xaa is Ala or Aib
<220> FEATURE:
<221> NAME/KEY: VARIANT
<222> LOCATION: (29)..(29)
<223> OTHER INFORMATION: Xaa is Ala or Thr
<220> FEATURE:
<221> NAME/KEY: VARIANT
<222> LOCATION: (30)..(30)
<223> OTHER INFORMATION: Xaa is Asn, Ala, Glu, Gly, Ile, Leu, Met, Phe,
      Ser, Thr or Val
<220> FEATURE:
<221> NAME/KEY: VARIANT
<222> LOCATION: (31)..(31)
<223> OTHER INFORMATION: Xaa is Asp or Ile
<220> FEATURE:
<221> NAME/KEY: VARIANT
<222> LOCATION: (34)..(34)
<223> OTHER INFORMATION: Xaa is Asn, Ala, Glu, Gly, Ile, Leu, Lys, Met,
      Phe, Ser, Thr or Val
<220> FEATURE:
<221> NAME/KEY: VARIANT
<222> LOCATION: (38)..(38)
<223> OTHER INFORMATION: Xaa is Asn, Ala, Glu, Gly, Ile, Leu, Lys, Met,
      Phe, Ser, Thr or Val
<220> FEATURE:
<221> NAME/KEY: VARIANT
<222> LOCATION: (41)..(41)
<223> OTHER INFORMATION: Xaa is Pro, Ile or deleted
<220> FEATURE:
<221> NAME/KEY: VARIANT
<222> LOCATION: (42)..(42)
<223> OTHER INFORMATION: Xaa is Thr or deleted
<220> FEATURE:
<221> NAME/KEY: VARIANT
<222> LOCATION: (43)..(43)
<223> OTHER INFORMATION: Xaa is Asp, Asn or deleted
<220> FEATURE:
<221> NAME/KEY: VARIANT
<222> LOCATION: (44)..(53)
<223> OTHER INFORMATION: May be present or absent. If present,
      represents a peptide sequence of 1 - 10 amino acids wherein each
      Xaa may be absent or is selected from the group consisting of Ala,
      Leu, Ser, Thr, Tyr, Asn, Gln, Asp, Glu, Lys, Arg, His, Met,
      and Orn
```

```
<400> SEQUENCE: 4

Xaa Xaa Xaa Xaa Xaa Xaa Xaa Xaa Xaa His Xaa Xaa Gly Xaa Xaa
1               5                   10                  15

Xaa Xaa Xaa Xaa Xaa Xaa Xaa Xaa Xaa Xaa Ala Xaa Xaa Xaa Phe
                20                  25                  30

Ile Xaa Trp Leu Ile Xaa Thr Lys Xaa Xaa Xaa Xaa Xaa Xaa Xaa
        35                  40                  45

Xaa Xaa Xaa Xaa Xaa
    50

<210> SEQ ID NO 5
<211> LENGTH: 44
<212> TYPE: PRT
<213> ORGANISM: Artificial sequence
<220> FEATURE:
<223> OTHER INFORMATION: Synthetic sequence: Glucagon-like peptide 2
      (GLP-2)
<220> FEATURE:
<221> NAME/KEY: VARIANT
<222> LOCATION: (1)..(10)
<223> OTHER INFORMATION: May be present or absent. If present,
      represents a peptide sequence of 1 - 10 amino acids wherein each
      Xaa may be absent or is selected from the group consisting of Ala,
      Leu, Ser, Thr, Tyr, Asn, Gln, Asp, Glu, Lys, Arg, His, Met,
      and Orn
<220> FEATURE:
<221> NAME/KEY: VARIANT
<222> LOCATION: (12)..(12)
<223> OTHER INFORMATION: Xaa is Gly, Ala or Sar
<220> FEATURE:
<221> NAME/KEY: VARIANT
<222> LOCATION: (13)..(13)
<223> OTHER INFORMATION: Xaa is Glu or Asp
<220> FEATURE:
<221> NAME/KEY: VARIANT
<222> LOCATION: (15)..(15)
<223> OTHER INFORMATION: Xaa is Ser or Thr
<220> FEATURE:
<221> NAME/KEY: VARIANT
<222> LOCATION: (16)..(16)
<223> OTHER INFORMATION: Xaa is Phe or Pro
<220> FEATURE:
<221> NAME/KEY: VARIANT
<222> LOCATION: (17)..(17)
<223> OTHER INFORMATION: Xaa is Ser or Thr
<220> FEATURE:
<221> NAME/KEY: VARIANT
<222> LOCATION: (18)..(18)
<223> OTHER INFORMATION: Xaa is Asp or Ser
<220> FEATURE:
<221> NAME/KEY: VARIANT
<222> LOCATION: (19)..(19)
<223> OTHER INFORMATION: Xaa is Glu or Asp
<220> FEATURE:
<221> NAME/KEY: VARIANT
<222> LOCATION: (20)..(20)
<223> OTHER INFORMATION: Xaa is Met, Leu, Nle or an oxidatively stable
      Met-replacement amino acid
<220> FEATURE:
<221> NAME/KEY: VARIANT
<222> LOCATION: (22)..(22)
<223> OTHER INFORMATION: Xaa is Thr or Lys
<220> FEATURE:
<221> NAME/KEY: VARIANT
<222> LOCATION: (23)..(23)
<223> OTHER INFORMATION: Xaa is Ile, Glu or Gln
<220> FEATURE:
<221> NAME/KEY: VARIANT
<222> LOCATION: (24)..(24)
<223> OTHER INFORMATION: Xaa is Leu, Met or Nle
<220> FEATURE:
<221> NAME/KEY: VARIANT
<222> LOCATION: (25)..(25)
<223> OTHER INFORMATION: Xaa is Asp or Glu
```

```
<220> FEATURE:
<221> NAME/KEY: VARIANT
<222> LOCATION: (27)..(27)
<223> OTHER INFORMATION: Xaa is Leu or Glu
<220> FEATURE:
<221> NAME/KEY: VARIANT
<222> LOCATION: (28)..(28)
<223> OTHER INFORMATION: Xaa is Ala or Aib
<220> FEATURE:
<221> NAME/KEY: VARIANT
<222> LOCATION: (29)..(29)
<223> OTHER INFORMATION: Xaa is Ala or Thr
<220> FEATURE:
<221> NAME/KEY: VARIANT
<222> LOCATION: (31)..(31)
<223> OTHER INFORMATION: Xaa is Asp or Ile
<220> FEATURE:
<221> NAME/KEY: VARIANT
<222> LOCATION: (41)..(41)
<223> OTHER INFORMATION: Xaa is Pro, Ile or deleted
<220> FEATURE:
<221> NAME/KEY: VARIANT
<222> LOCATION: (42)..(42)
<223> OTHER INFORMATION: Xaa is Thr or deleted
<220> FEATURE:
<221> NAME/KEY: VARIANT
<222> LOCATION: (43)..(43)
<223> OTHER INFORMATION: Xaa is Asp, Asn or deleted

<400> SEQUENCE: 5

Xaa Xaa Xaa Xaa Xaa Xaa Xaa Xaa Xaa Xaa His Xaa Xaa Gly Xaa Xaa
1               5                   10                  15

Xaa Xaa Xaa Xaa Ser Xaa Xaa Xaa Xaa Ala Xaa Ala Xaa Arg Xaa Phe
            20                  25                  30

Ile Ala Trp Leu Ile Ala Thr Lys Xaa Xaa Xaa Lys
        35                  40

<210> SEQ ID NO 6
<211> LENGTH: 33
<212> TYPE: PRT
<213> ORGANISM: Artificial sequence
<220> FEATURE:
<223> OTHER INFORMATION: Synthetic sequence: General Formula III of
      Claim 10 of PCT/GB2007/004273
<220> FEATURE:
<221> NAME/KEY: misc_feature
<222> LOCATION: (8)..(8)
<223> OTHER INFORMATION: Xaa is Asp or Ser, preferably Ser
<220> FEATURE:
<221> NAME/KEY: misc_feature
<222> LOCATION: (11)..(11)
<223> OTHER INFORMATION: Xaa is Ser, Ala, Glu, Lys or Asn
<220> FEATURE:
<221> NAME/KEY: misc_feature
<222> LOCATION: (15)..(15)
<223> OTHER INFORMATION: Xaa is Glu or Asp, preferably Glu
<220> FEATURE:
<221> NAME/KEY: misc_feature
<222> LOCATION: (16)..(16)
<223> OTHER INFORMATION: Xaa is Ser, Ala or Glu
<220> FEATURE:
<221> NAME/KEY: misc_feature
<222> LOCATION: (20)..(20)
<223> OTHER INFORMATION: Xaa is Ser, Ala or Glu
<220> FEATURE:
<221> NAME/KEY: misc_feature
<222> LOCATION: (24)..(24)
<223> OTHER INFORMATION: Xaa is Ser, Ala or Glu
<220> FEATURE:
<221> NAME/KEY: misc_feature
<222> LOCATION: (28)..(28)
<223> OTHER INFORMATION: Xaa is Ser, Ala or Glu

<400> SEQUENCE: 6

His Gly Glu Gly Ser Phe Ser Xaa Glu Leu Xaa Thr Ile Leu Xaa Xaa
```

```
                1               5                  10                 15
Leu Ala Ala Xaa Asp Phe Ile Xaa Trp Leu Ile Xaa Thr Lys Ile Thr
            20                  25                 30

Asp

<210> SEQ ID NO 7
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 7

His Gly Glu Gly Ser Phe Ser Asp Glu Leu Ser Thr Ile Leu Glu Ser
1               5                  10                 15

Leu Ala Ala Ser Asp Phe Ile Ser Trp Leu Ile Ser Thr Lys Ile Thr
            20                  25                 30

Asp

<210> SEQ ID NO 8
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 8

His Gly Glu Gly Ser Phe Ser Asp Glu Leu Ala Thr Ile Leu Glu Ala
1               5                  10                 15

Leu Ala Ala Ala Asp Phe Ile Ala Trp Leu Ile Ala Thr Lys Ile Thr
            20                  25                 30

Asp

<210> SEQ ID NO 9
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 9

His Gly Glu Gly Ser Phe Ser Asp Glu Leu Glu Thr Ile Leu Glu Glu
1               5                  10                 15

Leu Ala Ala Glu Asp Phe Ile Glu Trp Leu Ile Glu Thr Lys Ile Thr
            20                  25                 30

Asp

<210> SEQ ID NO 10
<211> LENGTH: 33
<212> TYPE: PRT
<213> ORGANISM: Artificial sequence
<220> FEATURE:
<223> OTHER INFORMATION: Synthetic sequence: GLP-2 analogue
```

```
<220> FEATURE:
<221> NAME/KEY: MOD_RES
<222> LOCATION: (33)..(33)
<223> OTHER INFORMATION: AMIDATION

<400> SEQUENCE: 10

His Gly Glu Gly Ser Phe Ser Asp Glu Leu Ser Thr Ile Leu Glu Ser
1               5                   10                  15

Leu Ala Ala Ala Asp Phe Ile Ala Trp Leu Ile Ala Thr Lys Ile Thr
            20                  25                  30

Asp

<210> SEQ ID NO 11
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 11

His Gly Glu Gly Ser Phe Ser Asp Glu Leu Ala Thr Ile Leu Glu Ala
1               5                   10                  15

Leu Ala Ala Ser Asp Phe Ile Ser Trp Leu Ile Ser Thr Lys Ile Thr
            20                  25                  30

Asp

<210> SEQ ID NO 12
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 12

His Gly Glu Gly Ser Phe Ser Asp Glu Leu Lys Thr Ile Leu Glu Ser
1               5                   10                  15

Leu Ala Ala Ala Asp Phe Ile Glu Trp Leu Ile Gln Thr Lys Ile Thr
            20                  25                  30

Asp

<210> SEQ ID NO 13
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 13

His Gly Glu Gly Ser Phe Ser Asp Glu Leu Asn Thr Ile Leu Glu Ser
1               5                   10                  15

Leu Ala Ala Ser Asp Phe Ile Ser Trp Leu Ile Ser Thr Lys Ile Thr
            20                  25                  30

Asp
```

```
<210> SEQ ID NO 14
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 14

His Gly Glu Gly Ser Phe Ser Asp Glu Leu Ala Thr Ile Leu Glu Ser
1               5                   10                  15

Leu Ala Ala Ala Asp Phe Ile Ser Trp Leu Ile Ala Thr Lys Ile Thr
            20                  25                  30

Asp

<210> SEQ ID NO 15
<211> LENGTH: 34
<212> TYPE: PRT
<213> ORGANISM: Artificial sequence
<220> FEATURE:
<223> OTHER INFORMATION: Synthetic sequence: GLP-2 analogue

<400> SEQUENCE: 15

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys

<210> SEQ ID NO 16
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 16

His Gly Glu Gly Ser Phe Ser Asp Glu Leu Glu Thr Ile Leu Glu Glu
1               5                   10                  15

Leu Ala Ala Glu Asp Phe Ile Glu Trp Leu Ile Glu Thr Lys Ile Thr
            20                  25                  30

Asp Lys Lys Lys Lys Lys Lys
        35

<210> SEQ ID NO 17
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 17

His Gly Glu Gly Ser Phe Ser Asp Glu Leu Lys Thr Ile Leu Glu Ser
1               5                   10                  15
```

Leu Ala Ala Ala Asp Phe Ile Glu Trp Leu Ile Gln Thr Lys Ile Thr
            20                  25                  30

Asp Lys Lys Lys Lys Lys Lys
        35

<210> SEQ ID NO 18
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 18

His Gly Glu Gly Ser Phe Ser Asp Glu Leu Ser Thr Ile Leu Glu Ser
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 19
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 19

His Gly Glu Gly Ser Phe Ser Asp Glu Leu Ala Thr Ile Leu Glu Ala
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 20
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 20

His Gly Glu Gly Ser Phe Ser Asp Glu Leu Asn Thr Ile Leu Glu Ser
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 21
<211> LENGTH: 39
<212> TYPE: PRT

-continued

```
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 21

His Gly Glu Gly Ser Phe Ser Asp Glu Leu Asn Thr Ile Leu Glu Ser
1               5                   10                  15

Leu Ala Ala Arg Asp Phe Ile Ser Trp Leu Ile Ser Thr Lys Ile Thr
            20                  25                  30

Asp Lys Lys Lys Lys Lys Lys
        35

<210> SEQ ID NO 22
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 22

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ser Thr Lys Ile Thr
            20                  25                  30

Asp Lys Lys Lys Lys Lys Lys
        35

<210> SEQ ID NO 23
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 23

His Gly Glu Gly Ser Phe Ser Asp Glu Leu Ser Thr Ile Leu Glu Ala
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 24
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 24

His Gly Glu Gly Ser Phe Ser Asp Glu Leu Ala Thr Ile Leu Glu Ser
```

```
                    1               5                   10                  15
Leu Ala Ala Ser Asp Phe Ile Ser Trp Leu Ile Ser Thr Lys Ile Thr
                    20                  25                  30

Asp Lys Lys Lys Lys Lys Lys
                    35

<210> SEQ ID NO 25
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 25

His Gly Glu Gly Ser Phe Ser Asp Glu Leu Leu Thr Ile Leu Glu Leu
1               5                   10                  15

Leu Ala Ala Ser Asp Phe Ile Ser Trp Leu Ile Ser Thr Lys Ile Thr
                    20                  25                  30

Asp Lys Lys Lys Lys Lys Lys
                    35

<210> SEQ ID NO 26
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 26

His Gly Glu Gly Ser Phe Ser Asp Glu Leu Lys Thr Ile Leu Glu Lys
1               5                   10                  15

Leu Ala Ala Lys Asp Phe Ile Lys Trp Leu Ile Lys Thr Lys Ile Thr
                    20                  25                  30

Asp Lys Lys Lys Lys Lys Lys
                    35

<210> SEQ ID NO 27
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 27

His Gly Glu Gly Ser Phe Ser Asp Glu Leu Phe Thr Ile Leu Glu Phe
1               5                   10                  15

Leu Ala Ala Ser Asp Phe Ile Ser Trp Leu Ile Ser Thr Lys Ile Thr
                    20                  25                  30

Asp Lys Lys Lys Lys Lys Lys
                    35

<210> SEQ ID NO 28
<211> LENGTH: 33
```

```
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 28

His Gly Glu Gly Ser Phe Ser Asp Glu Leu Ala Thr Ile Leu Glu Ala
 1               5                  10                  15

Leu Ala Ala Ala Asp Phe Ile Ala Trp Leu Ile Ser Thr Lys Ile Thr
            20                  25                  30

Asp

<210> SEQ ID NO 29
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 29

His Gly Glu Gly Ser Phe Ser Asp Glu Leu Ser Thr Ile Leu Glu Ala
 1               5                  10                  15

Leu Ala Ala Ser Asp Phe Ile Ser Trp Leu Ile Ser Thr Lys Ile Thr
            20                  25                  30

Asp

<210> SEQ ID NO 30
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 30

His Gly Glu Gly Ser Phe Ser Asp Glu Leu Ala Thr Ile Leu Glu Ser
 1               5                  10                  15

Leu Ala Ala Ser Asp Phe Ile Ser Trp Leu Ile Ser Thr Lys Ile Thr
            20                  25                  30

Asp

<210> SEQ ID NO 31
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 31

His Gly Glu Gly Ser Phe Ser Asp Glu Leu Leu Thr Ile Leu Glu Leu
 1               5                  10                  15
```

```
Leu Ala Ala Ser Asp Phe Ile Ser Trp Leu Ile Ser Thr Lys Ile Thr
            20                  25                  30

Asp

<210> SEQ ID NO 32
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 32

His Gly Glu Gly Ser Phe Ser Asp Glu Leu Phe Thr Ile Leu Glu Phe
1               5                   10                  15

Leu Ala Ala Ser Asp Phe Ile Ser Trp Leu Ile Ser Thr Lys Ile Thr
            20                  25                  30

Asp

<210> SEQ ID NO 33
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 33

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ala Thr Lys Ile Thr
            20                  25                  30

Asp Lys Lys Lys Lys Lys Lys
        35

<210> SEQ ID NO 34
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 34

His Gly Glu Gly Ser Phe Ser Asp Glu Leu Ser Thr Ile Leu Glu Ser
1               5                   10                  15

Leu Ala Ala Ala Asp Phe Ile Ala Trp Leu Ile Ala Thr Lys Ile Thr
            20                  25                  30

Asp Lys Lys Lys Lys Lys Lys
        35

<210> SEQ ID NO 35
<211> LENGTH: 39
<212> TYPE: PRT
<213> ORGANISM: Artificial sequence
<220> FEATURE:
<223> OTHER INFORMATION: Synthetic sequence: GLP-2 analogue
```

```
<220> FEATURE:
<221> NAME/KEY: MOD_RES
<222> LOCATION: (39)..(39)
<223> OTHER INFORMATION: AMIDATION

<400> SEQUENCE: 35

His Gly Glu Gly Ser Phe Ser Asp Glu Leu Ser Thr Ile Leu Glu Ala
1               5                   10                  15

Leu Ala Ala Ala Asp Phe Ile Ala Trp Leu Ile Ala Thr Lys Ile Thr
            20                  25                  30

Asp Lys Lys Lys Lys Lys Lys
        35

<210> SEQ ID NO 36
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 36

His Gly Glu Gly Ser Phe Ser Asp Glu Leu Ala Thr Ile Leu Glu Ala
1               5                   10                  15

Leu Ala Ala Ala Asp Phe Ile Ser Trp Leu Ile Ala Thr Lys Ile Thr
            20                  25                  30

Asp Lys Lys Lys Lys Lys Lys
        35

<210> SEQ ID NO 37
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 37

His Gly Glu Gly Ser Phe Ser Asp Glu Leu Leu Thr Ile Leu Glu Leu
1               5                   10                  15

Leu Ala Ala Ala Asp Phe Ile Ala Trp Leu Ile Ala Thr Lys Ile Thr
            20                  25                  30

Asp Lys Lys Lys Lys Lys Lys
        35

<210> SEQ ID NO 38
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 38

His Gly Glu Gly Ser Phe Ser Asp Glu Leu Ala Thr Ile Leu Glu Ser
1               5                   10                  15

Leu Ala Ala Ala Asp Phe Ile Ser Trp Leu Ile Ala Thr Lys Ile Thr
```

```
                20                  25                  30
Asp Lys Lys Lys Lys Lys Lys
        35

<210> SEQ ID NO 39
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 39

His Gly Glu Gly Ser Phe Ser Asp Glu Leu Ala Thr Ile Leu Glu Ser
1               5                   10                  15

Leu Ala Ala Ala Asp Phe Ile Ala Trp Leu Ile Ala Thr Lys Ile Thr
            20                  25                  30

Asp

<210> SEQ ID NO 40
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 40

His Gly Glu Gly Ser Phe Ser Asp Glu Leu Ala Thr Ile Leu Glu Ser
1               5                   10                  15

Leu Ala Ala Ala Asp Phe Ile Ala Trp Leu Ile Ala Thr Lys Ile Thr
            20                  25                  30

Asp Lys Lys Lys Lys Lys Lys
        35

<210> SEQ ID NO 41
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 41

His Gly Glu Gly Ser Phe Ser Asp Glu Leu Leu Thr Ile Leu Glu Leu
1               5                   10                  15

Leu Ala Ala Leu Asp Phe Ile Ala Trp Leu Ile Ala Thr Lys Ile Thr
            20                  25                  30

Asp Lys Lys Lys Lys Lys Lys
        35

<210> SEQ ID NO 42
<211> LENGTH: 33
<212> TYPE: PRT
<213> ORGANISM: Artificial sequence
<220> FEATURE:
<223> OTHER INFORMATION: Synthetic sequence: GLP-2 analogue
```

```
<220> FEATURE:
<221> NAME/KEY: MOD_RES
<222> LOCATION: (33)..(33)
<223> OTHER INFORMATION: AMIDATION

<400> SEQUENCE: 42

His Gly Glu Gly Ser Phe Ser Asp Glu Leu Ala Thr Ile Leu Glu Ala
1               5                   10                  15

Leu Ala Ala Ser Asp Phe Ile Ala Trp Leu Ile Ala Thr Lys Ile Thr
            20                  25                  30

Asp

<210> SEQ ID NO 43
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 43

His Gly Glu Gly Ser Phe Ser Asp Glu Leu Ala Thr Ile Leu Glu Ala
1               5                   10                  15

Leu Ala Ala Ala Asp Phe Ile Ser Trp Leu Ile Ala Thr Lys Ile Thr
            20                  25                  30

Asp

<210> SEQ ID NO 44
<211> LENGTH: 33
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (33)..(33)
<223> OTHER INFORMATION: AMIDATION

<400> SEQUENCE: 44

His Gly Glu Gly Ser Phe Ser Asp Glu Leu Ser Thr Ile Leu Glu Ala
1               5                   10                  15

Leu Ala Ala Ala Asp Phe Ile Ala Trp Leu Ile Ala Thr Lys Ile Thr
            20                  25                  30

Asp

<210> SEQ ID NO 45
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 45

His Gly Glu Gly Ser Phe Ser Asp Glu Leu Ala Thr Ile Leu Glu Ala
1               5                   10                  15

Leu Ala Ala Ser Asp Phe Ile Ala Trp Leu Ile Ala Thr Lys Ile Thr
            20                  25                  30

Asp Lys Lys Lys Lys Lys Lys
```

-continued

```
<210> SEQ ID NO 46
<211> LENGTH: 39
<212> TYPE: PRT
<213> ORGANISM: Artificial sequence
<220> FEATURE:
<223> OTHER INFORMATION: Synthetic sequence: GLP-2 analogue
<220> FEATURE:
<221> NAME/KEY: MOD_RES
<222> LOCATION: (39)..(39)
<223> OTHER INFORMATION: AMIDATION

<400> SEQUENCE: 46

His Gly Glu Gly Ser Phe Ser Asp Glu Leu Leu Thr Ile Leu Glu Leu
1               5                   10                  15

Leu Ala Ala Leu Asp Phe Ile Leu Trp Leu Ile Leu Thr Lys Ile Thr
            20                  25                  30

Asp Lys Lys Lys Lys Lys Lys
        35

<210> SEQ ID NO 47
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 47

His Gly Glu Gly Ser Phe Ser Asp Glu Leu Leu Thr Ile Leu Glu Leu
1               5                   10                  15

Leu Ala Ala Leu Asp Phe Ile Leu Trp Leu Ile Leu Thr Lys Ile Thr
            20                  25                  30

Asp

<210> SEQ ID NO 48
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 48

His Gly Glu Gly Ser Phe Ser Asp Glu Leu Phe Thr Ile Leu Glu Phe
1               5                   10                  15

Leu Ala Ala Phe Asp Phe Ile Phe Trp Leu Ile Phe Thr Lys Ile Thr
            20                  25                  30

Asp

<210> SEQ ID NO 49
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 49

His Gly Glu Gly Ser Phe Ser Asp Glu Leu Val Thr Ile Leu Glu Val
1               5                   10                  15

Leu Ala Ala Val Asp Phe Ile Val Trp Leu Ile Val Thr Lys Ile Thr
            20                  25                  30

Asp
```

```
<210> SEQ ID NO 50
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 50

His Gly Glu Gly Ser Phe Ser Asp Glu Leu Ile Thr Ile Leu Glu Ile
1               5                   10                  15

Leu Ala Ala Ile Asp Phe Ile Ile Trp Leu Ile Ile Thr Lys Ile Thr
            20                  25                  30

Asp

<210> SEQ ID NO 51
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 51

His Gly Glu Gly Ser Phe Ser Asp Glu Leu Ile Thr Ile Leu Glu Ile
1               5                   10                  15

Leu Ala Ala Ser Asp Phe Ile Ser Trp Leu Ile Ser Thr Lys Ile Thr
            20                  25                  30

Asp

<210> SEQ ID NO 52
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 52

His Gly Glu Gly Ser Phe Ser Asp Glu Leu Val Thr Ile Leu Glu Val
1               5                   10                  15

Leu Ala Ala Ser Asp Phe Ile Ser Trp Leu Ile Ser Thr Lys Ile Thr
            20                  25                  30

Asp

<210> SEQ ID NO 53
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 53

His Gly Glu Gly Ser Phe Ser Asp Glu Leu Ala Thr Ile Leu Glu Ala
1               5                   10                  15

Leu Ala Ala Gly Asp Phe Ile Gly Trp Leu Ile Gly Thr Lys Ile Thr
            20                  25                  30

Asp

<210> SEQ ID NO 54
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 54
```

His Gly Glu Gly Ser Phe Ser Asp Glu Leu Leu Thr Ile Leu Glu Leu
1               5                   10                  15

Leu Ala Ala Gly Asp Phe Ile Gly Trp Leu Ile Gly Thr Lys Ile Thr
            20                  25                  30

Asp

<210> SEQ ID NO 55
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 55

His Gly Glu Gly Ser Phe Ser Asp Glu Leu Ile Thr Ile Leu Glu Ile
1               5                   10                  15

Leu Ala Ala Gly Asp Phe Ile Gly Trp Leu Ile Gly Thr Lys Ile Thr
            20                  25                  30

Asp

<210> SEQ ID NO 56
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 56

His Gly Glu Gly Ser Phe Ser Asp Glu Leu Val Thr Ile Leu Glu Val
1               5                   10                  15

Leu Ala Ala Gly Asp Phe Ile Gly Trp Leu Ile Gly Thr Lys Ile Thr
            20                  25                  30

Asp

<210> SEQ ID NO 57
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 57

His Gly Glu Gly Ser Phe Ser Asp Glu Leu Phe Thr Ile Leu Glu Phe
1               5                   10                  15

Leu Ala Ala Gly Asp Phe Ile Gly Trp Leu Ile Gly Thr Lys Ile Thr
            20                  25                  30

Asp

<210> SEQ ID NO 58
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 58

His Gly Glu Gly Ser Phe Ser Asp Glu Leu Ala Thr Ile Leu Glu Ala
1               5                   10                  15

Leu Ala Ala Ala Asp Phe Ile Ser Trp Leu Ile Ser Thr Lys Ile Thr
            20                  25                  30

Asp

<210> SEQ ID NO 59
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 59

His Gly Glu Gly Ser Phe Ser Asp Glu Leu Ala Thr Ile Leu Glu Ala
1               5                   10                  15
Leu Ala Ala Ser Asp Phe Ile Ser Trp Leu Ile Ala Thr Lys Ile Thr
            20                  25                  30
Asp

<210> SEQ ID NO 60
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 60

His Gly Glu Gly Ser Phe Ser Asp Glu Leu Ala Thr Ile Leu Glu Ala
1               5                   10                  15
Leu Ala Ala Ser Asp Phe Ile Ala Trp Leu Ile Ser Thr Lys Ile Thr
            20                  25                  30
Asp

<210> SEQ ID NO 61
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 61

His Gly Glu Gly Ser Phe Ser Asp Glu Leu Ala Thr Ile Leu Glu Ser
1               5                   10                  15
Leu Ala Ala Ser Asp Phe Ile Ala Trp Leu Ile Ala Thr Lys Ile Thr
            20                  25                  30
Asp

<210> SEQ ID NO 62
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 62

His Gly Glu Gly Ser Phe Ser Asp Glu Leu Ser Thr Ile Leu Glu Ser
1               5                   10                  15
Leu Ala Ala Ala Asp Phe Ile Ala Trp Leu Ile Ala Thr Lys Ile Thr
            20                  25                  30
Asp

<210> SEQ ID NO 63
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 63

His Gly Glu Gly Ser Phe Ser Asp Glu Leu Ser Thr Ile Leu Glu Ala
1               5                   10                  15

Leu Ala Ala Ser Asp Phe Ile Ala Trp Leu Ile Ala Thr Lys Ile Thr
            20                  25                  30

Asp

<210> SEQ ID NO 64
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 64

His Gly Glu Gly Ser Phe Ser Asp Glu Leu Ala Thr Ile Leu Glu Ser
1               5                   10                  15

Leu Ala Ala Ala Asp Phe Ile Ala Trp Leu Ile Ser Thr Lys Ile Thr
            20                  25                  30

Asp

<210> SEQ ID NO 65
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 65

His Gly Glu Gly Ser Phe Ser Asp Glu Leu Ser Thr Ile Leu Glu Ala
1               5                   10                  15

Leu Ala Ala Ala Asp Phe Ile Ser Trp Leu Ile Ala Thr Lys Ile Thr
            20                  25                  30

Asp

<210> SEQ ID NO 66
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 66

His Gly Glu Gly Ser Phe Ser Asp Glu Leu Ser Thr Ile Leu Glu Ala
1               5                   10                  15

Leu Ala Ala Ala Asp Phe Ile Ala Trp Leu Ile Ser Thr Lys Ile Thr
            20                  25                  30

Asp

<210> SEQ ID NO 67
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 67

His Gly Glu Gly Ser Phe Ser Asp Glu Leu Ser Thr Ile Leu Glu Ser
1               5                   10                  15

Leu Ala Ala Ser Asp Phe Ile Ser Trp Leu Ile Ala Thr Lys Ile Thr
            20                  25                  30

Asp

<210> SEQ ID NO 68
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 68

His Gly Glu Gly Ser Phe Ser Asp Glu Leu Ser Thr Ile Leu Glu Ser
1               5                   10                  15

Leu Ala Ala Ser Asp Phe Ile Ala Trp Leu Ile Ser Thr Lys Ile Thr
            20                  25                  30

Asp

<210> SEQ ID NO 69
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 69

His Gly Glu Gly Ser Phe Ser Asp Glu Leu Ser Thr Ile Leu Glu Ser
1               5                   10                  15

Leu Ala Ala Ala Asp Phe Ile Ser Trp Leu Ile Ser Thr Lys Ile Thr
            20                  25                  30

Asp

<210> SEQ ID NO 70
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 70

His Gly Glu Gly Ser Phe Ser Asp Glu Leu Ser Thr Ile Leu Glu Ser
1               5                   10                  15

Leu Ala Ala Ser Asp Phe Ile Ala Trp Leu Ile Ala Thr Lys Ile Thr
            20                  25                  30

Asp

<210> SEQ ID NO 71
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 71

His Gly Glu Gly Ser Phe Ser Asp Glu Leu Ser Thr Ile Leu Glu Ser
1               5                   10                  15

Leu Ala Ala Ala Asp Phe Ile Ala Trp Leu Ile Ser Thr Lys Ile Thr
            20                  25                  30

Asp

<210> SEQ ID NO 72
<211> LENGTH: 33
<212> TYPE: PRT
<213> ORGANISM: Artificial sequence

```
<220> FEATURE:
<223> OTHER INFORMATION: Synthetic sequence: GLP-2 analogue

<400> SEQUENCE: 72

His Gly Glu Gly Ser Phe Ser Asp Glu Leu Ser Thr Ile Leu Glu Ala
1               5                   10                  15

Leu Ala Ala Ala Asp Phe Ile Ser Trp Leu Ile Ser Thr Lys Ile Thr
            20                  25                  30

Asp

<210> SEQ ID NO 73
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 73

His Gly Glu Gly Ser Phe Ser Asp Glu Leu Ser Thr Ile Leu Glu Ser
1               5                   10                  15

Leu Ala Ala Ala Asp Phe Ile Ser Trp Leu Ile Ala Thr Lys Ile Thr
            20                  25                  30

Asp

<210> SEQ ID NO 74
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 74

His Gly Glu Gly Ser Phe Ser Asp Glu Leu Ser Thr Ile Leu Glu Ala
1               5                   10                  15

Leu Ala Ala Ser Asp Phe Ile Ala Trp Leu Ile Ser Thr Lys Ile Thr
            20                  25                  30

Asp

<210> SEQ ID NO 75
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 75

His Gly Glu Gly Ser Phe Ser Asp Glu Leu Ala Thr Ile Leu Glu Ser
1               5                   10                  15

Leu Ala Ala Ala Asp Phe Ile Ser Trp Leu Ile Ser Thr Lys Ile Thr
            20                  25                  30

Asp

<210> SEQ ID NO 76
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 76

His Gly Glu Gly Ser Phe Ser Asp Glu Leu Ser Thr Ile Leu Glu Ala
1               5                   10                  15
```

```
Leu Ala Ala Ser Asp Phe Ile Ser Trp Leu Ile Ala Thr Lys Ile Thr
        20                  25                  30

Asp

<210> SEQ ID NO 77
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 77

His Gly Glu Gly Ser Phe Ser Asp Glu Leu Ala Thr Ile Leu Glu Ser
1               5                   10                  15

Leu Ala Ala Ser Asp Phe Ile Ala Trp Leu Ile Ser Thr Lys Ile Thr
        20                  25                  30

Asp

<210> SEQ ID NO 78
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 78

His Gly Glu Gly Ser Phe Ser Asp Glu Leu Ala Thr Ile Leu Glu Ser
1               5                   10                  15

Leu Ala Ala Ser Asp Phe Ile Ser Trp Leu Ile Ala Thr Lys Ile Thr
        20                  25                  30

Asp

<210> SEQ ID NO 79
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 79

His Gly Glu Gly Ser Phe Ser Asp Glu Leu Gly Thr Ile Leu Glu Gly
1               5                   10                  15

Leu Ala Ala Gly Asp Phe Ile Gly Trp Leu Ile Gly Thr Lys Ile Thr
        20                  25                  30

Asp

<210> SEQ ID NO 80
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 80

His Gly Glu Gly Ser Phe Ser Asp Glu Leu Lys Thr Ile Leu Glu Lys
1               5                   10                  15

Leu Ala Ala Lys Asp Phe Ile Lys Trp Leu Ile Lys Thr Lys Ile Thr
        20                  25                  30

Asp

<210> SEQ ID NO 81
<211> LENGTH: 33
```

```
<212> TYPE: PRT
<213> ORGANISM: Artificial sequence
<220> FEATURE:
<223> OTHER INFORMATION: Synthetic sequence: GLP-2 analogue

<400> SEQUENCE: 81

His Gly Glu Gly Ser Phe Ser Asp Glu Leu Glu Thr Ile Leu Glu Glu
1               5                   10                  15

Leu Ala Ala Glu Asp Phe Ile Glu Trp Leu Ile Glu Thr Lys Ile Thr
            20                  25                  30

Asp

<210> SEQ ID NO 82
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 82

His Gly Glu Gly Ser Phe Ser Asp Glu Leu Asp Thr Ile Leu Glu Asp
1               5                   10                  15

Leu Ala Ala Asp Asp Phe Ile Asp Trp Leu Ile Asp Thr Lys Ile Thr
            20                  25                  30

Asp

<210> SEQ ID NO 83
<211> LENGTH: 33
<212> TYPE: PRT
<213> ORGANISM: Artificial sequence
<220> FEATURE:
<223> OTHER INFORMATION: Synthetic sequence: GLP-2 analogue

<400> SEQUENCE: 83

His Gly Glu Gly Ser Phe Ser Asp Glu Leu His Thr Ile Leu Glu His
1               5                   10                  15

Leu Ala Ala His Asp Phe Ile His Trp Leu Ile His Thr Lys Ile Thr
            20                  25                  30

Asp

<210> SEQ ID NO 84
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 84

His Gly Glu Gly Ser Phe Ser Asp Glu Leu Phe Thr Ile Leu Glu Phe
1               5                   10                  15

Leu Ala Ala Phe Asp Phe Ile Phe Trp Leu Ile Phe Thr Lys Ile Thr
            20                  25                  30

Asp Lys Lys Lys Lys Lys Lys
        35

<210> SEQ ID NO 85
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 85
```

-continued

His Gly Glu Gly Ser Phe Ser Asp Glu Leu Val Thr Ile Leu Glu Val
1               5                   10                  15

Leu Ala Ala Val Asp Phe Ile Val Trp Leu Ile Val Thr Lys Ile Thr
            20                  25                  30

Asp Lys Lys Lys Lys Lys Lys
        35

<210> SEQ ID NO 86
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 86

His Gly Glu Gly Ser Phe Ser Asp Glu Leu Ile Thr Ile Leu Glu Ile
1               5                   10                  15

Leu Ala Ala Ile Asp Phe Ile Ile Trp Leu Ile Ile Thr Lys Ile Thr
            20                  25                  30

Asp Lys Lys Lys Lys Lys Lys
        35

<210> SEQ ID NO 87
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 87

His Gly Glu Gly Ser Phe Ser Asp Glu Leu Ile Thr Ile Leu Glu Ile
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 88
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 88

His Gly Glu Gly Ser Phe Ser Asp Glu Leu Val Thr Ile Leu Glu Val
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 89
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 89

His Gly Glu Gly Ser Phe Ser Asp Glu Leu Phe Thr Ile Leu Glu Phe
1               5                   10                  15

Leu Ala Ala Ser Asp Phe Ile Ser Trp Leu Ile Ser Thr Lys Ile Thr

```
                    20                  25                  30

Asp Lys Lys Lys Lys Lys Lys
        35

<210> SEQ ID NO 90
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 90

His Gly Glu Gly Ser Phe Ser Asp Glu Leu Ala Thr Ile Leu Glu Ala
1               5                   10                  15

Leu Ala Ala Gly Asp Phe Ile Gly Trp Leu Ile Gly Thr Lys Ile Thr
            20                  25                  30

Asp Lys Lys Lys Lys Lys Lys
        35

<210> SEQ ID NO 91
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 91

His Gly Glu Gly Ser Phe Ser Asp Glu Leu Leu Thr Ile Leu Glu Leu
1               5                   10                  15

Leu Ala Ala Gly Asp Phe Ile Gly Trp Leu Ile Gly Thr Lys Ile Thr
            20                  25                  30

Asp Lys Lys Lys Lys Lys Lys
        35

<210> SEQ ID NO 92
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 92

His Gly Glu Gly Ser Phe Ser Asp Glu Leu Ile Thr Ile Leu Glu Ile
1               5                   10                  15

Leu Ala Ala Gly Asp Phe Ile Gly Trp Leu Ile Gly Thr Lys Ile Thr
            20                  25                  30

Asp Lys Lys Lys Lys Lys Lys
        35

<210> SEQ ID NO 93
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 93

His Gly Glu Gly Ser Phe Ser Asp Glu Leu Val Thr Ile Leu Glu Val
1               5                   10                  15

Leu Ala Ala Gly Asp Phe Ile Gly Trp Leu Ile Gly Thr Lys Ile Thr
            20                  25                  30

Asp Lys Lys Lys Lys Lys Lys
        35
```

```
<210> SEQ ID NO 94
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 94

His Gly Glu Gly Ser Phe Ser Asp Glu Leu Phe Thr Ile Leu Glu Phe
1               5                   10                  15

Leu Ala Ala Gly Asp Phe Ile Gly Trp Leu Ile Gly Thr Lys Ile Thr
            20                  25                  30

Asp Lys Lys Lys Lys Lys Lys
        35

<210> SEQ ID NO 95
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 95

His Gly Glu Gly Ser Phe Ser Asp Glu Leu Ala Thr Ile Leu Glu Ala
1               5                   10                  15

Leu Ala Ala Ala Asp Phe Ile Ser Trp Leu Ile Ser Thr Lys Ile Thr
            20                  25                  30

Asp Lys Lys Lys Lys Lys Lys
        35

<210> SEQ ID NO 96
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 96

His Gly Glu Gly Ser Phe Ser Asp Glu Leu Ala Thr Ile Leu Glu Ala
1               5                   10                  15

Leu Ala Ala Ser Asp Phe Ile Ser Trp Leu Ile Ala Thr Lys Ile Thr
            20                  25                  30

Asp Lys Lys Lys Lys Lys Lys
        35

<210> SEQ ID NO 97
<211> LENGTH: 39
<212> TYPE: PRT
<213> ORGANISM: Artificial sequence
<220> FEATURE:
<223> OTHER INFORMATION: Synthetic sequence: GLP-2 analogue

<400> SEQUENCE: 97

His Gly Glu Gly Ser Phe Ser Asp Glu Leu Ala Thr Ile Leu Glu Ala
1               5                   10                  15

Leu Ala Ala Ser Asp Phe Ile Ala Trp Leu Ile Ser Thr Lys Ile Thr
            20                  25                  30

Asp Lys Lys Lys Lys Lys Lys
        35

<210> SEQ ID NO 98
<211> LENGTH: 33
```

```
<212> TYPE: PRT
<213> ORGANISM: Artificial sequence
<220> FEATURE:
<223> OTHER INFORMATION: Synthetic sequence: GLP-2 analogue reference
      compound (Gly2)GLP-2

<400> SEQUENCE: 98

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 99
<211> LENGTH: 33
<212> TYPE: PRT
<213> ORGANISM: artificial sequence
<220> FEATURE:
<223> OTHER INFORMATION: Synthetic sequence: GLP-2 analogue

<400> SEQUENCE: 99

His Gly Glu Gly Ser Phe Ser Asp Glu Leu Ala Thr Ile Leu Asp Asn
1               5                   10                  15

Leu Ala Ala Arg Asp Phe Ile Ser Trp Leu Ile Ser Thr Lys Ile Thr
            20                  25                  30

Asp

<210> SEQ ID NO 100
<211> LENGTH: 33
<212> TYPE: PRT
<213> ORGANISM: artificial sequence
<220> FEATURE:
<223> OTHER INFORMATION: Synthetic sequence: GLP-2 analogue

<400> SEQUENCE: 100

His Gly Glu Gly Ser Phe Ser Asp Glu Leu Ser Thr Ile Leu Asp Asn
1               5                   10                  15

Leu Ala Ala Arg Asp Phe Ile Ala Trp Leu Ile Ala Thr Lys Ile Thr
            20                  25                  30

Asp

<210> SEQ ID NO 101
<211> LENGTH: 33
<212> TYPE: PRT
<213> ORGANISM: artificial sequence
<220> FEATURE:
<223> OTHER INFORMATION: Synthetic sequence: GLP-2 analogue

<400> SEQUENCE: 101

His Gly Glu Gly Ser Phe Ser Asp Glu Leu Lys Thr Ile Leu Asp Asn
1               5                   10                  15

Leu Ala Ala Arg Asp Phe Ile Glu Trp Leu Ile Gln Thr Lys Ile Thr
            20                  25                  30

Asp

<210> SEQ ID NO 102
<211> LENGTH: 33
<212> TYPE: PRT
<213> ORGANISM: artificial sequence
<220> FEATURE:
<223> OTHER INFORMATION: Synthetic sequence: GLP-2 analogue

<400> SEQUENCE: 102
```

```
His Gly Glu Gly Ser Phe Ser Asp Glu Leu Asn Thr Ile Leu Asp Asn
1               5                   10                  15

Leu Ala Ala Arg Asp Phe Ile Ser Trp Leu Ile Ser Thr Lys Ile Thr
            20                  25                  30

Asp
```

```
<210> SEQ ID NO 103
<211> LENGTH: 33
<212> TYPE: PRT
<213> ORGANISM: artificial sequence
<220> FEATURE:
<223> OTHER INFORMATION: Synthetic sequence: GLP-2 analogue

<400> SEQUENCE: 103

His Gly Glu Gly Ser Phe Ser Asp Glu Leu Ala Thr Ile Leu Asp Asn
1               5                   10                  15

Leu Ala Ala Arg Asp Phe Ile Ser Trp Leu Ile Ala Thr Lys Ile Thr
            20                  25                  30

Asp
```

```
<210> SEQ ID NO 104
<211> LENGTH: 34
<212> TYPE: PRT
<213> ORGANISM: Artificial Sequence
<220> FEATURE:
<223> OTHER INFORMATION: Synthetic sequence: GLP-2 analogue

<400> SEQUENCE: 104

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys
```

```
<210> SEQ ID NO 105
<211> LENGTH: 33
<212> TYPE: PRT
<213> ORGANISM: Artificial Sequence
<220> FEATURE:
<223> OTHER INFORMATION: Synthetic Construct

<400> SEQUENCE: 105

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ala Thr Lys Ile Thr
            20                  25                  30

Asp
```

```
<210> SEQ ID NO 106
<211> LENGTH: 33
<212> TYPE: PRT
<213> ORGANISM: Artificial Sequence
<220> FEATURE:
<223> OTHER INFORMATION: Synthetic Construct

<400> SEQUENCE: 106

His Gly Glu Gly Ser Phe Ser Asp Glu Leu Leu Thr Ile Leu Glu Leu
1               5                   10                  15

Leu Ala Ala Ser Asp Phe Ile Ser Trp Leu Ile Ser Thr Lys Ile Thr
            20                  25                  30

Asp
```

<210> SEQ ID NO 107
<211> LENGTH: 33
<212> TYPE: PRT
<213> ORGANISM: Artificial Sequence
<220> FEATURE:
<223> OTHER INFORMATION: Synthetic Construct

<400> SEQUENCE: 107

His Gly Glu Gly Ser Phe Ser Asp Glu Leu Phe Thr Ile Leu Glu Phe
1               5                   10                  15

Leu Ala Ala Ser Asp Phe Ile Ser Trp Leu Ile Ser Thr Lys Ile Thr
            20                  25                  30

Asp

<210> SEQ ID NO 108
<211> LENGTH: 33
<212> TYPE: PRT
<213> ORGANISM: Artificial Sequence
<220> FEATURE:
<223> OTHER INFORMATION: Synthetic Construct

<400> SEQUENCE: 108

His Gly Glu Gly Ser Phe Ser Asp Glu Leu Ala Thr Ile Leu Glu Ala
1               5                   10                  15

Leu Ala Ala Ser Asp Phe Ile Ser Trp Leu Ile Ser Thr Lys Ile Thr
            20                  25                  30

Asp

<210> SEQ ID NO 109
<211> LENGTH: 33
<212> TYPE: PRT
<213> ORGANISM: Artificial Sequence
<220> FEATURE:
<223> OTHER INFORMATION: Synthetic Construct

<400> SEQUENCE: 109

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ser Thr Lys Ile Thr
            20                  25                  30

Asp

<210> SEQ ID NO 110
<211> LENGTH: 33
<212> TYPE: PRT
<213> ORGANISM: Artificial Sequence
<220> FEATURE:
<223> OTHER INFORMATION: Synthetic Construct

<400> SEQUENCE: 110

His Gly Glu Gly Ser Phe Ser Asp Glu Leu Ala Thr Ile Leu Glu Ala
1               5                   10                  15

Leu Ala Ala Ala Asp Phe Ile Ser Trp Leu Ile Ala Thr Lys Ile Thr
            20                  25                  30

Asp

<210> SEQ ID NO 111
<211> LENGTH: 33
<212> TYPE: PRT
<213> ORGANISM: Artificial Sequence
<220> FEATURE:
<223> OTHER INFORMATION: Synthetic Construct

```
<400> SEQUENCE: 111

His Gly Glu Gly Ser Phe Ser Asp Glu Leu Ala Thr Ile Leu Glu Ala
1               5                   10                  15

Leu Ala Ala Ser Asp Phe Ile Ala Trp Leu Ile Ala Thr Lys Ile Thr
            20                  25                  30

Asp

<210> SEQ ID NO 112
<211> LENGTH: 33
<212> TYPE: PRT
<213> ORGANISM: Artificial Sequence
<220> FEATURE:
<223> OTHER INFORMATION: Synthetic Construct

<400> SEQUENCE: 112

His Gly Glu Gly Ser Phe Ser Asp Glu Leu Ser Thr Ile Leu Glu Ser
1               5                   10                  15

Leu Ala Ala Ser Asp Phe Ile Ser Trp Leu Ile Ser Thr Lys Ile Thr
            20                  25                  30

Asp

<210> SEQ ID NO 113
<211> LENGTH: 33
<212> TYPE: PRT
<213> ORGANISM: Artificial Sequence
<220> FEATURE:
<223> OTHER INFORMATION: Synthetic Construct

<400> SEQUENCE: 113

His Gly Glu Gly Ser Phe Ser Asp Glu Leu Ser Thr Ile Leu Glu Ala
1               5                   10                  15

Leu Ala Ala Ala Asp Phe Ile Ala Trp Leu Ile Ala Thr Lys Ile Thr
            20                  25                  30

Asp

<210> SEQ ID NO 114
<211> LENGTH: 33
<212> TYPE: PRT
<213> ORGANISM: Artificial Sequence
<220> FEATURE:
<223> OTHER INFORMATION: Synthetic Construct

<400> SEQUENCE: 114

His Gly Glu Gly Ser Phe Ser Asp Glu Leu Ser Thr Ile Leu Glu Ser
1               5                   10                  15

Leu Ala Ala Ala Asp Phe Ile Ala Trp Leu Ile Ala Thr Lys Ile Thr
            20                  25                  30

Asp

<210> SEQ ID NO 115
<211> LENGTH: 33
<212> TYPE: PRT
<213> ORGANISM: Artificial Sequence
<220> FEATURE:
<223> OTHER INFORMATION: Synthetic Construct

<400> SEQUENCE: 115

His Gly Glu Gly Ser Phe Ser Asp Glu Leu Ala Thr Ile Leu Glu Ser
1               5                   10                  15

Leu Ala Ala Ala Asp Phe Ile Ser Trp Leu Ile Ala Thr Lys Ile Thr
            20                  25                  30
```

Asp

<210> SEQ ID NO 116
<211> LENGTH: 33
<212> TYPE: PRT
<213> ORGANISM: Artificial Sequence
<220> FEATURE:
<223> OTHER INFORMATION: Synthetic Construct

<400> SEQUENCE: 116

His Gly Glu Gly Ser Phe Ser Asp Glu Leu Ser Thr Ile Leu Glu Ala
1               5                   10                  15

Leu Ala Ala Ser Asp Phe Ile Ser Trp Leu Ile Ser Thr Lys Ile Thr
            20                  25                  30

Asp

<210> SEQ ID NO 117
<211> LENGTH: 33
<212> TYPE: PRT
<213> ORGANISM: Artificial Sequence
<220> FEATURE:
<223> OTHER INFORMATION: Synthetic Construct

<400> SEQUENCE: 117

His Gly Glu Gly Ser Phe Ser Asp Glu Leu Ala Thr Ile Leu Glu Ser
1               5                   10                  15

Leu Ala Ala Ser Asp Phe Ile Ser Trp Leu Ile Ser Thr Lys Ile Thr
            20                  25                  30

Asp

<210> SEQ ID NO 118
<211> LENGTH: 39
<212> TYPE: PRT
<213> ORGANISM: Artificial Sequence
<220> FEATURE:
<223> OTHER INFORMATION: Synthetic Construct

<400> SEQUENCE: 118

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ala Thr Lys Ile Thr
            20                  25                  30

Asp Lys Lys Lys Lys Lys Lys
            35

<210> SEQ ID NO 119
<211> LENGTH: 39
<212> TYPE: PRT
<213> ORGANISM: Artificial Sequence
<220> FEATURE:
<223> OTHER INFORMATION: Synthetic Construct

<400> SEQUENCE: 119

His Gly Glu Gly Ser Phe Ser Asp Glu Leu Leu Thr Ile Leu Glu Leu
1               5                   10                  15

Leu Ala Ala Leu Asp Phe Ile Leu Trp Leu Ile Leu Thr Lys Ile Thr
            20                  25                  30

Asp Lys Lys Lys Lys Lys Lys
            35

<210> SEQ ID NO 120
<211> LENGTH: 39
<212> TYPE: PRT

```
<213> ORGANISM: Artificial Sequence
<220> FEATURE:
<223> OTHER INFORMATION: Synthetic Construct

<400> SEQUENCE: 120

His Gly Glu Gly Ser Phe Ser Asp Glu Leu Leu Thr Ile Leu Glu Leu
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 121
<211> LENGTH: 39
<212> TYPE: PRT
<213> ORGANISM: Artificial Sequence
<220> FEATURE:
<223> OTHER INFORMATION: Synthetic Construct

<400> SEQUENCE: 121

His Gly Glu Gly Ser Phe Ser Asp Glu Leu Ala Thr Ile Leu Glu Ala
1               5                   10                  15

Leu Ala Ala Ser Asp Phe Ile Ser Trp Leu Ile Ser Thr Lys Ile Thr
            20                  25                  30

Asp Lys Lys Lys Lys Lys Lys
        35

<210> SEQ ID NO 122
<211> LENGTH: 39
<212> TYPE: PRT
<213> ORGANISM: Artificial Sequence
<220> FEATURE:
<223> OTHER INFORMATION: Synthetic Construct

<400> SEQUENCE: 122

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ser Thr Lys Ile Thr
            20                  25                  30

Asp Lys Lys Lys Lys Lys Lys
        35

<210> SEQ ID NO 123
<211> LENGTH: 39
<212> TYPE: PRT
<213> ORGANISM: Artificial Sequence
<220> FEATURE:
<223> OTHER INFORMATION: Synthetic Construct

<400> SEQUENCE: 123

His Gly Glu Gly Ser Phe Ser Asp Glu Leu Ala Thr Ile Leu Glu Ala
1               5                   10                  15

Leu Ala Ala Ala Asp Phe Ile Ser Trp Leu Ile Ala Thr Lys Ile Thr
            20                  25                  30

Asp Lys Lys Lys Lys Lys Lys
        35

<210> SEQ ID NO 124
<211> LENGTH: 39
<212> TYPE: PRT
<213> ORGANISM: Artificial Sequence
<220> FEATURE:
<223> OTHER INFORMATION: Synthetic Construct
```

```
<400> SEQUENCE: 124

His Gly Glu Gly Ser Phe Ser Asp Glu Leu Ala Thr Ile Leu Glu Ala
1               5                   10                  15

Leu Ala Ala Ser Asp Phe Ile Ala Trp Leu Ile Ala Thr Lys Ile Thr
            20                  25                  30

Asp Lys Lys Lys Lys Lys
        35

<210> SEQ ID NO 125
<211> LENGTH: 33
<212> TYPE: PRT
<213> ORGANISM: Artificial Sequence
<220> FEATURE:
<223> OTHER INFORMATION: Synthetic Construct

<400> SEQUENCE: 125

His Gly Glu Gly Ser Phe Ser Asp Glu Leu Ala Thr Ile Leu Glu Ala
1               5                   10                  15

Leu Ala Ala Ala Asp Phe Ile Ala Trp Leu Ile Ala Thr Lys Ile Thr
            20                  25                  30

Asp

<210> SEQ ID NO 126
<211> LENGTH: 33
<212> TYPE: PRT
<213> ORGANISM: Artificial Sequence
<220> FEATURE:
<223> OTHER INFORMATION: Synthetic Construct

<400> SEQUENCE: 126

His Gly Glu Gly Ser Phe Ser Asp Glu Leu Ala Thr Ile Leu Asp Asn
1               5                   10                  15

Leu Ala Ala Arg Asp Phe Ile Ser Trp Leu Ile Ser Thr Lys Ile Thr
            20                  25                  30

Asp

<210> SEQ ID NO 127
<211> LENGTH: 33
<212> TYPE: PRT
<213> ORGANISM: Artificial Sequence
<220> FEATURE:
<223> OTHER INFORMATION: Synthetic Construct

<400> SEQUENCE: 127

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 128
<211> LENGTH: 33
<212> TYPE: PRT
<213> ORGANISM: Artificial Sequence
<220> FEATURE:
<223> OTHER INFORMATION: Synthetic Construct

<400> SEQUENCE: 128

His Gly Glu Gly Ser Phe Ser Asp Glu Leu Ser Thr Ile Leu Glu Ser
1               5                   10                  15

Leu Ala Ala Ser Asp Phe Ile Ser Trp Leu Ile Ser Thr Lys Ile Thr
            20                  25                  30
```

```
<210> SEQ ID NO 129
<211> LENGTH: 33
<212> TYPE: PRT
<213> ORGANISM: Artificial Sequence
<220> FEATURE:
<223> OTHER INFORMATION: Synthetic Construct

<400> SEQUENCE: 129

His Gly Glu Gly Ser Phe Ser Asp Glu Leu Ala Thr Ile Leu Glu Ala
 1               5                  10                  15

Leu Ala Ala Ala Asp Phe Ile Ala Trp Leu Ile Ala Thr Lys Ile Thr
             20                  25                  30

Asp

<210> SEQ ID NO 130
<211> LENGTH: 33
<212> TYPE: PRT
<213> ORGANISM: Artificial Sequence
<220> FEATURE:
<223> OTHER INFORMATION: Synthetic Construct

<400> SEQUENCE: 130

His Gly Glu Gly Ser Phe Ser Asp Glu Leu Glu Thr Ile Leu Glu Glu
 1               5                  10                  15

Leu Ala Ala Glu Asp Phe Ile Glu Trp Leu Ile Glu Thr Lys Ile Thr
             20                  25                  30

Asp
```

SELECTIVE GLUCAGON-LIKE-PEPTIDE-2 (GLP-2) ANALOGUES

CROSS-REFERENCE TO RELATED APPLICATIONS

This application is the national stage of International Application No. PCT/GB2007/004273, filed Nov. 8, 2007, which claims benefit of U.S. Application No. 60/859,313, filed Nov. 15, 2006, and Danish Application No. PA 2006 01456, filed Nov. 8, 2006.

FIELD OF THE INVENTION

The present invention relates to selective glucagon-like-peptide-2 (GLP-2) analogues and their medical use, for example in the prophylaxis or treatment of stomach and bowel-related disorders and for ameliorating the gastro-intestinal associated side effects of chemotherapy and/or radiation therapy.

BACKGROUND OF THE INVENTION

GLP-2 is a 33-amino-acid peptide derived from specific posttranslational processing of proglucagon in the enteroendocrine L cells of the intestine and in specific regions of the brainstem. It is co-secreted together with glucagon-like peptide 1 (GLP-1), oxyntomodulin and glicentin, in response to nutrient ingestion.

GLP-2 induces significant growth of the small intestinal mucosal epithelium via the stimulation of stem cell proliferation in the crypts and inhibition of apoptosis on the villi (Drucker et al. Proc Natl Acad Sci USA. 1996, 93:7911-6). GLP-2 also has growth effects on the colon. GLP-2 also inhibits gastric emptying and gastric acid secretion (Wojdemann et al. J Clin Endocrinol Metab. 1999, 84:2513-7), enhances intestinal barrier function (Benjamin et al. Gut. 2000, 47:112-9.), stimulates intestinal hexose transport via the upregulation of glucose transporters (Cheeseman, .Am J. Physiol. 1997, R1965-71.), and increases intestinal blood flow (Guan et al. Gastroenterology. 2003, 125, 136-47).

GLP-2 binds to a single G protein-coupled receptor belonging to the class II glucagon secretin family. The GLP-2 receptor is expressed in the small intestine, colon and stomach, sites that are known to be responsive to GLP-2 (Yusta et al. Gastroenterology. 2000, 119: 744-55). However, the target cell for GLP-2 receptor stimulation in the gastrointestinal tract remains unclear and the downstream intracellular mediators coupled to the GLP-2 receptor are poorly understood.

The demonstrated specific and beneficial effects of GLP-2 in the small intestine have raised much interest as to the use of GLP-2 in the treatment of intestinal disease or injury (Sinclair and Drucker, Physiology 2005: 357-65). Furthermore GLP-2 has been shown to prevent or reduce mucosal epithelial damage in a wide number of preclinical models of gut injury, including chemotherapy-induced enteritis, ischemia-reperfusion injury, dextran sulfate-induced colitis and genetic models of inflammatory bowel disease (Sinclair and Drucker Physiology 2005: 357-65).

Further, the expression of the GLP-2R mRNA in the stomach, (Yusta et al., 2000) together with the observation that GLP-2 reduces gastric motility and gastric acid secretion (Meier et al., 2006) provides ample evidence that the stomach is either directly or indirectly responsive to GLP-2.

Nevertheless the use of GLP-2 or analogues of GLP-2 in conditions characterised by damage to the gastric lining has not yet being explored.

GLP-2 is secreted as a 33 amino acid peptide with the following sequence H-His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-OH (SEQ ID NO:1). It is rapidly cleaved at the Alanine (A) in position 2 of the $NH_2$ terminus to the inactive human GLP-2 (3-33) by the enzyme DPP IV. This rapid enzymatic degradation of GLP-2 (1-33), in addition to renal clearance result in a half life of about 7 minutes for the peptide (Tavares et al., Am. J. Physiol. Endocrinol. Metab. 278:E134-E139, 2000).

In U.S. Pat. No. 5,994,500 (Drucker et al.) describes antagonists of GLP-2 and their effects on the growth of gastrointestinal tissue. It is suggested that the antagonists are formulated as pharmaceuticals to be used in the treatment of hyperplasia or to induce hypoplasia. In U.S. Pat. No. 5,994,500 the structure of mammalian GLP-2 has been altered by mutations, such as substitutions and deletions.

U.S. Pat. No. 6,184,208; U.S. Pat. No. 5,789,379 and U.S. Pat. No. 6,184,201 disclose GLP-2 analogues and their medical uses. These analogues are all obtained by substitutions and/or deletions of human GLP-2.

DaCambra et al. (Biochemistry 2000, 39, 8888-8894) describe the structural determinants for activity of GLP-2. Examples of such determinants are Phe6 and Thr5, which are referred to as crucial for GLP-2 receptor binding and activation.

In WO 97/39031 the GLP-2 analogue, [Gly2]GLP-2 is disclosed. Here the alanine in position 2 has been replaced with glycine to make the peptide resistant to DPP IV cleavage. The replacement of alanine is shown to increase the stability and potency of the peptide. The patent application describes how the GLP-2 analogue may be used against diseases associated with inflammation and destruction of the intestinal epithelial mucosa. These include massive small intestine resection, inflammatory bowel disease, chemotherapy and/or radiation induced enteritis and ischemic injury.

WO 02/066511 describes GLP-2 analogues having an extended half-life in vivo and their use as medicaments in the treatment of gastrointestinal disorders, such as inflammatory bowel diseases.

WO 01/41779 describes the use of h[Gly2]GLP-2 as a pretreatment for inhibiting chemotherapy induced apoptosis and promoting small intestinal epithelial cell survival.

All references cited herein are expressly incorporated by reference in their entirety.

The use of GLP-2 or analogues of GLP-2 in the treatment of various diseases has been proposed by many scientists. However, there is still a need for improved and small intestine selective GLP-2 analogues.

SUMMARY OF THE INVENTION

Broadly, the present invention concerns GLP-2 analogues which comprise one or more substitutions as compared to wild-type GLP-2 and which may have the property of an increased small intestine versus colon selectivity, an improved biological activity in vivo and/or improved chemical stability, e.g. as assessed in vitro stability assays. More particularly, preferred GLP-2 analogues of the present invention comprise non-conservative substitutions at one or more of positions 8, 11, 12, 13, 16, 17, 18, 20, 21, 24 and/or 28 of the wild-type GLP-2 sequence, optionally in combination with further conservative or non-conservative substitutions at position 2 (as mentioned in the introduction) and one or more of positions 3, 5, 7 and 10, and/or a substitution or deletion of one or more of amino acids corresponding to positions 31 to 33 of the wild-type GLP-2 sequence and, optionally, the addition of an N-terminal or C-terminal stabilizing peptide sequence. In addition the GLP-2 analogues of the invention may comprise conservative substitutions of one or more amino acids corresponding to positions 9, 14, and 15. As well as providing GLP-2 analogues that may have improved chemical stability and/or biological activity, the present invention also relates to providing compounds that have preferential intestinal growth promoting activity in the small intestine compared to the colon and vice versa, in particular by including modification at one or more of positions Asn11 and/or Asn16 and/or Arg20 and/or Asn24 and/or Gln28 of wild-type GLP-2.

Accordingly, in one aspect, the present invention provides a GLP-2 analogue which is represented by the general Formula I:

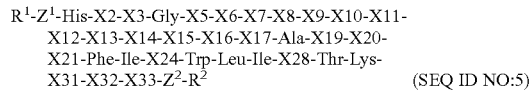

(SEQ ID NO:3)

wherein:
$R^1$ is hydrogen, $C_{1-4}$ alkyl (e.g. methyl), acetyl, formyl, benzoyl or trifluoroacetyl;
X2 is Gly, Ala or Sar;
X3 is Glu or Asp;
X5 is Ser or Thr;
X6 is Phe or Pro or a conservative substitution;
X7 is Ser or Thr;
X8 is Asp or Ser or a conservative substitution;
X9 is Glu or Asp or a conservative substitution;
X10 is Met, Leu, Nle or an oxidatively stable Met-replacement amino acid;
X11 is Y1;
X12 is Thr or Lys or a conservative substitution;
X13 is Ile, Glu or Gln or a conservative substitution;
X14 is Leu, Met or Nle or a conservative substitution;
X15 is Asp or Glu or a conservative substitution;
X16 is Y2;
X17 is Leu or Glu or a conservative substitution;
X18 is Ala or Aib or a non-conservative substitution;
X19 is Ala or Thr or a conservative substitution;
X20 is Y3;
X21 is Asp or Ile or a conservative substitution;
X24 is Y4;
X28 is Y5;
X31 is Pro, Ile or deleted;
X32 is Thr or deleted;
X33 is Asp, Asn or deleted;
$R^2$ is $NH_2$ or OH;
wherein
$Z^1$ and $Z^2$ are independently absent or a peptide sequence of 1-10 amino acid units selected from the group consisting of Ala, Leu, Ser, Thr, Tyr, Asn, Gln, Asp, Glu, Lys, Arg, His, Met and Orn; and the hydrophaticity profile (HPP) of the residues X11, X16, X20, X24, X28 of formula I calculated as

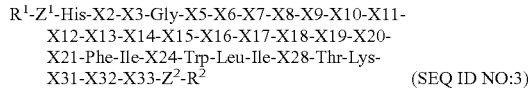

wherein
$Y_1, Y_2, Y_4$, and $Y_5$ can individually be selected from the group consisting of Asn, Asp, Glu, Gln, Lys, His, Arg, Ala, Ser, Thr, Pro, Gly, Leu, Ile, Val, Met or Phe; and
$Y_3$ can be selected from the group consisting of Asn, Asp, Glu, Gln, His, Arg, Ala, Ser, Thr, Pro, Gly, Leu, Ile, Val, Met or Phe;

with the proviso that when X20 is Arg then X11 is Ser, X16 is Ala, X24 is Ala, X28 is Ala and Z2 is Lys, or a pharmaceutically acceptable salt or derivative thereof.

In one embodiment the invention comprises a glucagon-like peptide 2 (GLP-2) analogue as described above wherein HPP is ≥−4

In another embodiment the invention comprises a glucagon-like peptide 2 (GLP-2) analogue as described above wherein HPP≥0

In another aspect, the present invention provides a GLP-2 analogue which is represented by general Formula II:

R¹-Z¹-His-X2-X3-Gly-X5-X6-X7-X8-X9-X10-X11-
X12-X13-X14-X15-X16-X17-Ala-X19-X20-
X21-Phe-Ile-X24-Trp-Leu-Ile-X28-Thr-Lys-
X31-X32-X33-Z²-R²     (SEQ ID NO:5)

wherein:
$R^1$ is hydrogen, $C_{1-4}$ alkyl (e.g. methyl), acetyl, formyl, benzoyl or trifluoroacetyl
X2 is Gly, Ala or Sar
X3 is Glu or Asp
X5 is Ser or Thr
X6 is Phe or Pro
X7 is Ser or Thr
X8 is Asp or Ser
X9 is Glu or Asp
X10 is Met, Leu, Nle or an oxidatively stable Met-replacement amino acid
X11 is Asn, Ala, Glu, Gly, Ile, Leu, Lys, Met, Phe Ser, Thr or Val
X12 is Thr or Lys
X13 is Ile, Glu or Gln
X14 is Leu, Met or Nle
X15 is Asp or Glu
X16 is Asn, Ala, Glu, Gly, Ile, Leu, Lys, Met, Phe Ser, Thr or Val
X17 is Leu or Glu
X18 is Ala or Aib
X19 is Ala or Thr
X20 is Asn, Arg, Ala, Glu, Gly, Ile, Leu, Met, Phe Ser, Thr or Val
X21 is Asp or Ile
X24 is Asn, Ala, Glu, Gly, Ile, Leu, Lys, Met, Phe Ser, Thr or Val
X28 is Asn, Ala, Glu, Gly, Ile, Leu, Lys, Met, Phe Ser, Thr or Val
X31 is Pro, Ile or deleted
X32 is Thr or deleted
X33 is Asp, Asn or deleted
$R^2$ is $NH_2$ or OH;
$Z^1$ and $Z^2$ are independently absent or a peptide sequence of 1-10 amino acid units selected from the group consisting of Ala, Leu, Ser, Thr, Tyr, Asn, Gln, Asp, Glu, Lys, Arg, His, Met and Orn;
or a pharmaceutically acceptable salt or derivative thereof;
with the proviso that when X20 is Arg then X11 is Ser, X16 is Ala, X24 is Ala, X28 is Ala and Z2 is Lys.

In one embodiment the invention comprises a GLP-2 analogue as described above wherein
X11 is Ala, Gly, Ile, Leu, Phe Ser, Thr or Val
X16 is Ala, Gly, Ile, Leu, Phe Ser, Thr or Val
X20 is Ala, Gly, Ile, Leu, Phe Ser, Thr or Val
X24 is Ala, Gly, Ile, Leu, Phe Ser, Thr or Val
X28 is Ala, Gly, Ile, Leu, Phe Ser, Thr or Val.

In another embodiment the invention comprises a GLP-2 analogue as described above wherein
X11 is Ala, Ile, Leu, Phe or Val;
X16 is Ala, Ile, Leu, Phe or Val X20 is Ala, Ile, Leu, Phe or Val
X24 is Ala, Ile, Leu, Phe or Val
X28 is Ala, Ile, Leu, Phe or Val.

In yet another embodiment the invention comprises a GLP-2 analogue as described above wherein the GLP-2 analogue has at least 60% amino acid sequence identity to wild-type GLP-2 (1-33) and has the biological activity of causing an increase in intestinal mass in vivo.

In a further embodiment the invention comprises an GLP-2 analogue with more than one of the substitutions (i.e. more than substitution relative to the wild type sequence given above) at positions X11, X16, X20, X24 and/or X28 and/or one of more of said substitutions in combination with one or more substitutions at positions X3, X5, X7 and/or X10.

In still another embodiment the invention comprises an GLP-2 analogue with substitutions at position X10 is Leu, Nle, or an oxidatively stable Met-replacement amino acid, such as Met(O) or Met(O)$_2$. Thus, additionally or alternatively to the substitutions already mentioned, the GLP-2 analogue may have Leu, Nle, or an oxidatively stable Met-replacement amino acid, such as Met(O) or Met(O)$_2$ at position X10.

In some embodiments of the present invention, the GLP-2 analogue has at least 60% amino acid sequence identity to wild-type GLP-2 (1-33) having the sequence set out in the background of the application, more preferably at least 63% sequence identity, more preferably at least 66% sequence identity and still more preferably at least 69% sequence identity.

"Percent (%) amino acid sequence identity" with respect to the GLP-2 polypeptide sequences is defined as the percentage of amino acid residues in a candidate sequence that are identical with the amino acid residues in the wild-type GLP-2 sequence, after aligning the sequences and introducing gaps, if necessary, to achieve the maximum percent sequence identity, and not considering any conservative substitutions as part of the sequence identity. Sequence alignment can be carried out by the skilled person using techniques well known in the art for example using publicly available software such as BLAST, BLAST2 or Align software, see: Altschul et al (Methods in Enzymology, 266:460-480 (1996) and Pearson et al (Genomics, 46, 24, 36, 1997).

The percentage sequence identities used herein and in accordance with the present invention are determined using these programe with their default settings. More generally, the skilled person can readily determine appropriate parameters for determining alignment, including any algorithms needed to achieve maximal alignment over the full length of the sequences being compared.

In another embodiment of the present invention the GLP-2 analogue as described above comprises more than one of the substitutions (i.e. more than one substitution relative to the wild type sequence given above) at positions X3, X5, X7, X11, X16, X20, X24, X28, X31, X32 and/or X33.

In still another embodiment of the present invention the GLP-2 analogue as described above comprises one or more of substitutions selected from X11, X16, X20, X24, X28 is Ile, Ala, Leu, Phe or Val; and the amino acid residues in positions X31, X32 and X33 are optionally deleted; or a pharmaceutically acceptable salt or derivative thereof.

In still another embodiment of the present invention the GLP-2 analogue as described above comprises a substitution (i.e. a substitution relative to the wild type sequence given above) at one or more of positions X11, X16, X20, X24 and/or X28.

In a preferred embodiment of the present invention the GLP-2 analogue as described above is disclosed in Table 1 or Table 2 herein or a pharmaceutically acceptable salt or derivative thereof.

In a preferred embodiment of the present invention the GLP-2 analogue is defined by the general formula III:

R1-His-Gly-Glu-Gly-Ser-Phe-Ser-X8-Glu-Leu-X11-
Thr-Ile-Leu-X15-X16-Leu-Ala-Ala-X20-Asp-
Phe-Ile-X24-Trp-Leu-Ile-X28-Thr-Lys-Ile-Thr-
Asp-NH$_2$;  (SEQ ID NO:6)

wherein
R$^1$ is hydrogen, C$_{1-4}$ alkyl (e.g. methyl), acetyl, formyl, benzoyl or trifluoroacetyl
X8 is Asp or Ser, preferably Asp;
X11 is Ser, Ala, Glu, Lys or Asn;
X15 is Glu or Asp, preferably Glu;
X16 is Ser, Ala or Glu;
X20 is Ser, Ala, or Glu;
X24 is Ser, Ala or Glu; and
X28 is Ser, Ala, Gln or Glu;
or a pharmaceutically acceptable salt or derivative thereof.

Interesting compounds of the invention (formula I) are described in the following table, where said compounds may be modified at the N-terminus as described for R$^1$ in formula III and including a pharmaceutically acceptable salt or derivative thereof:

| | |
|---|---|
| ZP2263 (SEQ ID NO: 7) | His-Gly-Glu-Gly-Ser-Phe-Ser-Asp-Glu-Leu-Ser-Thr-Ile-Leu-Glu-Ser-Leu-Ala-Ala-Ser-Asp-Phe-Ile-Ser-Trp-Leu-Ile-Ser-Thr-Lys-Ile-Thr-Asp-NH$_2$ |
| ZP2264 (SEQ ID NO: 8) | His-Gly-Glu-Gly-Ser-Phe-Ser-Asp-Glu-Leu-Ala-Thr-Ile-Leu-Glu-Ala-Leu-Ala-Ala-Ala-Asp-Phe-Ile-Ala-Trp-Leu-Ile-Ala-Thr-Lys-Ile-Thr-Asp-NH$_2$ |
| ZP2266 (SEQ ID NO: 9) | His-Gly-Glu-Gly-Ser-Phe-Ser-Asp-Glu-Leu-Glu-Thr-Ile-Leu-Glu-Glu-Leu-Ala-Ala-Glu-Asp-Phe-Ile-Glu-Trp-Leu-Ile-Glu-Thr-Lys-Ile-Thr-Asp-NH$_2$ |
| ZP2267 (SEQ ID NO: 10) | His-Gly-Glu-Gly-Ser-Phe-Ser-Asp-Glu-Leu-Ser-Thr-Ile-Leu-Glu-Ser-Leu-Ala-Ala-Ala-Asp-Phe-Ile-Ala-Trp-Leu-Ile-Ala-Thr-Lys-Ile-Thr-Asp-NH$_2$ |
| ZP2268 (SEQ ID NO: 11) | His-Gly-Glu-Gly-Ser-Phe-Ser-Asp-Glu-Leu-Ala-Thr-Ile-Leu-Glu-Ala-Leu-Ala-Ala-Ser-Asp-Phe-Ile-Ser-Trp-Leu-Ile-Ser-Thr-Lys-Ile-Thr-Asp-NH$_2$ |
| ZP2269 (SEQ ID NO: 12) | His-Gly-Glu-Gly-Ser-Phe-Ser-Asp-Glu-Leu-Lys-Thr-Ile-Leu-Glu-Ser-Leu-Ala-Ala-Ala-Asp-Phe-Ile-Glu-Trp-Leu-Ile-Gln-Thr-Lys-Ile-Thr-Asp-NH$_2$ |
| ZP2270 (SEQ ID NO: 13) | His-Gly-Glu-Gly-Ser-Phe-Ser-Asp-Glu-LeuN-Thr-Ile-Leu-Glu-Ser-Leu-Ala-Ala-Ser-Asp-Phe-Ile-Ser-Trp-Leu-Ile-Ser-Thr-Lys-Ile-Thr-Asp-NH$_2$ |

| | |
|---|---|
| ZP2272 (SEQ ID NO: 14) | His-Gly-Glu-Gly-Ser-Phe-Ser-Asp-Glu-Leu-Ala-Thr-Ile-Leu-Glu-Ser-Leu-Ala-Ala-Ala-Asp-Phe-Ile-Ser-Trp-Leu-Ile-Ala-Thr-Lys-Ile-Thr-Asp-NH$_2$ |
| ZP2242 (SEQ ID NO: 15) | His-Gly-Glu-Gly-Ser-Phe-Ser-Ser-Glu-Leu-Ser-Thr-Ile-Leu-Asp-Ala-Leu-Ala-Ala-Arg-Asp-Phe-Ile-Ala-Trp-Leu-Ile-Ala-Thr-Lys-Ile-Thr-Asp-Lys-OH |

Further compounds of the invention are shown in Table 1, below.

The present invention provides compounds that have preferential growth promoting activity in the small intestine compared to the colon. In particular, the experiments described herein show that certain substitutions at positions X11 and/or X16 and/or Asn20 and/or X24 and/or X28 of wild-type GLP-2 provide a preferential increase of the small intestine weight when administered to test animals compared to the increase in colon mass. These findings mean that the exemplified compounds may be useful for treating conditions where it is advantageous to have an increased growth promoting effect in the small intestine, while having a lower effect on the colon or in conditions where small intestine is damaged and the colon intact.

Thus, compounds that are preferred for causing growth of the small intestine typically comprise one or more substitutions (i.e. relative to the wild type sequence given above) at positions 11, 16, 20, 24 and/or X28 of wild-type GLP-2. Such compounds may selectively cause growth of the small intestine rather than the colon. They may therefore be used for conditions affecting or related to the small intestine.

Preferably, such small intestine-selective compounds comprise substitutions (i.e. relative to the wild type sequence given above) at more than one of positions X11, X16, X20, X24, and/or X28. Thus the small-intestine-selective compounds may comprise more than one of the substitutions where X11 is Ser, X16 is Ala, X20, X24 is Ala, X28 is Ala, X31 is Ile, X32 is Thr and X33 is Asp. The amino acid residues in positions X31, X32 and X33 may optionally be deleted.

In small intestine-selective compounds, each of X11, X16, X20, X24 and X28 may independently be Ala, Ser, Gly or Thr.

For example, each of X11 and X16 may independently be Ala or Ser, and X20, X24 and X28 may independently be Ala, Ser, Gly or Thr.

For example, X11 and X16 may both be Ala, and X20, X24 and X28 may independently be Ala, Ser, Gly or Thr.

For example, X11 and X16 may both be Ala, and X20, X24 and X28 may all independently be Ala or Ser.

It will be appreciated that other residue combinations falling outside these general criteria may also provide small intestine selectivity.

Preferred combinations of residues at positions X11, X16, X20, X24 and X28 include Ser/Ser/Ser/Ser/Ser; Ala/Ala/Ser/Ser/Ser, Ala/Ala/Ala/Ala/Ser, Ser/Ala/Ser/Ser/Ser, Ala/Ser/Ser/Ser/Ser; Ala/Ala/Ala/Ser/Ala; Ala/Ala/Ser/Ala/Ala; Ser/Ala/Ala/Ala/Ala; Ser/Ala/Arg/Ala/Ala; Ala/Ser/Ala/Ser/Ala; Ala/Ala/Ala/Ala/Ala.

Exemplified compounds preferentially stimulating epithelial growth in the small intestine include ZP2264, ZP2268, ZP2242, ZP2272, ZP2411, ZP2380, ZP2384, ZP2398, ZP2417, ZP2423, ZP2385, ZP2399, ZP2418, ZP2381, ZP2420 and ZP2397.

The invention also extends to compounds having preferential growth promoting activity in the stomach compared to colon. They may therefore be used for conditions affecting or related to the stomach.

Preferably, such stomach-selective compounds comprise substitutions (i.e. relative to the wild type sequence given above) at more than one of positions X11, X16, X20, X24, and/or X28. The amino acid residues in positions X31, X32 and X33 may optionally be deleted.

For example, in stomach-selective compounds,
X11 may be Leu, Phe or Lys.
X16 may be Leu, Phe or Lys.
X20 may be Ala or Ser.
X24 may be Ala, Ser or Lys.
X28 may be Ala, Ser or Lys.

For example, X11 and X16 may independently be Leu or Phe, X24 and X28 may independently be Lys or Ser, and X20 may be Ser.

For example, X11 and X16 may independently be Leu or Phe, and X20, X24 and X28 may be Ser.

It will be appreciated that other residue combinations falling outside these general criteria may also provide stomach selectivity.

Preferred combinations of residues at positions X11, X16, X20, X24 and X28 include Lys/Lys/Lys/Lys/Lys; Phe/Phe/Ser/Ser/Ser; Leu/Leu/Ala/Ala/Ala; and Leu/Leu/Ser/Ser/Ser.

Exemplified compounds preferentially stimulating epithelial growth in the stomach include ZP2400, ZP2412, ZP2396, ZP2395, ZP2394 and ZP2401.

Preferably, the GLP-2 analogue maintains an observed purity of at least 70% relative to the initial purity in at least one of the degradation tests described in Example 7 below. Additionally or alternatively, it may maintain an observed purity of at least 60% relative to initial purity in a solution of HCl 0.1 M after 12 days. Additionally or alternatively it may maintain an observed purity of at least 70% relative to initial purity in a solution of NH4HCO3 0.1 M after 6 days.

Another aspect of the present invention relates to GLP-2 analogues as described above having at least an EC50 of 1 nM and thus are defined as GLP-2 agonists. The present compounds were analysed as described in example 9. In FIG. 5 the EC50 of ZP2264 is shown as an example of an GLP-2 agonist.

In a further aspect, the present invention provides a composition comprising a GLP-2 analogue as defined herein, or a salt or derivative thereof, in admixture with a carrier. In preferred embodiments, the composition is a pharmaceutically acceptable composition and the carrier is a pharmaceutically acceptable carrier. The GLP-2 peptide analogue may be a pharmaceutically acceptable acid addition salt of the GLP-2 analogue.

In one embodiment the invention relates to the use of a GLP-2 analogue as defined herein as a pharmaceutical composition, which is formulated as a liquid suitable for administration by injection or infusion, or which is formulated to cause slow release of said GLP-2 analogue.

In a further aspect, the present invention provides a GLP-2 analogue as defined herein, or a salt thereof, for use in therapy.

The present invention further provides the use of a GLP-2 analogue as described above for the preparation of a medicament for the treatment and/or prevention of a stomach and bowel-related disorder.

In a preferred embodiment the present invention relates to the use of a GLP-2 analogue, or a salt or derivative thereof for the preparation of a medicament for the treatment and/or prevention of stomach and bowel-related disorders, such as the treatment of neonatals with compromised intestine function, osteoporosis, and DPP-IV (dipeptidylpeptidase-IV) mediated conditions. By way of example, the stomach and bowel-related disorders include ulcers, Zollinger-Ellison syndrome, gastritis, digestion disorders, malabsorption syndromes, short-gut syndrome, cul-de-sac syndrome, inflammatory bowel disease (Crohns disease and Ulcerative colitis), celiac sprue (for example arising from gluten induced enteropathy or celiac disease), tropical sprue, hypogammaglobulinemic sprue, enteritis, irritable bowel syndrome associated with diarrhea, small intestine damage and short bowel syndrome.

In another preferred embodiment the present invention relates to the use of a GLP-2 analogue as described above wherein said stomach and bowel-related disorder is radiation enteritis, infectious or post-infectious enteritis, or small intestinal damage due to toxic or other chemotherapeutic agents.

The present invention further provides the use of a GLP-2 analogue as defined herein for the preparation of a medicament for the treatment and/or prevention of a side effect of chemotherapy or radiation treatment.

Said side effect of chemotherapy and/or radiation is diarrhoea, abdominal cramping, vomiting or structural and functional damage of the intestinal epithelium resulting from chemotherapy treatment.

The present invention further provides the use of a GLP-2 analogue as defined herein for the preparation of a medicament for the treatment of neo-natals, osteoporosis or DPP-IV (dipeptidylpeptidase-IV) mediated conditions.

The invention also provides a therapeutic kit comprising a cancer chemotherapy drug and a GLP-2 analogue of the present invention, each optionally in combination with a pharmaceutically aceptable carrier. The two therapeutic agents may be packaged separately (e.g. in separate vials) for separate administration, or may be provided in the same composition. Thus the invention further provides a pharmaceutical composition comprising a cancer chemotherapy drug and a GLP-2 analogue of the present invention in combination with a pharmaceutically acceptable carrier.

For patients having gastrointestinal mucosal neoplasia, or an increased risk of gastrointestinal mucosal neoplasia, it may be desirable to select a compound so as to reduce or abrogate the risk of reduced side effects such as stimulation or aggravation of gastrointestinal mucosal neoplasia. For example, when selecting a compound for treating a patient with colon neoplasia (whether benign or malignant), or at risk of developing colon neoplasia, it may be more appropriate to select a compound which is selective for the small intestine over the colon than a non-selective compound or a compound which is selective for the colon over the small intestine.

In other aspects, the present invention provides the use of the GLP-2 analogues for the preparation of a medicament for the treatment and/or prevention of malnutrition, for example conditions such as the wasting syndrome cachexia and anorexia.

In a further aspect, the present invention provides a nucleic acid molecule comprising a nucleic acid sequence encoding a GLP-2 analogue as defined herein.

In further aspects, the present invention provides an expression vector comprising the above nucleic acid sequence, optionally in combination with sequences to direct its expression, and host cells transformed with the expression vectors. Preferably the host cells are capable of expressing and secreting the GLP-2 analogue. In a still further aspect, the present invention provides a method of producing the GLP-2 analogue, the method comprising culturing the host cells under conditions suitable for expressing the GLP-2 analogue and purifying the GLP-2 analogue thus produced.

The invention further provides a nucleic acid of the invention, an expression vector of the invention, or a host cell capable of expressing and secreting a GLP-2 analogue of the invention, for use in therapy. It will be understood that the nucleic acid, expression vector and host cells may be used for treatment of any of the disorders described herein which may be treated with the GLP-2 analogues themselves. References to a therapeutic composition comprising a GLP-2 analogue of the invention, or administration of a GLP-2 analogue of the invention, should therefore be construed to encompass administration of a nucleic acid, expression vector or host cell of the invention except where the context demands otherwise.

In one embodiment the present invention relates to the use of a nucleic acid molecule, an expression vector, or a host cell as defined herein, in the preparation of a medicament for the treatment and/or prevention of a stomach and bowel-related disorder, or for the treatment and/or prevention of a side effect of chemotherapy or radiation treatment, or for the treatment of neo-natals, osteoporosis or DPP-IV (dipeptidylpeptidase-IV) mediated conditions.

In a further aspect, the present invention provides a method of treating a stomach and bowel-related disorder in a patient in need thereof by administering an effective amount a nucleic acid, expression vector or host cell of the invention. Examples of stomach and bowel-related disorders are provided above.

In a further aspect, the present invention provides a method of treating or preventing a side effect of chemotherapy or radiation therapy in a patient in need thereof, the method comprising administering an effective amount a nucleic acid, expression vector or host cell of the invention.

In a further aspect, the present invention provides a method of treating or preventing malnutrition, for example conditions such as the wasting syndrome cachexia and anorexia, in a patient in need thereof, the method comprising administering an effective amount a nucleic acid, expression vector or host cell of the invention.

Embodiments of the present invention will now be described in more detail by way of examples and not limitation with reference to the accompanying figures.

DETAILED DESCRIPTION OF THE INVENTION

Definitions

Figure 1:
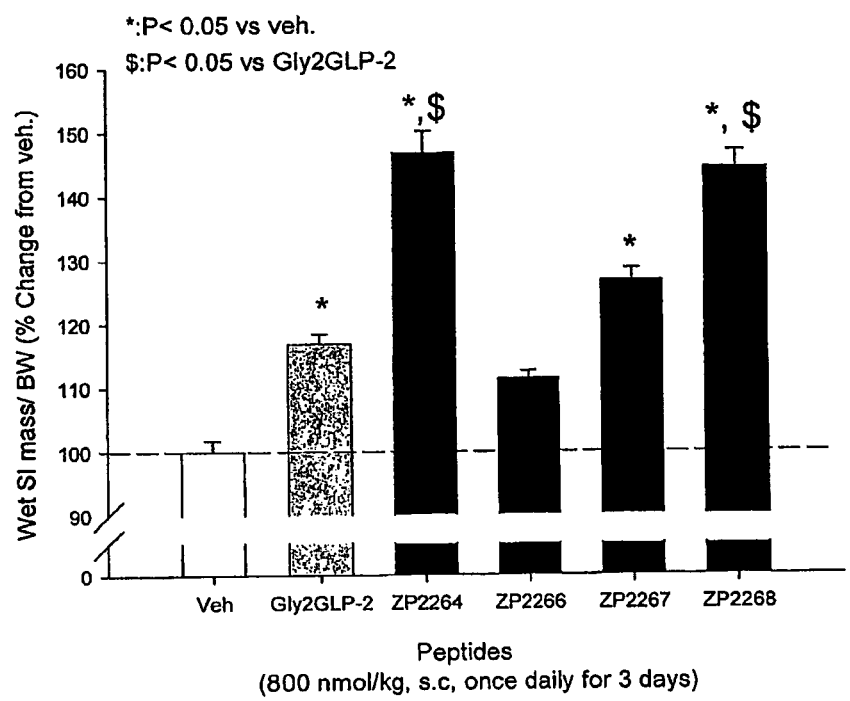
FIG. 1. Change in relative small intestinal mass, vs. vehicle controls following administration of the reference compound, [Gly2]GLP-2 and the compounds ZP2264, ZP2266-ZP2268 (800 nmol/kg, once daily for 3 days). Relative small intestinal mass is shown as 100% in the vehicle animals. *:P<0.05, vs. veh, $:P<0.05 vs. [Gly2]GLP-2 treated FIG. 2. Change in relative small intestinal mass, vs. vehicle controls following administration of the reference compound, [Gly2]GLP-2 and the compounds ZP2242, ZP2269 and ZP2272 and (800 nmol/kg, once daily for 3 days). Relative small intestinal mass is shown as 100% in the vehicle animals. *:P<0.05, vs. veh, $:P<0.05 vs. [Gly2]GLP-2 treated FIG. 3. Change in the ratio of small intestine mass/colon mass, vs. [Gly2]GLP-2-treated animals following administration of the compounds ZP2264, ZP2266-ZP2268 (800 nmol/kg, once daily for 3 days). Relative small intestinal (SI) mass is shown as 100% in the vehicle animals. $:P<0.05 vs. [Gly2]GLP-2 treated FIG. 4. Change in the ratio of small intestine mass/colon mass, vs. [Gly2]GLP-2-treated animals following administration of the compounds ZP2242, ZP2269, ZP2272 and ZP2271 (800 nmol/kg, once daily for 3 days). Relative small intestinal (SI) mass is shown as 100% in the [Gly2]GLP-2-treated animals.

Unless specified otherwise, the following definitions are provided for specific terms, which are used in the above written description.

Throughout the description and claims the conventional one-letter and three-letter codes for natural amino acids are used as well as generally accepted three letter codes for other α-amino acids, such as sarcosin (Sar), norleucine (Nle) and α-aminoisobutyric acid (Aib). All amino acid residues in peptides of the invention are preferably of the L-configuration, However, D-configuration amino acids may also be present.

As used herein "conservative substitution" means that an amino acid residue belonging to a certain position of the native human GLP-2 peptide sequence has been exchanged with an amino acid residue belonging to the same group (I, II, III, IV, V, 1, 2, 3) as defined in the following table:

| I | II | III | IV | V |
|---|----|-----|----|----|
| A | N  | H   | M  | F  |
| S | D  | R   | L  | Y  |
| T | E  | K   | I  | W  |
| P | Q  |     | V  |    |
| G |    |     | C  |    |

| 1 | 2 | 3 |
|---|---|---|
| A | G | H |
| V | S | R |
| L | T | K |
| I | C | D |
| P | Y | E |
| F | N |   |
| W | Q |   |
| M |   |   |

A "non-conservative" substitution as used herein means any other substitution of an amino acid residue of the native human GLP-2 sequence, e.g. such as substituting with a non-protein amino acid (Sar, Nle, Aib) or substituting with an amino acid which does not belong to the same group.

To describe the resulting hydrophophatic profile of one side of an alpha-helix we have chosen the Hydropathy index's ($hpi_X$) for the individual amino acids described by Kyte and Doolittle, J. Mol. Biol. (1982) 157, 105-132. In the present invention the helix of interest is outlined by the amino acid positions X11-X16-X20-X24-X28.

The Hydropathy Index (HPI) of the individual amino acids is described using the hydrophathy index HPI introduced and defined by Kyte and Doolittle, J. Mol. Biol. (1982) 157, 105-132.

HPI values for the individual amino acids are:

| Amino Acid | hpi-index |
|------------|-----------|
| I | 4.5 |
| V | 4.2 |
| L | 3.8 |
| F | 2.8 |
| C | 2.5 |
| M | 1.9 |
| A | 1.8 |
| G | −0.4 |
| T | −0.7 |
| W | −0.9 |
| S | −0.8 |
| Y | −1.3 |
| P | −1.6 |
| H | −3.2 |
| E | −3.5 |
| Q | −3.5 |
| D | −3.5 |
| N | −3.5 |
| K | −3.9 |
| R | −4.5 |

The resulting hydrophaticity profile (HPP) of the residues X11, X16, X20, X24, X28 of formula I calculated as $HPP = \Sigma hpi_{X11} + hpi_{X16} + hpi_{X20} + hpi_{X24} + hpi_{X28}$ $HPP \geq -10$
$HPP \geq -4$
$HPP \geq 0$ $Y_1$, $Y_2$, $Y_4$, and $Y_5$ can individually be selected from the group: Asn, Asp, Glu, Gln, Lys, His, Arg, Ala, Ser, Thr, Pro, Gly, Leu, Ile, Val, Met or Phe.

$Y_3$ can be selected from the group: Asn, Asp, Glu, Gln, His, Arg, Ala, Ser, Thr, Pro, Gly, Leu, Ile, Val, Met or Phe.

For a small intestine-selective compound, within the overall criteria that HPP≥−10, −4 or 0, it may be desirable that HPI for positions 11 and 16 should independently be −0.8≤HPI≤3.8, for example −0.8≤HPI≤2.8, such as HPI=1.8.

For positions 20, 24 and 28 it may be desirable that HPI should independently be −0.8≤$HPI_{20,24,28}$≤1.8, for example −0.8≤$HPI_{20,24,28}$≤1.8, such as $HPI_{20,24,28}$=−0.8.

Thus, the residues at each of positions X11, X16, X20, X24 and X28 may independently be Ala, Ser, Gly or Thr.

For example, each of X11 and X16 may independently be Ala or Ser, and X20, X24 and X28 may be Ala, Ser, Gly or Thr.

For example X11 and X16 may be Ala and X20, X24 and X28 may be Ala, Ser, Gly or Thr Preferred combinations at positions X11, X16, X20, X24 and X28 may include Ala/Ala/Ala/Ser/Ser, Ala/Ala/Ser/Ser/Ser, Ala/Ala/Thr/Ser/Ser and Ala/Ala/Gly/Ser/Ser.

For a stomach-selective compound, within the overall criteria that HPP≥−10, −4 or 0, it may be desirable that HPI for positions 11 and 16 should independently be −3.9≤$HPI_{11,16}$≤3.8. For example $HPI_{11,16}$ may be 2.8≤$HPI_{11,16}$≤3.8, or $HPI_{11,16}$ may be −3.9.

For positions 20, 24 and 28 it may be desirable that HPI should independently be −3.9≤$HPI_{20,24,28}$≤1.8. For example $HPI_{20,24,28}$ may be −0.8≤$HPI_{20,24,28}$≤1.8, or $HPI_{20,24,28}$ may be −3.9

Thus, the residue at position X11 may be Leu, Phe or Lys.

The residue at position X16 may be Leu, Ser, Phe, Lys or Thr.

The residue at postion X20 may be Ala, Ser, Leu, Gly or Thr.

The residue at position X24 may be Ala, Ser, Lys, Glu, Gly or Thr.

The residue at position X28 may be Ala, Ser, Lys, Gln, Gly or Thr.

For example, X11 and X16 may independently be Leu or Phe, X24 and X28 may independently be Ala or Ser.

Preferred compounds of the present invention have at least one GLP-2 biological activity, in particular in causing growth of the intestine or stomach. This can be assessed in vivo assays, for example as described in the examples, in which the mass of the intestine, or a portion thereof is determined after a test animal has been treated or exposed to a GLP-2 analogue.

The GLP-2 analogues of the present invention have one or more amino acid substitutions, deletions, inversions, or additions compared with native GLP-2 and as defined above. This definition also includes the synonym terms GLP-2 mimetics and/or GLP-2 agonists. Further, the analogue of the present invention may additionally have chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Preferably herein lower alkyl is $C_1$-$C_4$ alkyl. Furthermore, one or more side groups, or terminal groups, may be protected by protective groups known to the ordinarily-skilled peptide chemist. The α-carbon of an amino acid may be mono- or di-methylated.

Where they are present, oxidatively stable Met-replacement amino acid means one which is selected among the group consisting of Met(O) (methionine sulfoxide), Met(O)$_2$ (methionine sulfone), Val, Ile, Asn, Glx (Glu or Gln), Tyr, Phe, Trp and preferably Leu, Nle, Ala, Ser, and Gly.

It should be understood that the peptides of the invention might also be provided in the form of a salt or other derivative. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$ where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17$^{th}$ edition. Ed. Alfonso R. Gennaro (Ed.), Mark Publishing Company, Easton, Pa., U.S.A., 1985 and more recent editions, and in the Encyclopaedia of Pharmaceutical Technology.

Other derivatives of the GLP-2 analogues of the invention include coordination complexes with metal ions such as $Mn^{2+}$ and $Zn^{2+}$, esters such as in vivo hydrolysable esters, free acids or bases, hydrates, prodrugs or lipids. Esters can be formed between hydroxyl or carboxylic acid groups present in the compound and an appropriate carboxylic acid or alcohol reaction partner, using techniques well known in the art. Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. Examples of prodrugs include the use of protecting groups which may be removed in situ releasing active compound or serve to inhibit clearance of the drug in vivo.

When present, $Z^1$ and $Z^2$ each independently represent a peptide sequence of 3-20 or 4-20 amino acid residues, e.g. in the range of 4-15, more preferably in the range of 4-10 in particular in the range of 4-7 amino acid residues, e.g., of 4, 5, 6 or 7 amino acid residues, such as 6 amino acid residues. Each of the amino acid residues in the peptide sequences Z may independently be selected from Ala, Leu, Ser, Thr, Tyr, Asn, Gln, Asp, Glu, Lys, Arg, His, Met, Orn. Preferably, the amino acid residues are selected from Ser, Thr, Tyr, Asn, Gln, Asp, Glu, Lys, Arg, His, Orn, and Met, as well as amino acids falling within formula I as defined in WO01/04156, e.g., Dbu (2,4 diaminobutyric acid) or Dpr (2,3-diaminopropanoic acid), more preferably from Glu, Lys, and Met, especially Lys. The above-mentioned amino acids may have either D- or L-configuration, but preferably the above-mentioned amino acids have an L-configuration. Particularly preferred sequences Z are sequences of four, five or six consecutive lysine residues, and particularly six consecutive lysine residues. Exemplary sequences Z are shown in WO 01/04156.

In certain embodiments, $Z^1$ is absent. In such cases, $Z^2$ may be either present or absent.

GLP-2 analogues having at least an EC50 of 1 nM are defined as GLP-2 agonists.

The present invention includes the following peptides further described in the experimental section below.

Particularly preferred compounds of the present invention include compounds ZP2264, ZP2267, ZP2268 and ZP2270.

Stability Studies

The skilled person will be able to design appropriate methods (e.g. quantitative methods) for detection of degradation products of GLP-2 analogues, e.g. based on those described below. Degradation may occur as oxidation, hydrolysis and deamidation, depending on the identity and position of the amino acids in any given GLP-2 analogue, and conditions as pH, solution and temperature. The compounds can be ranked according to chemical stability, when the compounds are incubated under stressed conditions (i.e. conditions likely to cause degradation) and subsequently analysed for content of remaining intact peptide. In addition, the knowledge gained about major degradation products obtained under stressed conditions will be important for any later analytical method development.

Quantitative Assays to Detect GLP Analogues

The skilled person will also be capable of designing methods (e.g. quantitative methods) for detection of GLP analogues in complex environments or solutions (e.g. plasma, urine, tissue homogenates, cell homogenates, saliva or similar) to investigate the absorption, distribution, metabolism and excretion of the GLP analogues after administration to mammals or as part of functional studies of in vitro cell systems.

In one embodiment, a quantitative assay can be based on antibodies raised against the GLP analogues or fragments thereof. The antibodies obtained from the immunized animals can be used for quantitative assays. In one example a direct sandwich ELISA can be prepared using a first antibody with affinity of one part of the molecule immobilized in a multi-well plate. The sample is then applied to the wells and the GLP analogue is captured by the first antibody. The captured GLP analogue is then recognized by a second antibody with affinity for another part of the GLP analogue. The second antibody can be labeled with an enzyme (horseradish peroxidase, alkaline phosphatase or beta-galactosidase) or a radioisotope. The amount of captured GLP analogue can then be detected by addition of a colorimetric substrate or direct counting of radio-emission or by scintillation. Alternatively, the amount of captured GLP analogue can be detected indirectly by addition of a labeled antibody with affinity for the second antibody. The concentration in the sample can be estimated from the response obtained from an external standard curve containing known amounts of GLP analogue. Alternatively, the antibodies can be used to prepare a direct competitive immuno assay, where an antibody specific for the GLP analogue is immobilized on a multi-well plate and the sample incubated in the wells with a predefined fixed concentration of labeled GLP analogue. The label can be an enzyme, a fluorophore, a radioisotope or biotin and detected using, for example, substrates (e.g. colorimetric, fluorometric or chemiluminiscent) specific for the enzymes, scintillation or avidin linked to an enzyme followed by detection as described above. The amount of bound labeled GLP analogue can be detected by an appropriate method and the concentration of GLP analogue present in the sample derived from the response obtained from an external standard curve as described above.

In another embodiment, a quantitative assay can be based on liquid chromatography tandem mass spectroscopy methodology. In such a set up, the response from a fragment specific for the GLP analogue to be studied is monitored upon fragmentation of the parent compound induced by collision with an inert gas (He or Ar). Prior to fragmentation the sample components can be separated by reversed phase chromatography or the sample can be injected directly in the mass spectrometer. If suitable the sample can be subjected to pretreatment (i.e., addition of protease inhibitors, protein precipitation, solid phase extraction, immuno-affinity extraction, etc. The concentration of GLP analogue present in the sample derived from the response obtained from an external standard curve as described above, potentially after correction of the response using an internal standard similar to the GLP analogue to be studied.

Generation of Specific Antibodies

Specific antibodies against the GLP analogues or fragments thereof can be induced in mammals and purified from the serum. The GLP analogues or fragments can either be used directly with an adjuvant to immunize rabbits, mice or other mammals, or the GLP analogues or fragments thereof can be chemically linked to a carrier molecule (i.e., keyhole limpet hemocyanin, ovalbumin, albumin etc.) and injected with an adjuvant. The injections can be repeated with 2-4 weeks intervals for extended periods to improve the affinity and selectivity of the antibodies. Polyclonal antibodies can be harvested directly from the serum. To obtain monoclonal antibodies, B cells isolated from immunized animals, preferably mice, should be fused with tumor cells to form antibody producing hybridomas. Screening and selection of the appropriate clones and antibodies can be performed using either immobilized GLP analogues or peptides thereof followed by detection with labeled anti-antibodies. Alternatively the screening and selection could be based on immobilized antibodies followed by detection with labeled GLP analogues or fragments thereof. In all cases, the label could be a radioisotope, an enzyme, a fluorophore or biotin and detected using, for example, substrates (e.g. colorimetric, fluorometric or chemiluminiscent) specific for the enzymes, scintillation or avidin linked to an enzyme followed by detection as described.

Synthesis of GLP-2 Analogues

It is preferred to synthesize the analogues of the invention by means of solid phase or liquid phase peptide synthesis. In this context, reference is given to WO 98/11125 and, amongst many others, Fields, G B et al., 2002, "Principles and practice of solid-phase peptide synthesis". In: Synthetic Peptides ($2^{nd}$ Edition) and the Examples herein.

Thus the GLP-2 analogues may be synthesized in a number of ways including for example, a method which comprises:
(a) synthesizing the peptide by means of solid phase or liquid phase peptide synthesis and recovering the synthetic peptide thus obtained; or
(b) when the peptide is constituted by naturally occurring amino acids, expressing a nucleic acid construct that encodes the peptide in a host cell and recovering the expression product from the host cell culture; or
(c) when the peptide is constituted by naturally occurring amino acids, effecting cell-free in vitro expression of a nucleic acid construct that encodes the peptide and recovering the expression product; or
a combination of methods of (a), (b), and (c) to obtain fragments of the peptide, subsequently ligating the fragments to obtain the peptide, and recovering the peptide.

Thus, for some analogues of the invention it may be advantageous to exploit genetic engineering techniques. This may be the case when the peptide is sufficiently large (or produced as a fusion construct) and when the peptide only includes naturally occurring amino acids that can be translated from RNA in living organisms.

For the purpose of recombinant gene technology nucleic acid fragments encoding the peptides of the invention are important chemical products. Hence, a further aspect of the present invention provides a nucleic acid molecule comprising a nucleic acid sequence encoding a GLP-2 analogue of the invention, where the peptide preferably is comprised by naturally occurring amino acids. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

The general outline of a vector of the invention comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma) of or a leader peptide for multiple use e.g. combined secretion, purification tag and enzymatic trimming to correct peptide or integration into the membrane of the polypeptide fragment, the nucleic acid fragment encoding the peptide of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome.

The vectors of the invention are used to transform host cells to produce the modified peptide of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria (such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (such as *Saccharomyces cerevisiae*), and protozoans. Alternatively, the transformed cells are derived from a multicellular organism, i.e. it may be fungal cell, an insect cell, a plant cell, or a mammalian cell. Also cells derived from a human being are interesting, cf. the discussion of cell lines and vectors below. For the purposes of cloning and/or optimised expression it is preferred that the transformed cell is capable of replicating the nucleic acid fragment of the invention. Cells expressing the nucleic fragment are preferred useful embodiments of the invention; they can be used for small-scale or large-scale preparation of the peptides of the invention.

When producing the peptide of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the peptide. Preferably, this stable cell line secretes or carries the peptide of the invention, thereby facilitating purification thereof.

In general, plasmid vectors containing replicon and control sequences, which are derived from species compatible with the host cell, are used in connection with the hosts. The vector ordinarily carries a replication site, as well as marking sequences, which are capable of providing phenotypic selection in transformed cells. For example, *E. coli* is typically transformed using pBR322 (but numerous other useful plasmids exist) a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain promoters, which can be used by the prokaryotic microorganism for expression.

Those promoters most commonly used in prokaryotic recombinant DNA construction include the β-lactamase (penicillinase) and lactose promoter systems (Chang et al., 1978; Itakura et al., 1977; Goeddel et al., 1979) and a tryptophan (trp) promoter system (Goeddel et al., 1979; EP 0 036 776 A). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used, and also here the promoter should be capable of driving expression. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), the *D. melanogaster* cell line $S_2$ available from Invitrogen, PO Box 2312, 9704 CH Groningen, The Netherlands, and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment, which also contains the SV40 viral origin of replication (Fiers et al., 1978). Smaller or larger SV40 fragments may also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV) or may be provided by the host cell chromosomal replication mechanism. If the vector is integrated into the host cell chromosome, the latter is often sufficient.

In order to obtain satisfactory yields in a recombinant production process, it may be advantageous to prepare the analogues as fusion proteins, either by fusing the peptide to a fusion partner that can serve as an affinity tag (for ease of purification) and/or by having multiple repeats of the peptide. These methods require presence of a suitable cleavage site for a peptidase, but the skilled person will know how to tailor the underlying genetic constructs.

After recombinant preparation, the peptides of the invention can be purified by methods generally known in the art, including multi-step chromatography (ion-exchange, size-exclusion, and affinity chromatographic techniques).

Alternatively, peptides comprised of naturally occurring amino acids can be prepared in vitro in cell free systems. This is especially expedient in cases where the peptides could be toxic for putative host cells. Thus, the present invention also contemplates use of cell-free in vitro translation/expression in order to prepare the peptides of the invention. In this context, reference is made to commercially available in vitro translation kits, materials, and technical documentation from e.g. Ambion Inc., 2130 Woodward, Austin, Tex. 78744-1832, USA.

Finally, the available methods can of course be combined so as to prepare e.g. semi-synthetic analogues. In such a set up, peptide fragments are prepared using at least 2 separate steps or methods, followed by ligation of the fragments to obtain the final peptide product.

Pharmaceutical Compositions and Administration

The GLP-2 analogues of the present invention, or salts or derivatives thereof, may be formulated as pharmaceutical compositions prepared for storage or administration, and which comprise a therapeutically effective amount of a GLP-2 peptide of the present invention, or a salt or derivative thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy so as to deliver the peptide to the large intestine, but will depend on such factors as weight, diet, concurrent medication and other factors, well known those skilled in the medical arts.

It is within the invention to provide a pharmaceutical composition, wherein the GLP-2 analogue, or a salt thereof is present in an amount effective to treat or prevent stomach and bowel-related disorders.

Pharmaceutically acceptable salts of the compounds of the invention having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethyl-propylamine), or a mono-, di- or trihydroxy lower alkylamine (e.g., mono-, di- or triethanolamine). Internal salts also may be formed. Similarly, when a compound of the present invention contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, and camphorsulfonic as well as other known pharmaceutically acceptable acids. Amino acid addition salts can also be formed with amino acids such as lysine, glycine, or phenylalanine.

As is apparent to one skilled in the medical art, a "therapeutically effective amount" of the peptides or pharmaceutical compositions of the present invention will vary depending upon the age, weight and mammalian species treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of preventing and/or treating the intestine and stomach related diseases described herein, as well as other medical indications disclosed herein, will be within the ambit of the skilled person.

As used herein, "a therapeutically effective amount" is one which reduces symptoms of a given condition or pathology, and preferably which normalizes physiological responses in an individual with the condition or pathology. Reduction of symptoms or normalization of physiological responses can be determined using methods routine in the art and may vary with a given condition or pathology. In one aspect, a therapeutically effective amount of one or more GLP-2 analogues or pharmaceutical composition comprising the one or more GLP-2 analogues is an amount which restores a measurable physiological parameter to substantially the same value (preferably to within +30%, more preferably to within +20%, and still more preferably, to within 10% of the value) of the parameter in an individual without the condition or pathology.

In one embodiment of the invention administration of the compounds or pharmaceutical composition of the present invention is commenced at lower dosage levels, with dosage levels being increased until the desired effect of preventing/treating the relevant medical indication, such as intestine and stomach related diseases is achieved. This would define a therapeutically effective amount. For the peptides of the present invention, alone or as part of a pharmaceutical composition, such doses may be between about 0.01 mg/kg and 100 mg/kg body weight, such as between about 0.01 mg/kg and 10 mg/kg body weight, for example between 10-100 µg/kg body weight.

For therapeutic use, the chosen GLP-2 analogue is formulated with a carrier that is pharmaceutically acceptable and is appropriate for delivering the peptide by the chosen route of administration. For the purpose of the present invention, peripheral parenteral routes include intravenous, intramuscular, subcutaneous, and intra peritoneal routes of administration. Certain compounds used in the present invention may also be amenable to administration by the oral, rectal, nasal, or lower respiratory routes. These are so-called non-parenteral routes. The present pharmaceutical composition comprises a GLP-2 analogue of the invention, or a salt or derivative thereof and a pharmaceutically acceptable carrier. Suitable pharmaceutically acceptable carriers are those used conventionally with peptide-based drugs, such as diluents, excipients and the like. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. Preferred buffer ranges are pH 4-8, pH 6.5-8, more preferably pH 7-7.5. Preservatives, such as para, meta, and ortho-cresol, methyl- and propylparaben, phenol, benzyl alcohol, sodium benzoate, benzoic acid, benzyl-benzoate, sorbic acid, propanoic acid, esters of p-hydroxybenzoic acid may be provided in the pharmaceutical composition. Stabilizers, preventing oxidation, deamidation, isomerisation, racemisation, cyclisation, peptide hydrolysis, such as e.g. ascorbic acid, methionine, tryptophane, EDTA, asparagine, lysine, arginine, glutamine and glycine may be provided in the pharmaceutical composition. Stabilizers, preventing aggregation, fibrillation and precipitation, such as Sodium dodecyl sulphate, polyethylene glycol, carboxymethyl cellulose, cyclodextrine may be provided in the pharmaceutical composition. Organic modifiers for solubilization or preventing aggregation, such as ethanol, acetic acid or acetate and salts thereof may be provided in the pharmaceutical composition. Isotonicity makers such as salts e.g. sodium chloride or most preferred carbohydrates e.g. dextrose, mannitol, lactose, trehalose, sucrose or mixtures thereof may be provided in the pharmaceutical composition.

Detergents, such as Tween 20, Tween 80, SDS, Poloxamers e.g. Pluronic F-68, Pluronic F-127, may be provided in the pharmaceutical composition. Dyes and even flavoring agents may be provided in the pharmaceutical composition. In another embodiment, a pharmaceutically acceptable acid addition salt of the GLP-2 peptide analogue is provided for. Suspending agents may be used.

Organic modifiers, such as ethanol, tertiary-buthanol, 2-propanol, ethanol, glycerol, Polyethylene glycol may be provided in the pharmaceutical formulation for lyophilization of a lyophilized product. Bulking agents and isotonicity makers such as salt e.g. sodium chloride, carbohydrates e.g. dextrose, mannitol, lactose, trehalose, sucrose or mixtures thereof, aminoacids e.g. glycine, glutamate, or excipients such as cystein, lecithin or human serum albumin, or mixtures thereof may be provided in the pharmaceutical composition for lyophilization.

The pharmaceutical compositions of the present invention may be formulated and used as tablets, capsules or elixirs for oral administration; suppositories for rectal administration; preferably sterile solutions or sterile powder or suspensions for injectable administration; and the like. The dose and method of administration can be tailored to achieve optimal efficacy but will depend on such factors as weight, diet, concurrent medication and other factors, which those skilled in the medical arts will recognize.

When administration is to be parenteral, such as intravenous and subcutaneous, e.g., on a daily basis, injectable pharmaceutical compositions can be prepared in conventional forms, either as aqueous solutions or suspensions; lyophilized, solid forms suitable for reconstitution immediately before use or suspension in liquid prior to injection, or as emulsions.

Diluents for reconstitution of the lyophilized product may be a suitable buffer from the list above, water, saline, dextrose, mannitol, lactose, trehalose, sucrose, lecithin, albumin, sodium glutamate, cysteine hydrochloride; or water for injection with addition of detergents, such as Tween 20, Tween 80, poloxamers e.g. pluronic F-68 or pluronic F-127, polyethylene glycol, and or with addition of preservatives such as para-, meta-, and ortho-cresol, methyl- and propylparaben, phenol, benzyl alcohol, sodium benzoate, benzoic acid, benzyl-benzoate, sorbic acid, propanoic acid, esters of p-hydroxybenzoic acid, and or with addition of an organic modifier such as ethanol, acitic acid, citric acid, lactic acid or salts thereof.

In addition, if desired, the injectable pharmaceutical compositions may contain minor amounts of non-toxic auxiliary substances, such as wetting agents, or pH buffering agents. Absorption enhancing preparations (e.g., liposomes, detergents and organic acids) may be utilized.

In one embodiment of the invention, the compounds are formulated for administration by infusion, e.g., when used as liquid nutritional supplements for patients on total parenteral nutrition therapy (for example neonatals, or patients suffering from cachexia or anorexia), or by injection, for example subcutaneously, intraperitoneal or intravenously, and are accordingly utilized as aqueous solutions in sterile and pyrogen-free form and optionally buffered to physiologically tolerable pH, e.g., a slightly acidic or physiological pH. Formulation for intramuscular administration may be based on solutions or suspensions in plant oil, e.g. canola oil, corn oil or soy bean oil. These oil based formulations may be stabilized by antioxidants e.g. BHA (butylated hydroxianisole) and BHT (butylated hydroxytoluene).

Thus, the present peptide compounds may be administered in a vehicle, such as distilled water or in saline, phosphate buffered saline, 5% dextrose solutions or oils. The solubility of the GLP-2 analogue may be enhanced, if desired, by incorporating a solubility enhancer, such as detergents and emulsifiers.

The aqueous carrier or vehicle can be supplemented for use as injectables with an amount of gelatin that serves to depot the GLP-2 analogue at or near the site of injection, for its slow release to the desired site of action. Alternative gelling agents, such as hyaluronic acid, may also be useful as depot agents.

In one embodiment of the present invention the formulation comprises
a. L-histidine dissolved in water to obtain final concentrations of from 0.5 mM to 300 mM, preferably from 3 to 200 mM, most preferably from 20 to 100 mM;
b. mannitol to obtain up to 350 mM, preferably from 30 to 300 mM, most preferably from 100 mM to 230 mM; and
c. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In another embodiment of the present invention the formulation comprises
a. L-histidine dissolved in water to obtain final concentrations of from 0.5 mM to 300 mM, preferably from 3 to 200 mM, most preferably from 20 to 100 mM L-histidine;
b. L-Arginine to obtain up to 200 mM, preferably from 0.5 to 100 mM, most preferably from 5 to 50 mM;
c. mannitol to obtain up to 350 mM, preferably from 30 to 300 mM, most preferably from 100 mM to 230 mM; and
d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In still another embodiment of the present invention the formulation comprises
a. L-histidine dissolved in water to obtain final concentrations of up to 200 mM, preferably from 3 to 100 mM, most preferably from 5 to 50 mM L-histidine;
b. L-Arginine to obtain up to 200 mM, preferably from 0.5 to 100 mM, most preferably from 5 to 50 mM;
c. mannitol to obtain up to 350 mM, preferably from 30 to 300 mM, most preferably from 100 mM to 230 mM; and
d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises
a. L-histidine dissolved in water to obtain final concentrations of from 0.5 to 300 mM, preferably from 3 to 200 mM, most preferably from 20 to 100 mM L-histidine;
b. L-Arginine to obtain up to 200 mM, preferably from 0.5 to 100 mM, most preferably from 5 to 50 mM;
c. mannitol to obtain up to 350 mM, preferably from 30 to 300 mM, most preferably from 100 mM to 230 mM; and
d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises
a. L-histidine dissolved in water to obtain final concentrations of from up to 200 mM, preferably from 3 to 100 mM, most preferably from 5 to 50 mM L-histidine;
b. L-Arginine to obtain up to 200 mM, preferably from 0.5 to 100 mM, most preferably from 5 to 50 mM;
c. mannitol to obtain up to 350 mM, preferably from 30 to 300 mM, most preferably from 100 mM to 230 mM; and
d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises
a. N-acetate dissolved in water to obtain final concentrations of from up to 200 mM, preferably from 0.5 to 100 mM, most preferably from 5 to 50 mM L-histidine;
b. mannitol to obtain up to 350 mM, preferably from 30 to 300 mM, most preferably from 100 mM to 230 mM.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product The GLP-2 analogues of the invention may also be formulated as a slow release implantation device for extended and sustained administration of the GLP-2 peptide analogue. Such sustained release formulations may be in the form of a patch positioned externally on the body. Examples of sustained release formulations include composites of biocompatible polymers, such as poly(lactic acid), poly(lactic-co-glycolic acid), methylcellulose, hyaluronic acid, sialic acid, silicate, collagen, liposomes and the like. Sustained release formulations may be of particular interest when it is desirable to provide a high local concentration of a GLP-2 analogue of the invention.

The GLP-2 analogue may be utilized in the form of a sterile-filled vial or ampoule containing an intestinotrophic amount of the peptide, in either unit dose or multi-dose amounts. The vial or ampoule may contain the GLP-2 analogue and the desired carrier, as an administration ready formulation. Alternatively, the vial or ampoule may contain the GLP-2 peptide in a form, such as a lyophilized form, suitable for reconstitution in a suitable carrier, such as sterile water or phosphate-buffered saline.

As an alternative to injectable formulations, the GLP-2 analogue may be formulated for administration by other routes. Oral dosage forms, such as tablets, capsules and the like, can be formulated in accordance with standard pharmaceutical practice. According to the present invention, the GLP-2 analogue is administered to treat individuals that would benefit from growth of small bowel tissue.

Nasal dosage forms can be formulated with addition of enhancers, such as Chitosan or detergents such as Tween 20, Tween 80, Poloxamers e.g. Pluronic F-68, Pluronic F-127; Brij 35, Brij 72, cremophor EL.

The peptide compounds of the present invention may be used alone, or in combination with compounds having an anti-inflammatory effect. Without being bound by theory it is envisioned that such combination treatment may enforce the beneficial treatment effects of the present peptide analogues.

The therapeutic dosing and regimen most appropriate for patient treatment will of course vary with the disease or condition to be treated, and according to the patient's weight and other parameters. Without wishing to be bound by any particular theory, it is expected that doses, in the µg/kg range, and shorter or longer duration or frequency of treatment may produce therapeutically useful results, such as a statistically significant increase particularly in small bowel mass. In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

A human dose of a GLP-2 peptide according to the invention may in one embodiment be from about 10 µg/kg body weight/day to about 10 mg/kg/day, preferably from about 50 µg/kg/day to about 5 mg/kg/day, and most preferably about 100 µg/kg/day to 1 mg/kg/day.

Medical Conditions

The peptides of the present invention are useful as a pharmaceutical agent for preventing or treating an individual suffering from gastro-intestinal disorders, including the upper gastrointestinal tract of the oesophagus by administering an effective amount of a GLP-2 analogue, or a salt thereof as described herein. The stomach and intestinal-related disorders include ulcers of any aetiology (e.g., peptic ulcers, Zollinger-Ellison Syndrome, drug-induced ulcers, ulcers related to infections or other pathogens), digestion disorders, malabsorption syndromes, short-bowel syndrome, cul-de-sac syndrome, inflammatory bowel disease (Crohns disease and ulcerative colitis), celiac sprue (for example arising from gluten induced enteropathy or celiac disease), tropical sprue, hypogammaglobulinemic sprue, and chemotherapy and/or radiationhemotherapy induced mucositis and diarrhea.

For patients having gastrointestinal mucosal neoplasia, or an increased risk of gastrointestinal mucosal neoplasia, it may be desirable to select a compound so as to reduce or abrogate the risk of reduced side effects such as stimulation or aggravation of gastrointestinal mucosal neoplasia. For example, when selecting a compound for treating a patient with colon neoplasia (whether benign or malignant), or at risk of developing colon neoplasia, it may be more appropriate to select a compound which is selective for the small intestine over the colon than a non-selective compound or a compound which is selective for the colon over the small intestine As mentioned above in general, individuals who would benefit from increased small intestinal mass and consequent and/or maintenance of normal small intestine mucosal structure and function are candidates for treatment with the present GLP-2 analogues. Particular conditions that may be treated with GLP-2 analogue include the various forms of sprue including celiac sprue which results from a toxic reaction to alpha-gliadin from heat and may be a result of gluten-induced enteropathy or celiac disease, and is marked by a significant loss of villae of the small bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the GLP-2 analogue treatment may be monitored by enteric biopsy to examine the villus morphology, by biochemical assessment of nutrient absorption, by non invasive determination of intestinal permeability, by patient weight gain, or by amelioration of the symptoms associated with these conditions.

The GLP-2 analogues of the present invention may be useful as pharmaceutical agents for preventing or treating stomach related disorders including ulcers of any aetiology (e.g., peptic ulcers, Zollinger-Ellison Syndrome, drug-induced ulcers, ulcers related to infections or other pathogens), Other conditions that may be treated with the GLP-2 analogues of the invention, or for which the GLP-2 analogues may be useful prophylactically, include in addition to the above mentioned radiation enteritis, infectious or post-infectious enteritis, and small intestinal damage due to cancer-chemotherapeutic or toxic agents.

The GLP-2 analogues may also be used for the treatment of malnutrition, for example cachexia and anorexia.

A particular embodiment of the invention is concerned with using the present peptides for the prevention and/or treatment of intestinal damage and dysfunction. The stem cells of the small intestinal mucosa are particularly susceptible to the cytotoxic effects of chemotherapy due to their rapid rate of proliferation (Keefe et al., Gut 2000; 47: 632-7). Administration of the present GLP-2 peptide agonists may enhance trophic effect in the intestinal crypts and rapidly provide new cells to replace the damaged intestinal epithelium following chemotherapy and/or radiation therapy. The ultimate goal achieved by administering the present peptides is to reduce the morbidity related to gastrointestinal damage of patients undergoing chemotherapy treatment while increasing tolerance to more aggressive chemotherapy, radiation and combination chemotherapy and radiation therapies. Concomitant prophylactic or therapeutic treatment may be provided in accordance with the present invention to patients undergoing or about to undergo radiation therapy.

Gastrointestinal mucositis after anti-cancer chemotherapy is an increasing problem that is essentially untreatable once established, although it gradually remits. Studies conducted with the commonly used cytostatic cancer drugs 5-FU and irinotecan have demonstrated that effective chemotherapy with these drugs predominantly affects structural integrity and function of the small intestine while the colon is less sensitive and mainly responds with increased mucus formation (Gibson et al., J Gastroenterol Hepatol. 18(9):1095-1100, 2003; Tamaki et al., J Int Med. Res. 31(1):6-16, 2003).

The novel GLP-2 analogues of the present invention may be useful in the prevention and/or treatment of gastrointestinal injury and side effects of chemotherapeutic agents. This potentially important therapeutic application may apply to currently used chemotherapeutic agents such as but not limited to: 5-FU, Altretamine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, Vinorelbine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Gemcitabine, Hydroxycarbamide, Idarubicin, Ifosfamide, Irinotecan, Liposomal doxorubicin, Leucovorin, Lomustine, Melphalan, Mercaptopurine, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, and Vinorelbine.

It is envisioned that the present peptides may be employed in a method of treating neo-natals by administering an effective amount of a GLP-2 analogue, or a salt thereof. Complications with feeding neonatals due to the lack of development of the intestine may be overcome by using the present peptide agonists.

In another embodiment the invention describes a method of treating DPP-IV (dipeptidylpeptidase-IV) mediated conditions by administering to a patient in need thereof an effective amount of a GLP-2 analogue, or a salt thereof. Such diseases include conditions in which the DPP-IV enzyme is over expressed.

The pharmaceutical composition may in one embodiment be formulated to cause slow release of said GLP-2 analogue, or a salt or derivative thereof as described above.

It is envisaged that the present peptides may be employed in a method of treating neo-natals by administering an effective amount of a GLP-2 analogue, or a salt thereof. Complications with feeding neonatals due to the lack of development of the intestine may be overcome by using the present peptide agonists.

In another embodiment the invention describes a method of treating DPP-IV (dipeptidylpeptidase-IV) mediated conditions by administering to a patient in need thereof an effective amount of a GLP-2 analogue, or a salt thereof. Such diseases include conditions in which the DPP-IV enzyme is over expressed.

EXAMPLES

The following examples are provided to illustrate preferred aspects of the invention and are not intended to limit the scope of the invention.

General Peptide Synthesis
Apparatus and Synthetic Strategy

Peptides were synthesized batchwise in a polyethylene vessel equipped with a polypropylene filter for filtration using 9-fluorenylmethyloxycarbonyl (Fmoc) as N-α-amino protecting group and suitable common protection groups for side-chain functionalities.

Solvents

Solvent DMF (N,N-dimethylformamide, Riedel de-Häen, Germany) was purified by passing through a column packed with a strong cation exchange resin (Lewatit S 100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O- anion) if free amines are present. Solvent DCM (dichloromethane, analytical grade, Riedel de-Häen, Germany) was used directly without purification. Acetonitril (HPLC-grade, Lab-Scan, Dublin Ireland) was used directly without purification.

Amino Acids

Fmoc-protected amino acids were purchased from Advanced ChemTech (ACT) in suitable side-chain protected forms.

Coupling Reagents

Coupling reagent diisopropylcarbodiimide (DIC) was purchased from Riedel de-Häen, Germany.

Solid Supports

Peptides were synthesized on TentaGel S resins 0.22-0.31 mmol/g. TentaGel S-Ram, TentaGel S RAM-Lys(Boc)Fmoc (Rapp polymere, Germany) were used in cases where a C-terminal amidated peptide was preferred, while TentaGel S PHB, TentaGel S PHB Lys(Boc)Fmoc were used when a C-terminal free carboxylic acid was preferred.

Catalysts and Other Reagents

Diisopropylethylamine (DIEA) was purchased from Aldrich, Germany, piperidine and pyridine from Riedel-de Häen, Frankfurt, Germany. Ethandithiol was purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland. Acetic anhydride was obtained from Fluka.

Coupling Procedures

The amino acids were coupled as in situ generated HObt or HOAt esters made from appropriate N-a-protected amino acids and HObt or HOAt by means of DIC in DMF. Acylations were checked by the ninhydrin test performed at 80° C. in order to prevent Fmoc deprotection during the test (Larsen, B. D. and Holm, A., Int. J. Peptide Protein Res. 43, 1994, 1-9).

Deprotection of the N-α-Amino Protecting Group (Fmoc).

Deprotection of the Fmoc group was performed by treatment with 20% piperidine in DMF (1×5 and 1×10 min.), followed by wash with DMF (5×15 ml, 5 min. each) until no yellow color could be detected after addition of Dhbt-OH to the drained DMF.

Coupling of HOBt-Esters 3 eq. N-α-amino protected amino acid was dissolved in DMF together with 3 eq. HObt and 3 eq DIC and then added to the resin.

Cleavage of Peptide from Resin with Acid.

Peptides were cleaved from the resins by treatment with 95% trifluoroacetic acid (TFA, Riedel-de Häen, Frankfurt, Germany)-water v/v or with 95% TFA and 5% ethandithiol v/v at r.t. for 2 h. The filtered resins were washed with 95% TFA-water and filtrates and washings evaporated under reduced pressure. The residue was washed with ether and freeze dried from acetic acid-water. The crude freeze dried product was analyzed by high-performance liquid chromatography (HPLC) and identified by mass spectrometry (MS).

Batchwise Peptide Synthesis on TentaGel Resin (PEG-PS).

TentaGel resin (1 g, 0.23-0.24 mmol/g) was placed in a polyethylene vessel equipped with a polypropylene filter for filtration. The resin was swelled in DMF (15 ml), and treated with 20% piperidine in DMF in order to remove the initial Fmoc group either on the linker TentaGel S RAM or on the first amino acid on the resin TentaGel S RAM-Lys(Boc) Fmoc. The resin was drained and washed with DMF until no yellow color could be detected after addition of Dhbt-OH to the drained DMF. The amino acids according to the sequence were coupled as preformed Fmoc-protected HObt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test as described above. After completed synthesis the peptide-resin was washed with DMF (3×15 ml, 5 min each), DCM (3×15 ml, 1 min each) and finally diethyl ether (3×15 ml, 1 min each) and dried in vacuo. The peptide was cleaved from the resin as described earlier and the crude peptide product was analysed and purified as described below HPLC Conditions Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition. The following columns and HPLC buffer system was used:

Column: VYDAC 238TP5415, C-18, 5 mm, 300 Å 150×4.6 mm.

Buffers: A: 0.1% TFA in MQV; B: 0.085% TFA, 10% MQV, 90% MeCN.
Gradient: 0-1.5 min. 0% B
1. 5-25 min 50% B
25-30 min 100% B
30-35 min 100% B
35-40 min 0% B
Flow 1, ml/min, oven temperature 40° C., UV detection: I=215 nm.

HPLC Purification of the Crude Peptide

The crude peptide products were purified PerSeptive Biosystems VISION Workstation. VISION 3.0 software was used for instrument control and data acquisition. The following column and HPLC buffer system was used:
Column: Kromasil KR 100 Å, 10 mm C-8, 250×50.8 mm.
Buffer system: Buffers: A: 0.1% TFA in MQV; B: 0.085% TFA, 10% MQV, 90% MeCN.
Gradient: 0-37 min. 0-40% B
Flow 35 ml/min, UV detection: I=215 nm and 280 nm.

Mass Spectroscopy

The peptides were dissolved in super gradient methanol (Labscan, Dublin, Ireland), milli-Q water (Millipore, Bedford, Mass.) and formic acid (Merck, Damstadt, Germany) (50:50:0.1 v/v/v) to give concentrations between 1 and 10 mg/ml. The peptide solutions (20 ml) were analysed in positive polarity mode by ESI-TOF-MS using a LCT mass spectrometer (Micromass, Manchester, UK) accuracy of +/−0.1 m/z.

General Synthetic Procedure

In all syntheses dry TentaGel-S-Ram resin (1 g, 0.22-0.31 mmol/g) was placed in a polyethylene vessel equipped with a polypropylene filter for filtration. The resin was swelled in DMF (15 ml), and treated with 20% piperidine in DMF to secure the presence of non-protonated amino groups on the resin. The resin was drained and washed with DMF until no yellow colour could be detected after addition of Dhbt-OH to the drained DMF. The amino acids according to the sequence were coupled as preformed Fmoc-protected HOBt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test performed at 80° C. After completed synthesis the peptide-resin was washed with DMF (3×15 ml, 5 min each), DCM (3×15 ml, 1 min each) and finally diethyl ether (3×15 ml, 1 min each) and dried in vacuo. The peptide was then cleaved from the resin as described above and freeze dried.

After purification using preparative HPLC as described above, the peptide product was collected and the identity of the peptide was confirmed by ES-MS. This procedure was used for the synthesis of all peptides exemplified further below.

Compounds Synthesised

Using the above techniques compounds 1809 to 1861 and reference compound 1559 (H-[Gly2]hGLP-2-OH) were synthesised using the methods described above (Table 1).

TABLE 1

Compounds synthesized

| ZP no. | Sequence | Mw mono isotopic (g/mol) calculated | Mw mono isotopic (g/mol) found | Purity % | Yield/g resin mg |
|---|---|---|---|---|---|
| 2264 | H-HGEGSFSDELATILEALAAADFIAWLIATKITD-NH2 (SEQ ID NO: 8) | 3487.79 | 3487.5 | 93 | 21 |
| 2266 | H-HGEGSFSDELETILEELAAEDFIEWLIETKITD-NH2 (SEQ ID NO: 9) | 3777.81 | 3777.1 | 88 | 38 |
| 2267 | H-HGEGSFSDELSTILESLAAADFIAWLIATKITD-NH2 (SEQ ID NO: 10) | 3519.78 | 3519.5 | 96 | 30 |
| 2268 | H-HGEGSFSDELATILEALAASDFISWLISTKITD-NH2 (SEQ ID NO: 11) | 3535.77 | 3535.68 | 91 | 17 |
| 2269 | H-HGEGSFSDELKTILESLAAADFIEWLIQTKITD-NH2 (SEQ ID NO: 12) | 3675.87 | 3675.4 | 94 | 34 |
| 2272 | H-HGEGSFSDELATILESLAAADFISWLIATKITD-NH2 (SEQ ID NO: 14) | 3519.78 | 3519.6 | 91 | 20 |
| 2263 | H-HGEGSFSDELSTILESLAASDFISWLISTKITD-NH2 (SEQ ID NO: 7) | 3567.76 | 3567.3 | 62 | 16 |
| 2270 | H-HGEGSFSDELNTILESLAASDFISWLISTKITD-NH2 (SEQ ID NO: 13) | 3594.77 | 3594.5 | 74 | 28 |
| 2242 | H-HGEGSFSSELSTILDALAARDFIAWLIATKITDK-OH (SEQ ID NO: 15) | 3675.19 | 3675.9 | 88 | 87 |
| 2378 | H-HGEGSFSDELETILEELAAEDFIEWLIETKITDKKKKKK-NH2 (SEQ ID NO: 16) | 4546.38 | 4546.50 | 93 | 73.4 |
| 2379 | H-HGEGSFSDELKTILESLAAADFIEWLIQTKITDKKKKKK-NH2 (SEQ ID NO: 17) | 4444.44 | 4444.13 | 96 | 24.9 |
| 2380 | H-HGEGSFSDELSTILESLAASDFISWLISTKITDKKKKKK-NH2 (SEQ ID NO: 18) | 4336.33 | 4336.75 | 96 | 40.6 |

TABLE 1-continued

Compounds synthesized

| ZP no. | Sequence | Mw mono isotopic (g/mol) calculated | Mw mono isotopic (g/mol) found | Purity % | Yield/g resin mg |
|---|---|---|---|---|---|
| 2381 | H-HGEGSFSDELATILEALAASDFISWLISTKITDKKKKKK-NH2 (SEQ ID NO: 19) | 4304.34 | 4304.50 | 97 | 38.5 |
| 2382 | H-HGEGSFSDELNTILESLAASDFISWLISTKITDKKKKKK-NH2 (SEQ ID NO: 20) | 4363.34 | 4363.55 | 94 | 12.9 |
| 2383 | H-HGEGSFSDELNTILESLAARDFISWLISTKITDKKKKKK-NH2 (SEQ ID NO: 21) | 4432.41 | 4432.60 | 96 | 16.8 |
| 2384 | H-HGEGSFSDELATILEALAAADFIAWLISTKITDKKKKKK-NH2 (SEQ ID NO: 22) | 4272.35 | 4272.40 | 98 | 27.3 |
| 2385 | H-HGEGSFSDELSTILEALAASDFISWLISTK1TDKKKKKK-NH2 (SEQ ID NO: 23) | 4320.34 | 4320.50 | 95 | 40.5 |
| 2386 | H-HGEGSFSDELATILESLAASDFISWLISTKITDKKKKKK-NH2 (SEQ ID NO: 24) | 4320.34 | 4320.75 | 89 | 65.3 |
| 2394 | H-HGEGSFSDELLTILELLAASDFISWLISTKITDKKKKKK-NH2 (SEQ ID NO: 25) | 4388.44 | 4389.13 | 90 | 23.2 |
| 2395 | H-HGEGSFSDELKTILEKLAAKDFIKWLIKTKITDKKKKKK-NH2 (SEQ ID NO: 26) | 4541.65 | 4541.61 | 96 | 32 |
| 2396 | H-HGEGSFSDELFTILEFLAASDFISWLISTKITDKKKKKK-NH2 (SEQ ID NO: 27) | 4456.75 | 4456.40 | 93 | 21.5 |
| 2397 | H-HGEGSFSDELATILEALAAADFIAWLISTKITD-NH2 (SEQ ID NO: 28) | 3503.88 | 3503.78 | 92 | 73.5 |
| 2398 | H-HGEGSFSDELSTILEALAASDFISWLISTKITD-NH2 (SEQ ID NO: 29) | 3551.77 | 3552.00 | 89 | 23.5 |
| 2399 | H-HGEGSFSDELATILESLAASDFISWLISTKITD-NH2 (SEQ ID NO: 30) | 3551.77 | 3551.75 | 80 | 45.6 |
| 2400 | H-HGEGSFSDELLTILELLAASDFISWLISTKITD-NH2 (SEQ ID NO: 31) | 3619.87 | 3620.50 | 84 | 6.8 |
| 2401 | H-HGEGSFSDELFTILEFLAASDFISWLISTKITD-NH2 (SEQ ID NO: 32) | 3687.83 | 3688.00 | 75 | 11.9 |
| 2402 | H-HGEGSFSDELATILEALAAADFIAWLIATKITDKKKKKK-NH2 (SEQ ID NO: 33) | 4256.36 | 4256.88 | 97 | 29.9 |
| 2403 | H-HGEGSFSDELSTILESLAAADFIAWLIATKITDKKKKKK-NH2 (SEQ ID NO: 34) | 4288.35 | 4288.63 | 93 | 48.4 |
| 2404 | H-HGEGSFSDELSTILEALAAADFIAWLIATKITDKKKKKK-NH2 (SEQ ID NO: 35) | 4272.35 | 4272.63 | 92 | 28.5 |
| 2411 | H-HGEGSFSDELATILEALAAADFISWLIATKITDKKKKKK-NH2 (SEQ ID NO: 36) | 4272.35 | 4272.88 | 93 | 35.5 |
| 2412 | H-HGEGSFSDELLTILELLAAADFIAWLIATKITDKKKKKK-NH2 (SEQ ID NO: 37) | 4340.45 | 4341.13 | 88 | 58.7 |
| 2413 | H-HGEGSFSDELATILESLAAADFISWLIATKITDKKKKKK-NH2 (SEQ ID NO: 38) | 4288.35 | 4288.88 | 95 | 52.3 |
| 2414 | H-HGEGSFSDELATILESLAAADFIAWLIATKITD-NH2 (SEQ ID NO: 39) | 3503.78 | 3504.25 | 91 | 49.5 |
| 2415 | H-HGEGSFSDELATILESLAAADFIAWLIATKITDKKKKKK-NH2 (SEQ ID NO: 40) | 4272.35 | 4272.88 | 98 | 43.25 |
| 2416 | H-HGEGSFSDELLTILELLAALDFIAWLIATKITDKKKKKK-NH2 (SEQ ID NO: 41) | 4382.50 | 4383.00 | 88 | 26.5 |
| 2417 | H-HGEGSFSDELATILEALAASDFIAWLIATKITD-NH2 (SEQ ID NO: 42) | 3503.78 | 3504.10 | 98 | 58.8 |

TABLE 1-continued

Compounds synthesized

| ZP no. | Sequence | Mw mono isotopic (g/mol) calculated | Mw mono isotopic (g/mol) found | Purity % | Yield/g resin mg |
|---|---|---|---|---|---|
| 2418 | H-HGEGSFSDELATILEALAAADFISWLIATKITD-NH2 (SEQ ID NO: 43) | 3503.78 | 3504.00 | 97 | 83.3 |
| 2420 | H-HGEGSFSDELSTILEALAAADFIAWLIATKITD-NH2 (SEQ ID NO: 44) | 3503.78 | 3504.63 | 94 | 62.2 |
| 2423 | H-HGEGSFSDELATILEALAASDFIAWLIATKITDKKKKKK-NH2 (SEQ ID NO: 45) | 4272.35 | 4273.50 | 93 | 27.2 |
| 2424 | H-HGEGSFSDELLTILELLAALDFILWLILTKITDKKKKKK-NH2 (SEQ ID NO: 46) | 4466.59 | 4467.00 | 78 | 29 |

Example 1

Synthesis of Compound 2264

H-His-Gly-Glu-Gly-Ser-Phe-Ser-Asp-Glu-Leu-Ala-Thr-Ile-Leu-Glu-Ala-Leu-Ala-Ala-Ala-Asp-Phe-Ile-Ala-Trp-Leu-Ile-Ala-Thr-Lys-Ile-Thr-Asp-NH$_2$ on TentaGel S RAM.

Dry TentaGel S RAM (0.2 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, 413 mg peptide product was collected with a purity better than 93% and the identity of the peptide was confirmed by MS (found M 3488.13, calculated M 3487.79).

Example 2

Synthesis of Compound 2268

H-His-Gly-Glu-Gly-Ser-Phe-Ser-Asp-Glu-Leu-Ala-Thr-Ile-Leu-Glu-Ala-Leu-Ala-Ala-Ser-Asp-Phe-Ile-Ser-Trp-Leu-Ile-Ser-Thr-Lys-Ile-Thr-Asp-NH$_2$ on TentaGel S RAM.

Dry TentaGel S RAM (0.2 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, 132 mg peptide product was collected with a purity better than 91% and the identity of the peptide was confirmed by MS (found M 3535.88, calculated M 3535.77).

Example 3

Synthesis of Compound 2264 (Lys6)

H-His-Gly-Glu-Gly-Ser-Phe-Ser-Asp-Glu-Leu-Ala-Thr-Ile-Leu-Glu-Ala-Leu-Ala-Ala-Ala-Asp-Phe-Ile-Ala-Trp-Leu-Ile-Ala-Thr-Lys-Ile-Thr-Asp-Lys-Lys-Lys-Lys-Lys-Lys NH$_2$ on TentaGel S RAM-Lys(Boc)-Fmoc.

Dry TentaGel S RAM-Lys(Boc)-Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, the peptide product was collected with a purity better than 90% and the identity of the peptide was confirmed by MS (found M 4256.40 calculated M 4256.36).

Example 4

Synthesis of Compound 2268 (Lys6)

H-His-Gly-Glu-Gly-Ser-Phe-Ser-Asp-Glu-Leu-Ala-Thr-Ile-Leu-Glu-Ala-Leu-Ala-Ala-Ser-Asp-Phe-Ile-Ser-Trp-Leu-Ile-Ser-Thr-Lys-Ile-Thr-Asp-Lys-Lys-Lys-Lys-Lys-Lys NH$_2$ on TentaGel S RAM-Lys(Boc)-Fmoc.

Dry TentaGel S RAM-Lys(Boc)-Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, the peptide product was collected with a purity better than 90% and the identity of the peptide was confirmed by MS (found M 4304.10 calculated M 4304.34).

Example 5

Synthesis of Compound 2264 A (Acetate Salt)

Counter ion exchange from trifluoroacetate to acetate of Compound 2264. The purified synthetic peptide product of compound 2264 is isolated as a trifluoroacetate salt, due to the presence of trifluoroacetic acid (0.1% v/v) in the HPLC buffers used for the purification of the crude synthetic peptide product.

In order to exchange the counter ion trifluoroacetate with acetate, a solution of the peptide was passed through a column packed with strong base ion exchange resin on the acetate (Dowex 1×8). Compound 2264T is dissolved in water. The solution is passed through a column containing strong base ion exchange resin on the acetate (Dowex 1×8; capacity 1.33 meq/ml resin). The resin is then washed with water and the eluate is collected and lyophilized resulting in the acetate salt with a purity better than 90%.

Example 6

Synthesis of Compound 2264 C (Chloride Salt)

Counter ion exchange from trifluoroacetate (Tfa) to chloride (Cl—) of Compound 2264. Compound 2264T was dissolved in 0.1 M hydrochloric acid and the resulting solution was lyophilized. The remanence was dissolved in water and lyophilized again resulting in the chloride salt with a purity better than 90%.

Further selective GLP-2 analogue compounds are listed in table 2

TABLE 2

List of selective GLP-2 analogue compounds.

| Compound | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 (SEQ ID NO: 105) | H | G | E | G | S | F | S | D | E | L | A | T | I | L | E | A | L | A |
| 2 (SEQ ID NO: 47) | H | G | E | G | S | F | S | D | E | L | L | T | I | L | E | L | L | A |
| 3 (SEQ ID NO: 48) | H | G | E | G | S | F | S | D | E | L | F | T | I | L | E | F | L | A |
| 4 (SEQ ID NO: 49) | H | G | E | G | S | F | S | D | E | L | V | T | I | L | E | V | L | A |
| 5 (SEQ ID NO: 50) | H | G | E | G | S | F | S | D | E | L | I | T | I | L | E | I | L | A |
| 6 (SEQ ID NO: 106) | H | G | E | G | S | F | S | D | E | L | L | T | I | L | E | L | L | A |
| 7 (SEQ ID NO: 51) | H | G | E | G | S | F | S | D | E | L | I | T | I | L | E | I | L | A |
| 8 (SEQ ID NO: 52) | H | G | E | G | S | F | S | D | E | L | V | T | I | L | E | V | L | A |
| 9 (SEQ ID NO: 107) | H | G | E | G | S | F | S | D | E | L | F | T | I | L | E | F | L | A |
| 10 (SEQ ID NO: 53) | H | G | E | G | S | F | S | D | E | L | A | T | I | L | E | A | L | A |
| 11 (SEQ ID NO: 54) | H | G | E | G | S | F | S | D | E | L | L | T | I | L | E | L | L | A |
| 12 (SEQ ID NO: 55) | H | G | E | G | S | F | S | D | E | L | I | T | I | L | E | I | L | A |
| 13 (SEQ ID NO: 56) | H | G | E | G | S | F | S | D | E | L | V | T | I | L | E | V | L | A |
| 14 (SEQ ID NO: 57) | H | G | E | G | S | F | S | D | E | L | F | T | I | L | E | F | L | A |
| 15 (SEQ ID NO: 108) | H | G | E | G | S | F | S | D | E | L | A | T | I | L | E | A | L | A |
| 16 (SEQ ID NO: 109) | H | G | E | G | S | F | S | D | E | L | A | T | I | L | E | A | L | A |
| 17 (SEQ ID NO: 110) | H | G | E | G | S | F | S | D | E | L | A | T | I | L | E | A | L | A |
| 18 (SEQ ID NO: 111) | H | G | E | G | S | F | S | D | E | L | A | T | I | L | E | A | L | A |
| 19 (SEQ ID NO: 58) | H | G | E | G | S | F | S | D | E | L | A | T | I | L | E | A | L | A |
| 20 (SEQ ID NO: 59) | H | G | E | G | S | F | S | D | E | L | A | T | I | L | E | A | L | A |

TABLE 2-continued

List of selective GLP-2 analogue compounds.

| | | | | | | | | | | | | | | | | | |
|---|---|---|---|---|---|---|---|---|---|---|---|---|---|---|---|---|---|
| 21 (SEQ ID NO: 60) | H | G | E | G | S | F | S | D | E | L | A | T | I | L | E | A | L | A |
| 22 (SEQ ID NO: 112) | H | G | E | G | S | F | S | D | E | L | S | T | I | L | E | S | L | A |
| 23 (SEQ ID NO: 62) | H | G | E | G | S | F | S | D | E | L | A | T | I | L | E | S | L | A |
| 24 (SEQ ID NO: 113) | H | G | E | G | S | F | S | D | E | L | S | T | I | L | E | A | L | A |
| 25 (SEQ ID NO: 61) | H | G | E | G | S | F | S | D | E | L | A | T | I | L | E | S | L | A |
| 26 (SEQ ID NO: 114) | H | G | E | G | S | F | S | D | E | L | S | T | I | L | E | S | L | A |
| 27 (SEQ ID NO: 115) | H | G | E | G | S | F | S | D | E | L | A | T | I | L | E | S | L | A |
| 28 (SEQ ID NO: 63) | H | G | E | G | S | F | S | D | E | L | S | T | I | L | E | A | L | A |
| 29 (SEQ ID NO: 64) | H | G | E | G | S | F | S | D | E | L | A | T | I | L | E | S | L | A |
| 30 (SEQ ID NO: 65) | H | G | E | G | S | F | S | D | E | L | S | T | I | L | E | A | L | A |
| 31 (SEQ ID NO: 66) | H | G | E | G | S | F | S | D | E | L | S | T | I | L | E | A | L | A |
| 32 (SEQ ID NO: 67) | H | G | E | G | S | F | S | D | E | L | S | T | I | L | E | S | L | A |
| 33 (SEQ ID NO: 68) | H | G | E | G | S | F | S | D | E | L | S | T | I | L | E | S | L | A |
| 34 (SEQ ID NO: 69) | H | G | E | G | S | F | S | D | E | L | S | T | I | L | E | S | L | A |
| 35 (SEQ ID NO: 116) | H | G | E | G | S | F | S | D | E | L | S | T | I | L | E | A | L | A |
| 36 (SEQ ID NO: 117) | H | G | E | G | S | F | S | D | E | L | A | T | I | L | E | S | L | A |
| 37 (SEQ ID NO: 70) | H | G | E | G | S | F | S | D | E | L | S | T | I | L | E | S | L | A |
| 38 (SEQ ID NO: 71) | H | G | E | G | S | F | S | D | E | L | S | T | I | L | E | S | L | A |
| 39 (SEQ ID NO: 72) | H | G | E | G | S | F | S | D | E | L | S | T | I | L | E | A | L | A |
| 40 (SEQ ID NO: 73) | H | G | E | G | S | F | S | D | E | L | S | T | I | L | E | S | L | A |
| 41 (SEQ ID NO: 74) | H | G | E | G | S | F | S | D | E | L | S | T | I | L | E | A | L | A |
| 42 (SEQ ID NO: 75) | H | G | E | G | S | F | S | D | E | L | A | T | I | L | E | S | L | A |
| 43 (SEQ ID NO: 76) | H | G | E | G | S | F | S | D | E | L | S | T | I | L | E | A | L | A |
| 44 (SEQ ID NO: 77) | H | G | E | G | S | F | S | D | E | L | A | T | I | L | E | S | L | A |
| 45 (SEQ ID NO: 78) | H | G | E | G | S | F | S | D | E | L | A | T | I | L | E | S | L | A |
| 46 (SEQ ID NO: 79) | H | G | E | G | S | F | S | D | E | L | G | T | I | L | E | G | L | A |

TABLE 2-continued

List of selective GLP-2 analogue compounds.

| | | | | | | | | | | | | | | | | | |
|---|---|---|---|---|---|---|---|---|---|---|---|---|---|---|---|---|---|
| 47 (SEQ ID NO: 80) | H | G | E | G | S | F | S | D | E | L | K | T | I | L | E | K | L | A |
| 48 (SEQ ID NO: 81) | H | G | E | G | S | F | S | D | E | L | E | T | I | L | E | E | L | A |
| 49 (SEQ ID NO: 82) | H | G | E | G | S | F | S | D | E | L | D | T | I | L | E | D | L | A |
| 50 (SEQ ID NO: 83) | H | G | E | G | S | F | S | D | E | L | H | T | I | L | E | H | L | A |
| With K6 | | | | | | | | | | | | | | | | | | |
| 51 (SEQ ID NO: 118) | H | G | E | G | S | F | S | D | E | L | A | T | I | L | E | A | L | A |
| 52 (SEQ ID NO: 119) | H | G | E | G | S | F | S | D | E | L | L | T | I | L | E | L | L | A |
| 53 (SEQ ID NO: 84) | H | G | E | G | S | F | S | D | E | L | F | T | I | L | E | F | L | A |
| 54 (SEQ ID NO: 85) | H | G | E | G | S | F | S | D | E | L | V | T | I | L | E | V | L | A |
| 55 (SEQ ID NO: 86) | H | G | E | G | S | F | S | D | E | L | I | T | I | L | E | I | L | A |
| 56 (SEQ ID NO: 120) | H | G | E | G | S | F | S | D | E | L | L | T | I | L | E | L | L | A |
| 57 (SEQ ID NO: 87) | H | G | E | G | S | F | S | D | E | L | I | T | I | L | E | I | L | A |
| 58 (SEQ ID NO: 88) | H | G | E | G | S | F | S | D | E | L | V | T | I | L | E | V | L | A |
| 59 (SEQ ID NO: 89) | H | G | E | G | S | F | S | D | E | L | F | T | I | L | E | F | L | A |
| 60 (SEQ ID NO: 90) | H | G | E | G | S | F | S | D | E | L | A | T | I | L | E | A | L | A |
| 61 (SEQ ID NO: 91) | H | G | E | G | S | F | S | D | E | L | L | T | I | L | E | L | L | A |
| 62 (SEQ ID NO: 92) | H | G | E | G | S | F | S | D | E | L | I | T | I | L | E | I | L | A |
| 63 (SEQ ID NO: 93) | H | G | E | G | S | F | S | D | E | L | V | T | I | L | E | V | L | A |
| 64 (SEQ ID NO: 94) | H | G | E | G | S | F | S | D | E | L | F | T | I | L | E | F | L | A |
| 65 (SEQ ID NO: 121) | H | G | E | G | S | F | S | D | E | L | A | T | I | L | E | A | L | A |
| 66 (SEQ ID NO: 122) | H | G | E | G | S | F | S | D | E | L | A | T | I | L | E | A | L | A |
| 67 (SEQ ID NO: 123) | H | G | E | G | S | F | S | D | E | L | A | T | I | L | E | A | L | A |
| 68 (SEQ ID NO: 124) | H | G | E | G | S | F | S | D | E | L | A | T | I | L | E | A | L | A |
| 69 (SEQ ID NO: 95) | H | G | E | G | S | F | S | D | E | L | A | T | I | L | E | A | L | A |

TABLE 2-continued

List of selective GLP-2 analogue compounds.

| | | | | | | | | | | | | | | | | | |
|---|---|---|---|---|---|---|---|---|---|---|---|---|---|---|---|---|---|
| 70 (SEQ ID NO: 96) | H | G | E | G | S | F | S | D | E | L | A | T | I | L | E | A | L | A |
| 71 (SEQ ID NO: 97) | H | G | E | G | S | F | S | D | E | L | A | T | I | L | E | A | L | A |

| Compound | 19 | 20 | 21 | 22 | 23 | 24 | 25 | 26 | 27 | 28 | 29 | 30 | 31 | 32 | 33 | HPI |
|---|---|---|---|---|---|---|---|---|---|---|---|---|---|---|---|---|
| 1 (SEQ ID NO: 105) | A | A | D | F | I | A | W | L | I | A | T | K | I | T | D | 9 |
| 2 (SEQ ID NO: 47) | A | L | D | F | I | L | W | L | I | L | T | K | I | T | D | 19 |
| 3 (SEQ ID NO: 48) | A | F | D | F | I | F | W | L | I | F | T | K | I | T | D | 14 |
| 4 (SEQ ID NO: 49) | A | V | D | F | I | V | W | L | I | V | T | K | I | T | D | 21 |
| 5 (SEQ ID NO: 50) | A | I | D | F | I | I | W | L | I | I | T | K | I | T | D | 22.5 |
| 6 (SEQ ID NO: 106) | A | S | D | F | I | S | W | L | I | S | T | K | I | T | D | 5.2 |
| 7 (SEQ ID NO: 51) | A | S | D | F | I | S | W | L | I | S | T | K | I | T | D | 6.6 |
| 8 (SEQ ID NO: 52) | A | S | D | F | I | S | W | L | I | S | T | K | I | T | D | 6 |
| 9 (SEQ ID NO: 107) | A | S | D | F | I | S | W | L | I | S | T | K | I | T | D | 3.2 |
| 10 (SEQ ID NO: 53) | A | G | D | F | I | G | W | L | I | G | T | K | I | T | D | 2.4 |
| 11 (SEQ ID NO: 54) | A | G | D | F | I | G | W | L | I | G | T | K | I | T | D | 6.4 |
| 12 (SEQ ID NO: 55) | A | G | D | F | I | G | W | L | I | G | T | K | I | T | D | 7.8 |
| 13 (SEQ ID NO: 56) | A | G | D | F | I | G | W | L | I | G | T | K | I | T | D | 7.2 |
| 14 (SEQ ID NO: 57) | A | G | D | F | I | G | W | L | I | G | T | K | I | T | D | 4.4 |
| 15 (SEQ ID NO: 108) | A | S | D | F | I | S | W | L | I | S | T | K | I | T | D | 1.2 |
| 16 (SEQ ID NO: 109) | A | A | D | F | I | A | W | L | I | S | T | K | I | T | D | 6.4 |
| 17 (SEQ ID NO: 110) | A | A | D | F | I | S | W | L | I | A | T | K | I | T | D | 6.4 |
| 18 (SEQ ID NO: 111) | A | S | D | F | I | A | W | L | I | A | T | K | I | T | D | 6.4 |
| 19 (SEQ ID NO: 58) | A | A | D | F | I | S | W | L | I | S | T | K | I | T | D | 3.8 |
| 20 (SEQ ID NO: 59) | A | S | D | F | I | S | W | L | I | A | T | K | I | T | D | 3.8 |
| 21 (SEQ ID NO: 60) | A | S | D | F | I | A | W | L | I | S | T | K | I | T | D | 3.8 |
| 22 (SEQ ID NO: 112) | A | S | D | F | I | S | W | L | I | S | T | K | I | T | D | −4 |
| 23 (SEQ ID NO: 62) | A | A | D | F | I | A | W | L | I | A | T | K | I | T | D | 6.4 |

TABLE 2-continued

List of selective GLP-2 analogue compounds.

| | | | | | | | | | | | | | | | |
|---|---|---|---|---|---|---|---|---|---|---|---|---|---|---|---|
| 24 (SEQ ID NO: 113) | A | A | D | F | I | A | W | L | I | A | T | K | I | T | D | 6.4 |
| 25 (SEQ ID NO: 61) | A | S | D | F | I | A | W | L | I | A | T | K | I | T | D | 3.8 |
| 26 (SEQ ID NO: 114) | A | A | D | F | I | A | W | L | I | A | T | K | I | T | D | 3.8 |
| 27 (SEQ ID NO: 115) | A | A | D | F | I | S | W | L | I | A | T | K | I | T | D | 3.8 |
| 28 (SEQ ID NO: 63) | A | S | D | F | I | A | W | L | I | A | T | K | I | T | D | 3.8 |
| 29 (SEQ ID NO: 64) | A | A | D | F | I | A | W | L | I | S | T | K | I | T | D | 3.8 |
| 30 (SEQ ID NO: 65) | A | A | D | F | I | S | W | L | I | A | T | K | I | T | D | 3.8 |
| 31 (SEQ ID NO: 66) | A | A | D | F | I | A | W | L | I | S | T | K | I | T | D | 3.8 |
| 32 (SEQ ID NO: 67) | A | S | D | F | I | S | W | L | I | A | T | K | I | T | D | −1.4 |
| 33 (SEQ ID NO: 68) | A | S | D | F | I | A | W | L | I | S | T | K | I | T | D | −1.4 |
| 34 (SEQ ID NO: 69) | A | A | D | F | I | S | W | L | I | S | T | K | I | T | D | −1.4 |
| 35 (SEQ ID NO: 116) | A | S | D | F | I | S | W | L | I | S | T | K | I | T | D | −1.4 |
| 36 (SEQ ID NO: 117) | A | S | D | F | I | S | W | L | I | S | T | K | I | T | D | −1.4 |
| 37 (SEQ ID NO: 70) | A | S | D | F | I | A | W | L | I | A | T | K | I | T | D | 1.2 |
| 38 (SEQ ID NO: 71) | A | A | D | F | I | A | W | L | I | S | T | K | I | T | D | 1.2 |
| 39 (SEQ ID NO: 72) | A | A | D | F | I | S | W | L | I | S | T | K | I | T | D | 1.2 |
| 40 (SEQ ID NO: 73) | A | A | D | F | I | S | W | L | I | A | T | K | I | T | D | 1.2 |
| 41 (SEQ ID NO: 74) | A | S | D | F | I | A | W | L | I | S | T | K | I | T | D | 1.2 |
| 42 (SEQ ID NO: 75) | A | A | D | F | I | S | W | L | I | S | T | K | I | T | D | 1.2 |
| 43 (SEQ ID NO: 76) | A | S | D | F | I | S | W | L | I | A | T | K | I | T | D | 1.2 |
| 44 (SEQ ID NO: 77) | A | S | D | F | I | A | W | L | I | S | T | K | I | T | D | 1.2 |
| 45 (SEQ ID NO: 78) | A | S | D | F | I | S | W | L | I | A | T | K | I | T | D | 1.2 |
| 46 (SEQ ID NO: 79) | A | G | D | F | I | G | W | L | I | G | T | K | I | T | D | −2 |
| 47 (SEQ ID NO: 80) | A | K | D | F | I | K | W | L | I | K | T | K | I | T | D | −20 |
| 48 (SEQ ID NO: 81) | A | E | D | F | I | E | W | L | I | E | T | K | I | T | D | −18 |

TABLE 2-continued

List of selective GLP-2 analogue compounds.

| # | 1 | 2 | 3 | 4 | 5 | 6 | 7 | 8 | 9 | 10 | 11 | 12 | 13 | 14 | 15 | 16 | value |
|---|---|---|---|---|---|---|---|---|---|---|---|---|---|---|---|---|---|
| 49 (SEQ ID NO: 82) | A | D | D | F | I | D | W | L | I | D | T | K | I | T | D | | −18 |
| 50 (SEQ ID NO: 83) | A | H | D | F | I | H | W | L | I | H | T | K | I | T | D | | −16 |
| With K6 | | | | | | | | | | | | | | | | | |
| 51 (SEQ ID NO: 118) | A | A | D | F | I | A | W | L | I | A | T | K | I | T | D | K6 | 9 |
| 52 (SEQ ID NO: 119) | A | L | D | F | I | L | W | L | I | L | T | K | I | T | D | K6 | 19 |
| 53 (SEQ ID NO: 84) | A | F | D | F | I | F | W | L | I | F | T | K | I | T | D | K6 | 14 |
| 54 (SEQ ID NO: 85) | A | V | D | F | I | V | W | L | I | V | T | K | I | T | D | K6 | 21 |
| 55 (SEQ ID NO: 86) | A | I | D | F | I | I | W | L | I | I | T | K | I | T | D | K6 | 22.5 |
| 56 (SEQ ID NO: 120) | A | S | D | F | I | S | W | L | I | S | T | K | I | T | D | K6 | 5.2 |
| 57 (SEQ ID NO: 87) | A | S | D | F | I | S | W | L | I | S | T | K | I | T | D | K6 | 6.6 |
| 58 (SEQ ID NO: 88) | A | S | D | F | I | S | W | L | I | S | T | K | I | T | D | K6 | 6 |
| 59 (SEQ ID NO: 89) | A | S | D | F | I | S | W | L | I | S | T | K | I | T | D | K6 | 3.2 |
| 60 (SEQ ID NO: 90) | A | G | D | F | I | G | W | L | I | G | T | K | I | T | D | K6 | 2.4 |
| 61 (SEQ ID NO: 91) | A | G | D | F | I | G | W | L | I | G | T | K | I | T | D | K6 | 6.4 |
| 62 (SEQ ID NO: 92) | A | G | D | F | I | G | W | L | I | G | T | K | I | T | D | K6 | 7.8 |
| 63 (SEQ ID NO: 93) | A | G | D | F | I | G | W | L | I | G | T | K | I | T | D | K6 | 7.2 |
| 64 (SEQ ID NO: 94) | A | G | D | F | I | G | W | L | I | G | T | K | I | T | D | K6 | 4.4 |
| 65 (SEQ ID NO: 121) | A | S | D | F | I | S | W | L | I | S | T | K | I | T | D | K6 | 1.2 |
| 66 (SEQ ID NO: 122) | A | A | D | F | I | A | W | L | I | S | T | K | I | T | D | K6 | 6.4 |
| 67 (SEQ ID NO: 123) | A | A | D | F | I | S | W | L | I | A | T | K | I | T | D | K6 | 6.4 |
| 68 (SEQ ID NO: 124) | A | S | D | F | I | A | W | L | I | A | T | K | I | T | D | K6 | 6.4 |
| 69 (SEQ ID NO: 95) | A | A | D | F | I | S | W | L | I | S | T | K | I | T | D | K6 | 3.8 |
| 70 (SEQ ID NO: 96) | A | S | D | F | I | S | W | L | I | A | T | K | I | T | D | K6 | 3.8 |
| 71 (SEQ ID NO: 97) | A | S | D | F | I | A | W | L | I | S | T | K | I | T | D | K6 | 3.8 |

Example 7

Relative Chemical Stability Testing

The compounds, as listed in Table 3, were dissolved in 0.1 M HCl to a nominal concentration of 0.5 mM. The samples were incubated 7 days at 40° C. in the dark and then diluted to a nominal concentration of 0.2 mg/mL and analysed by RP-HPLC for the recovery of the main peak and by LC-MS for confirmation of the identity by mass of the main peak.

The compounds were analyzed in a nominal concentration of 0.2 mg/mL by RP-HPLC and LC-MS on a Phenomenex Gemini C18 column, 3 µm, 110 Å, 3×150 mm with the mobile phase of 0.1% TFA in MQW and in MeCN running stepwise from 25% to 48% MeCN over 39 minutes. Flow rate was 0.400 mL/min. The column oven temperature was 50° C., the auto sampler temperature was 4° C. and the UV detection was measured at 220 nm.

The results for the recovery of purity are listed in Table 3.

TABLE 3

Recovery of purity for ZP Compound.

| ZP No. | Recovery (%) |
|---|---|
| 2242 | 87 |
| 2263 | 95 |
| 2264 | * |
| 2266 | 73 |
| 2267 | * |
| 2268 | * |
| 2269 | 39 |
| 2270 | 52 |
| 2272 | * |

* Eluted in the washing phase at analytical RP-HPLC. Repeated data shown in example 7 with a modified analytical RP-HPLC method.

Four compounds (ZP2264, ZP2267, ZP2268 and ZP2272) were eluted late in the washing phase by this analytical method and an experiment was repeated with these four compounds by a modified method as described in the following.

Example 8

Relative Chemical Stability Testing

The compounds, as listed in Table 4, were dissolved in 0.1 M HCl to a nominal concentration of 0.25 mM. The samples were incubated 2 days at 40° C. in the dark and then diluted to a nominal concentration of 0.2 mg/mL and analysed by RP-HPLC for the recovery of the main peak.

The compounds were analyzed in a nominal concentration of 0.2 mg/mL by RP-HPLC and LC-MS on a Phenomenex Gemini C18 column, 3 µm, 110 Å, 3×150 mm with the mobile phase 0.1% TFA in MQW and in MeCN running stepwise from 25% to 80% MeCN over 39 minutes. Flow rate was 0.400 mL/min. The column oven temperature was 50° C., the auto sampler temperature was 4° C. and the UV detection was measured at 220 nm.

The results for the recovery of purity are listed in Table 4.

TABLE 4

Recovery of purity for ZP Compound.

| ZP No. | Recovery (%) |
|---|---|
| 1846 | 95 |
| 2264 | 61 |
| 2267 | 61 |
| 2268 | 62 |
| 2272 | 61 |

Example 9

In Vitro Screening of GLP-2 Analogues for Agonism on the GLP-2 Receptor Recombinantly Expressed in BHK-21 Cells *)

The screening was done using BHK21 cells transiently transfected with GLP-2 receptor and the CRE-luciferase reporter gene construct. Dose-response curves and $EC_{50}$ values were determined using seven concentrations from 10 fM to 10 nM and triplicate points for each concentration. Control peptide was used on all test plates.

*) The test was performed by AMRI at Budapest, Hungary

Materials and Methods

Materials and Cells Used:

Nunc or Greiner Tissue culture flasks
Nunc or Greiner 10 cm TC Petri dishes (Nunc 172931)
Nunc or Greiner 96-well plates for daughter plates (Nunc 167008)
BHK-21(C13) cells
White 96-well plates (PerkinElmer 6005680)Deep-well plates for dilutions (Nunc 278752)
Glasgow MEM (Sigma G5154)
Phenol red-free DMEM (Invitrogen/Gibco 31053-028)
Fetal calf serum (FCS, Invitrogen/Gibco Zealand batch)
Nonessential amino acids (100×) (Invitrogen/Gibco 11140-035)
200 mM Glutamine (100×) (Invitrogen/Gibco 25030-024)
Penicillin/Streptomycin (100×) (Invitrogen/Gibco 15140-122)
Sodium pyruvate (100×) (Invitrogen/Gibco 11360-039)
D-PBS (Invitrogen/Gibco 14190-094)
1× Trypsin-EDTA solution (Invitrogen/Gibco 25300-054)
Opti-MEM (Invitrogen/Gibco 31985-047)
Lipofectamine 2000 (Invitrogen 11668-027)
CRE-luc vector (Zealand batch)
hGLP2R vector (Zealand batch)
10% (w/v) sterile BSA in DMEM (Sigma 05488)
10 mM (200×) IBMX in DMEM (Sigma I5879)
LucLite kit (Perkin Elmer 6016911)
Topseal-A (Perkin Elmer 6005185)

Media and Buffers

Growth Medium for BHK-21(C13) Cells:
Glasgow MEM+2 mM glutamine (1:100)+10% FCS+1% NEAA+1% Pen/Strep+1 mM sodium pyruvate (1:100).

Antibiotics-Free Transfection Medium for BHK-21(C13) Cells:
Glasgow MEM+2 mM glutamine (1:100)+1% NEAA+1 mM sodium pyruvate (1:100)

Post-Transfection Medium for BHK-21(C13) Cells:
Glasgow MEM+2 mM glutamine (1:100)+0.2% FCS+1% NEAA+1% Pen/Strep+1 mM sodium pyruvate (1:100)

Coating Solution:
D-PBS+1% BSA

Peptide Dissolution Buffer:
D-PBS+0.1% BSA

Stimulation Buffer:
Phenol red-free DMEM+2 mM glutamine (1:100)+50 µM IBMX+0.3% BSA Protocol for Screening of Peptides on Transfected BHK21(C13) Cells BHK-21 cells are seeded in 10 cm TC-Petri dishes and grown to 70-80% confluency. Subsequently, medium is changed to serum-free transfection medium. DNA (7.5 µg hGLP-2 receptor vector and 7.5 µg CRE-luciferase vector) and Lipofectamine 2000 are diluted in OptiMEM, combined, and added to the cells after 20-30 min. Cells are incubated in the incubator at 37° C., 5% $CO_2$ for 4 hr, trypsinized, and reseeded at 35,000 cells per well in 96-well plates. Cells are incubated overnight in full growth medium in order to allow expression of the transgenes. All plates used for the preparation of diluted GLP-2 analogue solutions are pre-coated with 1% BSA in phosphate-buffered saline for 2 hr and dried overnight. GLP-2 analogues are dissolved in PBS/0.1% BSA to 250 μM and diluted in two steps to 10 μM and 100 nM, respectively, in phenol red- and serum-free medium containing phosphodiesterase inhibitor and 0.3% BSA (stimulation buffer). Thereafter, GLP-2 analogues are serially diluted in the same stimulation buffer to yield concentrations from 10 nM down to 10 fM. Baseline activity is controled with stimulation buffer alone. These solutions are pre-warmed to 37° C. for 30 min. Cells are rinsed with pre-warmed (37° C.) stimulation buffer, and incubated with 100 μl of the pre-warmed peptide dilutions and control for 5 hr at 37° C., 5% $CO_2$. The LucLite enzyme substrate/lysis buffer is prepared shortly before the end of the incubation. 100 μl LucLite substrate are added to each well, and light emission is counted on a suitable counter (e.g. Wallac VictorII). EC50 values are derived from the raw data by fitting with a four parameter logistic equation (Microcal Origin 5.0 or GraphPad 4).

Results are listed in table 5

TABLE 5

| Screening of GLP-2 analogues on GLP-2 receptor-expressing BHK21 cells | | | | | | | | | |
|---|---|---|---|---|---|---|---|---|---|
| ZP ID | 2263 | 2264 | 2266 | 2267 | 2268 | 2269 | 2270 | 2272 | 2242 |
| pEC50 | 10.84 | 11.5 | 9.253 | 10.87 | 11.21 | 10.04 | 10.23 | 11.27 | 12.41 |
| SEM | 0.1929 | 0.2419 | 0.2272 | 0.3139 | 0.2239 | 0.09546 | 0.1449 | 0.1668 | 0.1971 |

Conclusion: The result clearly indicates that all the tested compounds are GLP-2 agonists Example 10

In Vivo Test, Stimulation of Intestinal Growth as Determined in Male C57BL Mice

The ability of the present compounds (ZP2264, ZP2266, ZP2267, ZP2268, ZP2242, ZP2269, ZP2270, ZP2272 and ZP2242) to selectively stimulate small intestinal mass, relative to colon mass was determined in male C57BL mice. Individual groups (n=6-10) of mice were given 800 nmol/kg of each compound, s.c, once daily for three consecutive days. For comparison purposes other groups of animals were given either an equimolar dose of [Gly2]GLP-2 (ZP1559) or vehicle (phosphate buffered saline, pH 7.4) in the same dosing regimen Twenty-four hours after the last dose of compound had been given the mice were sacrificed and the small intestine (from the pylorus to the cecum) and the colon (intestine distal to cecum) was emptied and weighed.

To correct for slight difference in body weight (BW), the organ mass of the small intestine (SI) and colon were expressed relative to BW. The non-selective reference compound [Gly2]GLP-2 has been reported to stimulate gastrointestinal growth in both esophagus, stomach, small intestine and colon and to evaluate differences in growth pattern induced by compounds, the small intestine-colon sensitivity index of compound X was calculated as:

$$(SI/\text{Colon})_X / (SI/\text{Colon})_{[Gly2]GLP-2} \%$$

Compounds with a small intestine-colon sensitivity greater than or equal to 1.10 were considered relatively selective for the small intestine.

TABLE 6

List of the small intestine-colon sensitivity index of test compounds, relative to the reference compound [Gly2]GLP-2.

| | Position | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| Reference compound | | | | | | | | | | | | | | | | | | | |
| [Gly2]GLP-2 (SEQ ID NO: 98) | H | G | D | G | S | F | S | D | E | M | N | T | I | L | D | N | L | A | A |

TABLE 6-continued

List of the small intestine-colon sensitivity index of test compounds, relative to the reference compound [Gly2]GLP-2.

Small intestine selective compounds

| | | | | | | | | | | | | | | | | | | | |
|---|---|---|---|---|---|---|---|---|---|---|---|---|---|---|---|---|---|---|---|
| ZP2264 (SEQ ID NO: 125) | H | G | E | G | S | F | S | D | E | L | A | T | I | L | E | A | L | A | A |
| ZP2268 (SEQ ID NO: 126) | H | G | E | G | S | F | S | D | E | L | A | T | I | L | D | N | L | A | A |

| | Position | | | | | | | | | | | | | | Small intestine-colon sensitivity index |
|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | |

Reference compound

| | | | | | | | | | | | | | | | |
|---|---|---|---|---|---|---|---|---|---|---|---|---|---|---|---|
| [Gly2]GLP-2 (SEQ ID NO: 98) | R | D | F | I | N | W | L | I | Q | T | K | I | T | D | OH | $1.00 \pm 0.02$ |

Small intestine selective compounds

| | | | | | | | | | | | | | | | | |
|---|---|---|---|---|---|---|---|---|---|---|---|---|---|---|---|---|
| ZP2264 (SEQ ID NO: 125) | A | D | F | I | A | W | L | I | A | T | K | I | T | D | NH2 | $1.15 \pm 0.03$* |
| ZP2268 (SEQ ID NO: 126) | R | D | F | I | S | W | L | I | S | T | K | I | T | D | NH2 | $1.10 \pm 0.03$* |

NT indicates "not tested".
*$P < 0.05$, vs [Gly2]GLP-2

TABLE 7

Effect of the test compounds on small intestine and colon mass, relative to the reference compound [Gly2]GLP-2.

| | Position | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| [Gly2]GLP-2 (SEQ ID NO: 127) | H | G | D | G | S | F | S | D | E | M | N | T | I | L | D | N | L | A | A | R | D |
| ZP2263 (SEQ ID NO: 128) | H | G | E | G | S | F | S | D | E | L | S | T | I | L | E | S | L | A | A | S | D |
| ZP2264 (SEQ ID NO: 129) | H | G | E | G | S | F | S | D | E | L | A | T | I | L | E | A | L | A | A | A | D |
| ZP2266 (SEQ ID NO: 130) | H | G | E | G | S | F | S | D | E | L | E | T | I | L | E | E | L | A | A | E | D |
| ZP2267 (SEQ ID NO: 100) | H | G | E | G | S | F | S | D | E | L | S | T | I | L | D | N | L | A | A | R | D |
| ZP2268 (SEQ ID NO: 99) | H | G | E | G | S | F | S | D | E | L | A | T | I | L | D | N | L | A | A | R | D |
| ZP2269 (SEQ ID NO: 101) | H | G | E | G | S | F | S | D | E | L | K | T | I | L | D | N | L | A | A | R | D |
| ZP2270 (SEQ ID NO: 102) | H | G | E | G | S | F | S | D | E | L | N | T | I | L | D | N | L | A | A | R | D |
| ZP2272 (SEQ ID NO: 103) | H | G | E | G | S | F | S | D | E | L | A | T | I | L | D | N | L | A | A | R | D |
| ZP2242 (SEQ ID NO: 104) | H | G | E | G | S | F | S | S | E | L | S | T | I | L | D | A | L | A | A | R | D |

TABLE 7-continued

Effect of the test compounds on small intestine and colon mass, relative to the reference compound [Gly2]GLP-2.

| | Position | | | | | | | | | | | | | SI (% vs. [Gly2]GLP-2) | Colon |
|---|---|---|---|---|---|---|---|---|---|---|---|---|---|---|---|
| | 22 | 23 | 24 | 25 | 26 | 27 | 28 | 29 | 30 | 31 | 32 | 33 | | | |
| [Gly2]GLP-2 (SEQ ID NO: 127) | F | I | N | W | L | I | Q | T | K | I | T | D | | OH | 100 ± 1 | 100 ± 2 |
| ZP2263 (SEQ ID NO: 128) | F | I | S | W | L | I | S | T | K | I | T | D | | NH2 | NT | NT |
| ZP2264 (SEQ ID NO: 129) | F | I | A | W | L | I | A | T | K | I | T | D | | NH2 | 126 ± 3* | 109 ± 3* |
| ZP2266 (SEQ ID NO: 130) | F | I | E | W | L | I | E | T | K | I | T | D | | NH2 | 95 ± 1 | 101 ± 2 |
| ZP2267 (SEQ ID NO: 100) | F | I | A | W | L | I | A | T | K | I | T | D | | NH2 | 108 ± 2 | 109 ± 4 |
| ZP2268 (SEQ ID NO: 99) | F | I | S | W | L | I | S | T | K | I | T | D | | NH2 | 124 ± 3* | 112 ± 4* |
| ZP2269 (SEQ ID NO: 101) | F | I | E | W | L | I | Q | T | K | I | T | D | | NH2 | 97 ± 2 | 95 ± 3 |
| ZP2270 (SEQ ID NO: 102) | F | I | S | W | L | I | S | T | K | I | T | D | | NH2 | NT | NT |
| ZP2272 (SEQ ID NO: 103) | F | I | S | W | L | 1 | A | T | K | I | T | D | | NH2 | 118 ± 2 | 105 ± 6 |
| ZP2242 (SEQ ID NO: 104) | F | I | A | W | L | 1 | A | T | K | I | T | D | K | OH | 111 ± 2 | 107± 3 |

NT indicates "not tested".
*P < 0.05, vs [Gly2]GLP-2

Results

Figure 2:
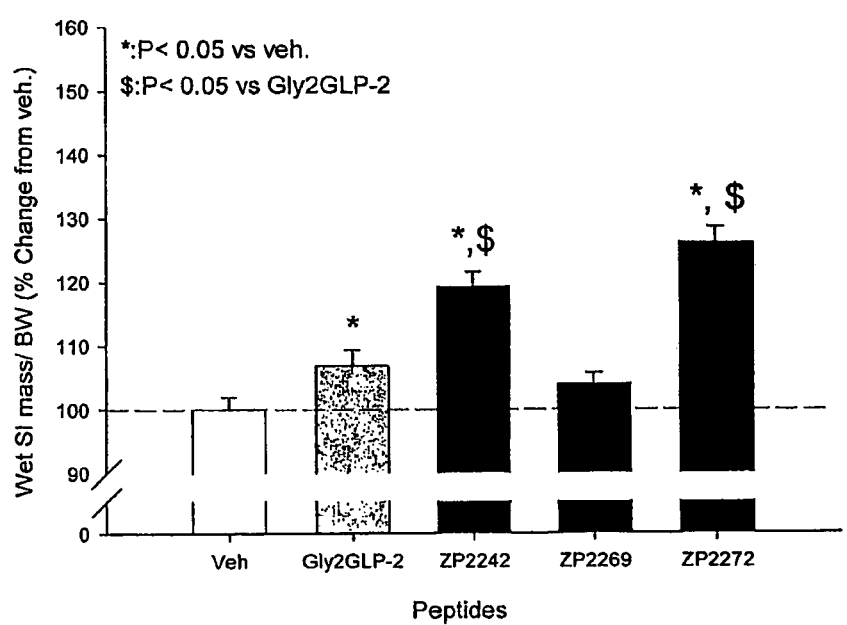
Figure 3:
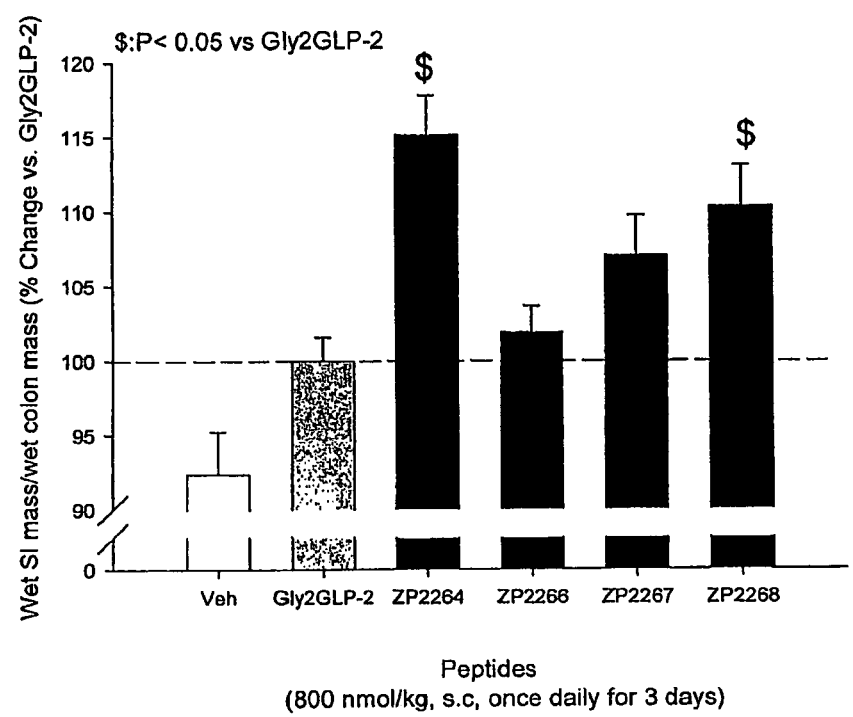
Figure 4:
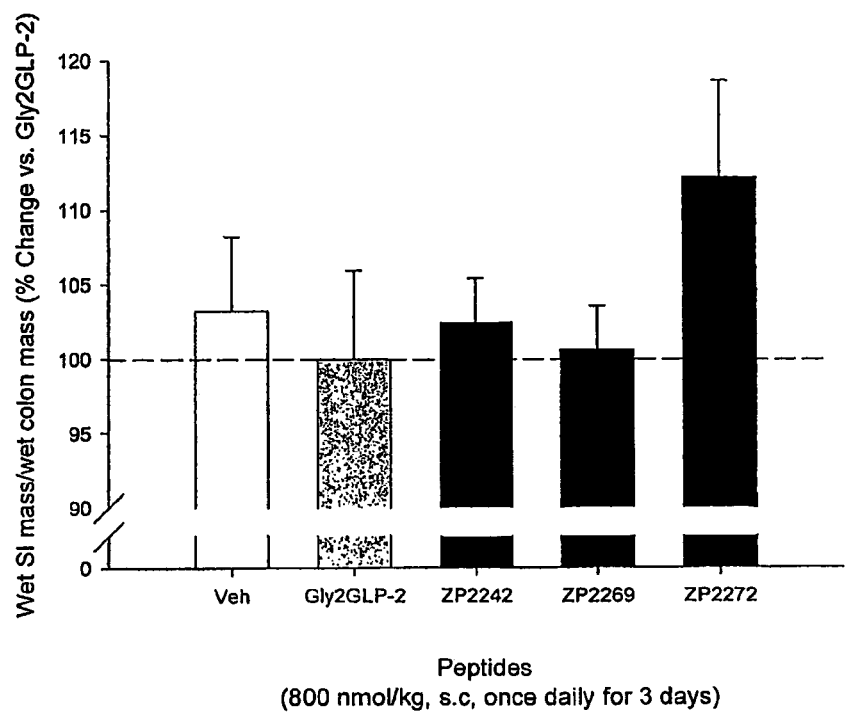
Figure 5:
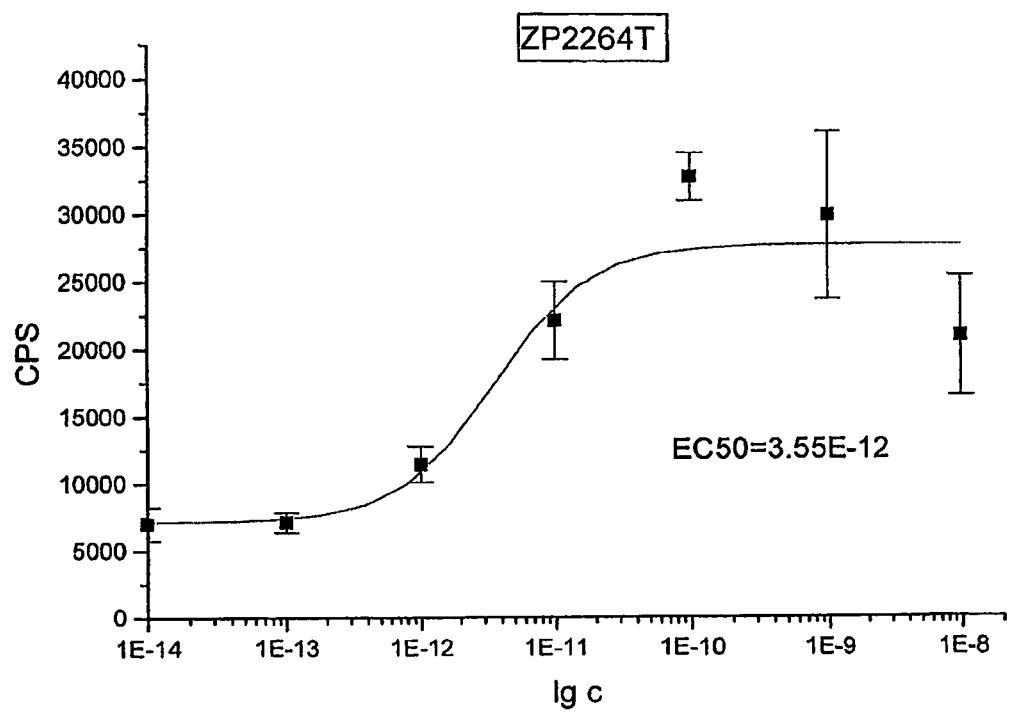
FIG. 5. In vitro screening of ZP2264 for agonism on the GLP-2 receptor recombinantly expressed in BHK-21 cells. The IC 50 of ZP2264 was 3.55E-12, well within the range defined for agonists.

The effects of the test compounds according to the invention were determined based on the ability of the peptides to selectively increase small intestinal mass, relative to colon mass. In FIGS. 1 and 2 relative small intestinal mass vs. vehicle controls following the administration of the reference compound, [Gly2]GLP-2 and ZP2264, ZP2266, ZP2267, ZP2268, ZP2242, ZP2269 and ZP2272 is shown. In FIGS. 3 and 4 the effect of the test compounds on the ratio of small intestine mass to colon mass, vs. that of the reference compound, [Gly2]GLP-2 is shown. The ratio of small intestine mass to colon mass, in the animals given [Gly2]GLP-2 was standardised to 100%. The test compounds that were selective for the small intestine, based on the calculated small intestine-colon sensitivity index of, vs. that of the reference compound, [Gly2]GLP-2, is shown in Table 6. In the animals given [Gly2]GLP-2 the small intestine-colon sensitivity index is standardised to 1. The effect of the test compounds on small intestine and colon mass, relative to the reference compound [Gly2]GLP-2 is shown in Table 7. In the animals given [Gly2]GLP-2 small intestine and colon mass was standardised to 100%.

Example 11

In Vivo Test, Stimulation of Intestinal Growth as Determined in Male C57BL Mice

The ability of further compounds to selectively stimulate small intestinal mass, relative to colon mass was determined in male C57BL mice. A similar protocol was used to that described above in Example 10 except that 200 nmol/kg of each compound was administered per day. Thus, individual groups (n=6-10) of mice were given 200 nmol/kg of each compound, s.c, once daily for three consecutive days. Other groups of animals were given either an equimolar dose of [Gly2]GLP-2 (reference compound) or vehicle (phosphate buffered saline, pH 7.4; negative controls) in the same dosing regimen. Twenty-four hours after the last dose of compound the mice were sacrificed and the stomach, small intestine and the colon emptied and weighed.

Figure 6:
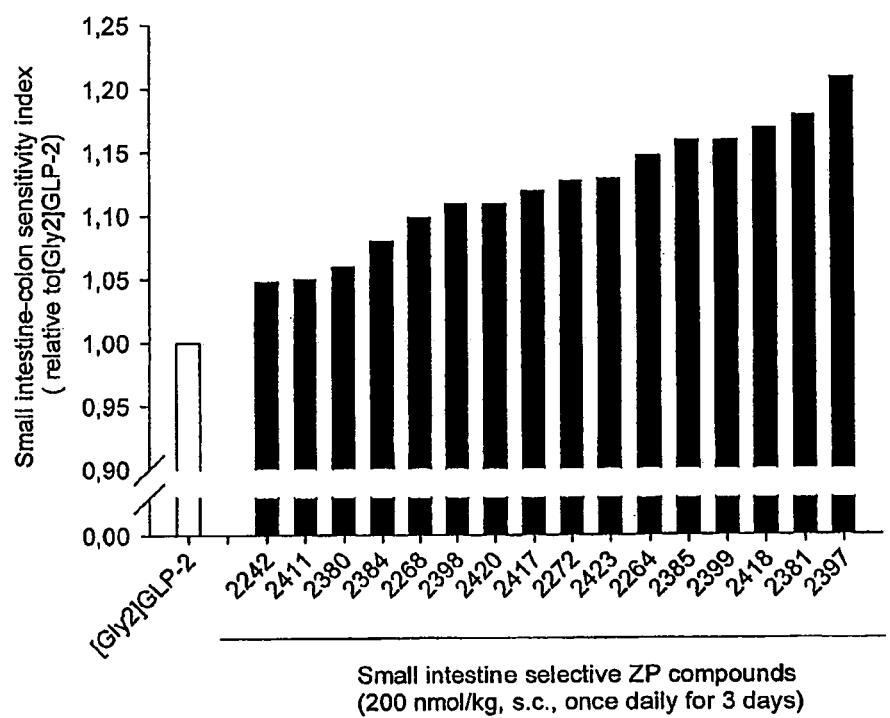
FIG. 6. SmaI intestine/colon sensitivity index of ZP compounds selective for the small intestine.

As shown in FIG. 6, compounds ZP2380, ZP2381, ZP2384, ZP2385, ZP2397, ZP2398, ZP2399, ZP2411, ZP2417, ZP2418, ZP2420, ZP2423, according to the invention, have the ability to selectively increase small intestinal mass, relative to colon mass.

Example 12

In Vivo Test, Stimulation of Stomach Growth as Determined in Male C57BL Mice

The effects of the test compounds according to the invention were determined based on the ability of the peptides to selectively increase stomach mass, relative to vehicle control. The ability of the present compounds (ZP2395, ZP2396, ZP2400, ZP2412, ZP2394 and ZP2401) to selectively stimulate stomach mass, relative to colon mass was determined in male C57BL mice. Individual groups (n=6-10) of mice were given 200 nmol/kg of each compound, s.c, once daily for three consecutive days. For comparison purposes other groups of animals were given either an equimolar dose of

Figure 7:
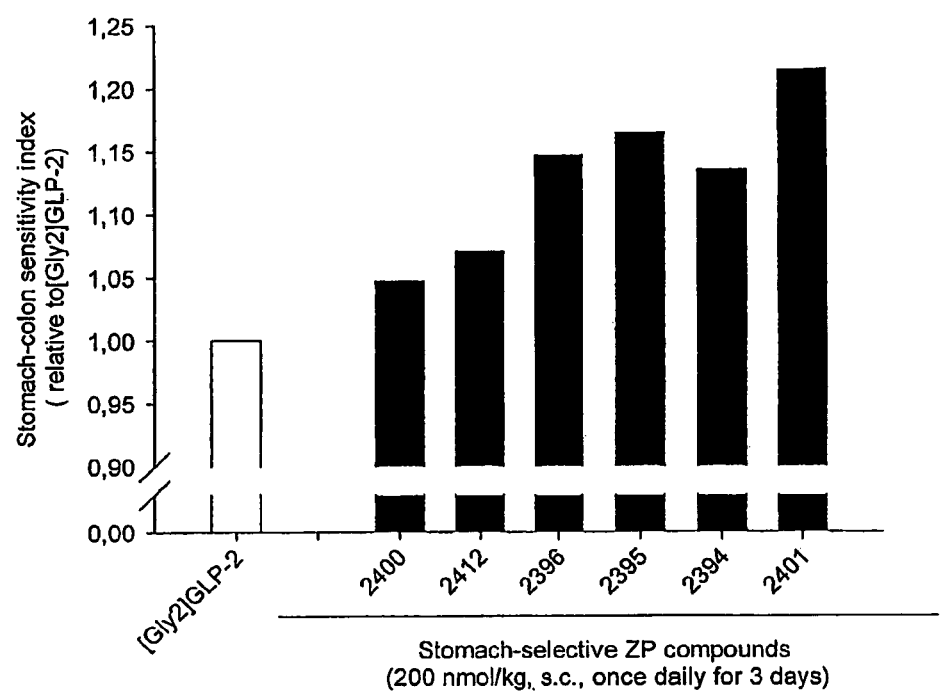
FIG. 7. Stomach/colon sensitivity index of ZP compounds selective for the stomach.

[Gly2]GLP-2 or vehicle (phosphate buffered saline, pH 7.4) in the same dosing regimen. Twenty-four hours after the last dose of compound had been given the mice were sacrificed and the stomach and small intestine (from the pylorus to the ileocaecal junction) emptied and weighed. To correct for slight difference in body weight (BW), the organ mass of the stomach is presented relative to BW. In FIG. 7 it is shown that compounds ZP2395, ZP2396, ZP2400, ZP2412, ZP2414, ZP2416, ZP2394 and ZP2401 have the ability to selectively increase stomach mass, relative to colon mass.

The reference compound, [Gly2]GLP-2, has not been reported to stimulate stomach mass, whereas a number of the ZP compounds increased stomach mass relative to bodyweight (FIG. 7). To evaluate the differential growth pattern induced by ZP compounds, compared to [Gly2]GLP-2, on the stomach, the stomach-colon sensitivity index of compound X was calculated as:

$$(Stomach/Colon)_X / Stomach/(Colon)_{[Gly2]GLP-2}\%$$

Compounds with a stomach/colon sensitivity greater than or equal to 1.05 were considered relatively selective for the stomach.

Figure 8:
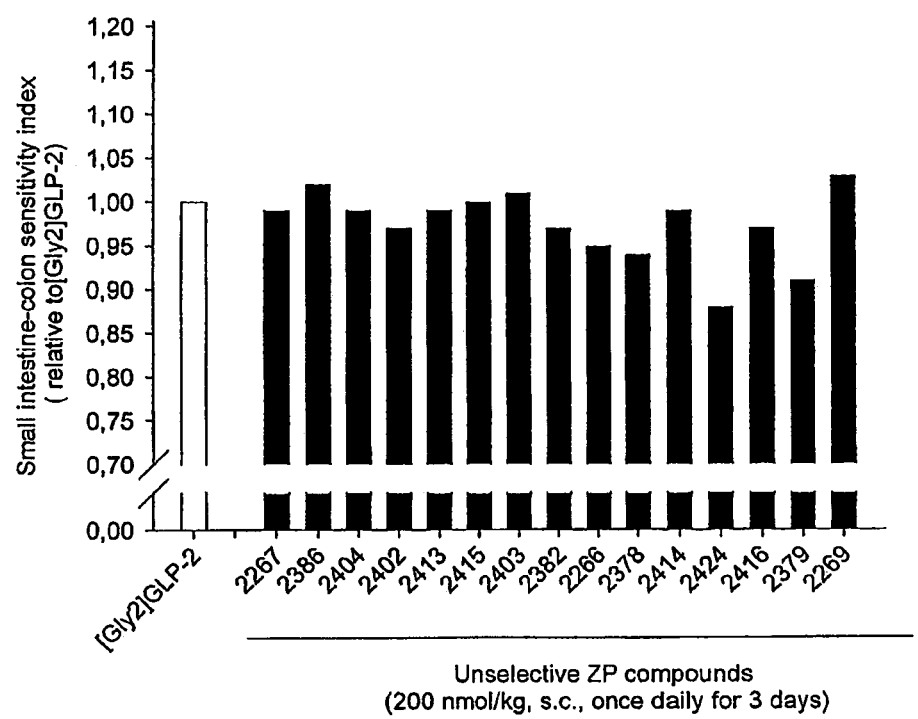
FIG. 8. Small intestine/colon sensitivity index of unselective ZP compounds.

The compounds ZP2267, ZP2386, ZP2404, ZP2413, ZP1415, ZP2402, ZP2403, ZP2382, ZP2266, ZP2378, ZP2414, ZP2416, ZP2424, ZP2379, ZP2269 are unselective for the small intestine, colon or stomach (FIG. 8).

Table 8 shows a summary of data obtained in Examples 10 to 12:

TABLE 8

Summary of data

| | Compared to 1559 in % | | | | |
|---|---|---|---|---|---|
| ZP no. | SI-BW | Colon-BW | Sto-BW | Sensitivity index Si/Colon | Sensitivity index Stomach/Co | |
| 2267 | 108.5 | 109.4 | 85.9 | 0.99 | 0.79 | Non specific peptides |
| 2386 | 113 | 111 | 95 | 1.02 | 0.86 | |
| 2404 | 114 | 115 | 103 | 0.99 | 0.90 | |
| 2402 | 110 | 113 | 102 | 0.97 | 0.90 | |
| 2413 | 116 | 117 | 108 | 0.99 | 0.92 | |
| 2415 | 106 | 106 | 100 | 1.00 | 0.94 | |
| 2403 | 110 | 109 | 107 | 1.01 | 0.98 | |
| 2382 | 103 | 106 | 101 | 0.97 | 0.95 | |
| 2266 | 95.3 | 100.6 | 93.6 | 0.95 | 0.93 | |
| 2378 | 91 | 97 | 94 | 0.94 | 0.97 | |
| 2414 | 105 | 106 | 110 | 0.99 | 1.04 | |
| 2424 | 86 | 98 | 91 | 0.88 | 0.93 | |
| 2416 | 89 | 92 | 96 | 0.97 | 1.04 | |
| 2379 | 88 | 97 | 99 | 0.91 | 1.02 | |
| 2269 | 97.4 | 94.7 | 99.8 | 1.03 | 1.05 | |
| 2400 | 106 | 106 | 111 | 1.00 | 1.05 | Stomach specific peptides |
| 2412 | 94 | 99 | 106 | 0.95 | 1.07 | |
| 2396 | 104 | 102 | 117 | 1.02 | 1.15 | |
| 2395 | 98 | 97 | 113 | 1.01 | 1.16 | |
| 2394 | 105 | 96 | 109 | 1.09 | 1.14 | |
| 2401 | 98 | 88 | 107 | 1.11 | 1.22 | |
| 2242 | 111.7 | 106.6 | 99.6 | 1.05 | 0.93 | Small intestine specific |
| 2411 | 117 | 111 | 106 | 1.05 | 0.95 | |
| 2380 | 108 | 102 | 98 | 1.06 | 0.96 | |
| 2384 | 128 | 118 | 100 | 1.08 | 0.85 | |
| 2268 | 123.6 | 112.5 | 87.4 | 1.10 | 0.78 | |
| 2398 | 108 | 97 | 102 | 1.11 | 1.05 | |
| 2420 | 112 | 101 | 90 | 1.11 | 0.89 | |
| 2417 | 119 | 106 | 90 | 1.12 | 0.85 | |
| 2272 | 118.1 | 104.7 | 96 | 1.13 | 0.92 | |
| 2423 | 123 | 109 | 94 | 1.13 | 0.86 | |
| 2264 | 125.7 | 109.5 | 87 | 1.15 | 0.79 | |
| 2385 | 110 | 95 | 93 | 1.16 | 0.98 | |
| 2399 | 119 | 103 | 115 | 1.16 | 1.12 | |
| 2418 | 117 | 100 | 91 | 1.17 | 0.91 | |
| 2381 | 123 | 104 | 92 | 1.18 | 0.88 | |
| 2397 | 122 | 101 | 109 | 1.21 | 1.08 | |
| 2263 | NT | NT | NT | | | |
| 2270 | NT | NT | NT | | | |
| 2383 | NT | NT | NT | | | |

* NT: Not Tested

GLP-2 Receptor Specificity.

The mechanisms by which substrates appear to achieve biological specificity towards a given receptor involves various interactions between the substrate and the receptor based on hydrogen bonding, hydrophobic, electrostatic interactions etc.

During our Structure-Activity Relationship-studies it has appeared that the residues in the positions 11, 16, 20, 24 and 28 in the GLP-2 sequence are deeply involved in the recognition and binding to the GLP-2 receptor. Thus altering the amino acid pattern of these particular positions divides the GLP-2 analogues into three different groups: small intestine-, stomach- and non-specific peptides.

The receptor specificity of the GLP-2 analogues was found to depend on the hydrophobicity and the hydrogen bonding potential of the amino acids in position 11, 16, 20, 24 and 28.

Example 13

Effect of HPI on Small Intestine Specificity

In table 9 HPI data is shown for the GLP-2 peptides which are small intestine specific according to the SI/Colon-sensitivity index.

TABLE 9

Small Intestine specific GLP-2 analogues - Hydrophaticity Profile (HPP)

| ZP no. | SI-BW | Colon-BW | Sto-BW | Sensitivity index Si/Colon | Sensitivity index Stomach/Co | \multicolumn{5}{c}{Sequence} | | | | | \multicolumn{5}{c}{HPI} | | | | | HPP |
|---|---|---|---|---|---|---|---|---|---|---|---|---|---|---|---|---|
| | | | | | | 11 | 16 | 20 | 24 | 28 | 11 | 16 | 20 | 24 | 28 | |
| 2242 | 111.7 | 106.6 | 99.6 | 1.05 | 0.93 | S | A | R | A | A | −0.8 | 1.8 | −4.5 | 1.8 | 1.8 | 0.1 |
| 2411 | 117 | 111 | 106 | 1.05 | 0.95 | A | A | A | S | A | 1.8 | 1.8 | 1.8 | −0.8 | 1.8 | 6.4 |
| 2380 | 108 | 102 | 98 | 1.06 | 0.96 | S | S | S | S | S | −0.8 | −0.8 | −0.8 | −0.8 | −0.8 | −4 |
| 2384 | 128 | 118 | 100 | 1.08 | 0.85 | A | A | A | A | S | 1.8 | 1.8 | 1.8 | 1.8 | −0.8 | 6.4 |
| 2268 | 123.6 | 112.5 | 87.4 | 1.10 | 0.78 | A | A | S | S | S | 1.8 | 1.8 | −0.8 | −0.8 | −0.8 | 1.2 |
| 2398 | 108 | 97 | 102 | 1.11 | 1.05 | S | A | S | S | S | −0.8 | 1.8 | −0.8 | −0.8 | −0.8 | −1.4 |
| 2420 | 112 | 101 | 90 | 1.11 | 0.89 | S | A | A | A | A | −0.8 | 1.8 | 1.8 | 1.8 | 1.8 | 6.4 |
| 2417 | 119 | 106 | 90 | 1.12 | 0.85 | A | A | S | A | A | 1.8 | 1.8 | −0.8 | 1.8 | 1.8 | 6.4 |
| 2272 | 118.1 | 104.7 | 96 | 1.13 | 0.92 | A | S | A | S | A | 1.8 | −0.8 | 1.8 | −0.8 | 1.8 | 3.8 |
| 2423 | 123 | 109 | 94 | 1.13 | 0.86 | A | A | S | A | A | 1.8 | 1.8 | −0.8 | 1.8 | 1.8 | 6.4 |
| 2264 | 125.7 | 109.5 | 87 | 1.15 | 0.79 | A | A | A | A | A | 1.8 | 1.8 | 1.8 | 1.8 | 1.8 | 9 |
| 2385 | 110 | 95 | 93 | 1.16 | 0.98 | S | A | S | S | S | −0.8 | 1.8 | −0.8 | −0.8 | −0.8 | −1.4 |
| 2399 | 119 | 103 | 115 | 1.16 | 1.12 | A | S | S | S | S | 1.8 | −0.8 | −0.8 | −0.8 | −0.8 | −1.4 |
| 2418 | 117 | 100 | 91 | 1.17 | 0.91 | A | A | A | S | A | 1.8 | 1.8 | 1.8 | −0.8 | 1.8 | 6.4 |
| 2381 | 123 | 104 | 92 | 1.18 | 0.88 | A | A | S | S | S | 1.8 | 1.8 | −0.8 | −0.8 | −0.8 | 1.2 |
| 2397 | 122 | 101 | 109 | 1.21 | 1.08 | A | A | A | A | S | 1.8 | 1.8 | 1.8 | 1.8 | −0.8 | 6.4 |

The data shows that the HPI interval for the individual positions 11, 16, 20, 24 and 28 for the small intestine specific GLP-2 analogues should independently for position 11 and 16 be at least −0.8≤HPI≤3.8 or preferably −0.8≤HPI≤2.8 or more preferred HPI=1.8.

For position 20, 24 and 28 the HPI interval should for the individual positions independently be at least −0.8≤HPI$_{20,24,28}$≤1.8 or preferably −0.8≤HPI$_{20}$≤1.8 and more preferably HPI$_{24,28}$=−0.8.

Possible amino substitution patterns for small intestine-selective peptides according to HPI-intervals are shown in table 10.

TABLE 10

Small Intestine specific GLP-2 analogues - Hydrophaticity Profile (HPP)
Small intestine specific GLP-2 analogues

| HPP | 11 | 16 | 20 | 24 | 28 | HPP |
|---|---|---|---|---|---|---|
| preferred | A | A | A | A | A | |
| | S | S | S | S | S | |
| | G | G | G | G | G | |
| | T | T | T | T | T | −4-9 |
| more preferred | A | A | A | A | A | |
| | S | S | S | S | S | |
| | | | G | G | G | |
| | | | T | T | T | −4-9 |

TABLE 10-continued

Small Intestine specific GLP-2 analogues - Hydrophaticity Profile (HPP)
Small intestine specific GLP-2 analogues

| HPP | 11 | 16 | 20 | 24 | 28 | HPP |
|---|---|---|---|---|---|---|
| most preferred | A | A | A | A | A | |
| | | | S | S | S | 1.2-9 |

Thus each of X11, X16, X20, X24 and X28 may independently be Ala, Ser, Gly or Thr. In particular, each of X11 and X16 may independently be Ala or Ser, and X20, X24 and X28 may independently be Ala, Ser, Gly or Thr. For example, X11 and X16 may both be Ala, and X20, X24 and X28 may independently be Ala, Ser, Gly or Thr.

Example 14

Effect of HPI on Stomach Specificity

In table 11 HPI data is shown for the GLP-2 peptides which are stomach-specific according to the Stomach/SI-sensitivity index's.

TABLE 11

Stomach specific GLP-2 analogues - Hydrophaticity Profile (HPP)

| | Compared to 1559 in % | | | | | | | | | | | | | | | |
|---|---|---|---|---|---|---|---|---|---|---|---|---|---|---|---|---|
| ZP | SI- | Colon- | Stomach- | Sensitivity index | Sensitivity index | Sequence | | | | | HPI | | | | | |
| no. | BW | BW | BW | Si/Co | Stomach/Co | 11 | 16 | 20 | 24 | 28 | 11 | 16 | 20 | 24 | 28 | HPP |
| 2400 | 106 | 106 | 111 | 1.00 | 1.05 | L | L | S | S | S | 3.8 | 3.8 | −0.8 | −0.8 | −0.8 | 5.2 |
| 2412 | 94 | 99 | 106 | 0.95 | 1.07 | L | L | A | A | A | 3.8 | 3.8 | 1.8 | 1.8 | 1.8 | 13 |
| 2396 | 104 | 102 | 117 | 1.02 | 1.16 | F | F | S | S | S | 2.8 | 2.8 | −0.8 | −0.8 | −0.8 | 3.2 |
| 2395 | 98 | 97 | 113 | 1.01 | 1.16 | K | K | K | K | K | −3.9 | −3.9 | −3.9 | −3.9 | −3.9 | −19.5 |
| 2394 | 105 | 96 | 109 | 1.09 | 1.14 | L | L | S | S | S | 3.8 | 3.8 | −0.8 | −0.8 | −0.8 | 5.2 |
| 2401 | 98 | 88 | 107 | 1.11 | 1.22 | F | F | S | S | S | 2.8 | 2.8 | −0.8 | −0.8 | −0.8 | 3.2 |

The data shows that HPI interval for the individual positions 11, 16, 20, 24 and 28 for the stomach specific GLP-2 analogues should independently for the positions 11 and 16 be at least $-3.9 \leq HPI_{11,16} \leq 3.8$ or preferably $2.8 \leq HPI_{11,16} \leq 3.8$ or $HPI_{11,16} = -3.9$ and for positions 20, 24 and 28 the HPI should independently be at least $-3.9 \leq HPI_{20,24,28} \leq 1.8$ or preferably $-0.8 \leq HPI_{20,24,28} \leq 1.8$ or $HPI_{20,24,28} = -3.9$.

Possible amino substitution patterns according to HPI-intervals are shown in table 12.

TABLE 12

| Possible amino substitution patterns Stomach specific GLP-2 analogues | | | | | | |
|---|---|---|---|---|---|---|
| HPI | 11 | 16 | 20 | 24 | 28 | HPP |
| Preferred | L | L | A | A | A | |
| | F | F | S | S | S | |
| | K | K | | K | K | |
| | | | | | | 13-(−16.4) |
| More Preferred | L | L | | | | |
| | F | F | S | S | S | |
| | | | | | | 5.2-3.2 |

Thus, for stomach-specific compounds

X11 may be Leu, Phe or Lys.
X16 may be Leu, Phe or Lys.
X20 may be Ala or Ser.
X24 may be Ala, Ser or Lys.
X28 may be Ala, Ser or Lys.

For example, X11 and X16 may independently be Leu or Phe, and X20, X24 and X28 may be Ser.

Effect of Hydrogen Bonding Potential (HBP) on Receptor Specificity

As mentioned earlier the receptor specificity of the GLP-2 analogues was also found to be governed by the hydrogen bonding potential of the above the positions 11, 16, 20, 24, and 28.

The hydrogen bonding potential (HBP) was introduced and defined for the individual amino acids by W. D. Stein, "The movement of molecules across cell membranes"; Academic Press N.Y. 1967, pp 65-125, and is providing the capability of a given amino acid side-chain to make hydrogen bonds.

HBP for the individual amino acids are given in table 13

TABLE 13

| HBP for the individual amino acids | | |
|---|---|---|
| Amino acid | | HBP |
| Leu | L | 0 |
| Ala | A | 0 |
| Cys | C | 0 |
| Gly | G | 0 |
| Ile | I | 0 |
| Met | M | 0 |
| Phe | F | 0 |
| Pro | P | 0 |
| Val | V | 0 |
| His | H | 1 |
| Trp | W | 1 |
| Lys | K | 2 |
| Ser | S | 2 |
| Thr | T | 2 |
| Tyr | Y | 2 |
| Arg | R | 3 |
| Asn | N | 3 |
| Asp | D | 3 |
| Gln | Q | 3 |
| Glu | E | 3 |

Example 15

Effect of Hydrogen Bonding Potential (HBP) on Stomach Specificity

Examples of stomach specific analogues are shown in table 14.

TABLE 14

Stomach specific GLP-2 peptide analogues

| | Compared to 1559 in % | | | | | | | | | | | | | | |
|---|---|---|---|---|---|---|---|---|---|---|---|---|---|---|---|
| ZP no. | SI-BW | Colon-BW | Stomach-BW | Sensitivity index Si/Co | Sensitivity index Stomach/Co | \multicolumn{5}{c}{Sequence} | \multicolumn{6}{c}{HBP} |
| | | | | | | 11 | 16 | 20 | 24 | 28 | 11 | 16 | 20 | 24 | 28 | ΣHBP |
| 2400 | 106 | 106 | 111 | 1.00 | 1.05 | L | L | S | S | S | 0 | 0 | 2 | 2 | 2 | 6 |
| 2412 | 94 | 99 | 106 | 0.95 | 1.07 | L | L | A | A | A | 0 | 0 | 0 | 0 | 0 | 0 |
| 2396 | 104 | 102 | 117 | 1.02 | 1.15 | F | F | S | S | S | 0 | 0 | 2 | 2 | 2 | 6 |
| 2395 | 98 | 97 | 113 | 1.01 | 1.16 | K | K | K | K | K | 2 | 2 | 2 | 2 | 2 | 10 |
| 2394 | 105 | 96 | 109 | 1.09 | 1.14 | L | L | S | S | S | 0 | 0 | 2 | 2 | 2 | 6 |
| 2401 | 98 | 88 | 107 | 1.11 | 1.22 | F | F | S | S | S | 0 | 0 | 2 | 2 | 2 | 6 |
| | | | | | | | | | | | 0-2 | 0-2 | 0-2 | 0-2 | 0-2 | 0-10 |

According to the table the HBP intervals for the individual positions 11, 16, 20, 24 and 28 for the stomach specific GLP-2 analogues should independently for all the positions be at least $0 \leq HBP_{11,16,20,24,28} \leq 2$. In accordance with the HBP intervals, possible amino acid substitution patterns are shown in table 15.

TABLE 15

Possible amino acid substitution patterns
Stomach specific GLP-2 analogues

| HBP | 11 | 16 | 20 | 24 | 28 |
|---|---|---|---|---|---|
| Preferred | L | L | A | A | A |
| | F | F | S | S | S |
| | K | K | | K | K |
| HBP | 0-2 | 0-2 | 0-2 | 0-2 | 0-2 |
| More | L | L | | K | K |
| Preferred | F | F | S | S | S |
| HBP | 0 | 0 | 2 | 2 | 2 |
| Most | L | L | S | S | S |

TABLE 15-continued

Possible amino acid substitution patterns
Stomach specific GLP-2 analogues

| preferred | F | F | | | |
|---|---|---|---|---|---|
| HBP | 0 | 0 | 2 | 2 | 2 |

Preferred stomach specific analogues are GLP-2 analogues with HBP intervals for the positions 11 and 16 of $HBP_{11,16} = 0$ and for the positions 20, 24, and 28 of independently $0 \leq HBP_{20,24,28} \leq 2$.
Certain stomach specific GLP-2 analogues are as follows:
X11 may be Leu, Phe or Lys.
X16 may be Leu, Phe or Lys.
X20 may be Ala or Ser.
X24 may be Ala, Ser or Lys.
X28 may be Ala, Ser or Lys.

For example, X11 and X16 may independently be Leu or Phe, X24 and X28 may independently be Lys or Ser, and X20 may be Ser.

For example, X11 and X16 may independently be Leu or Phe, and X20, X24 and X28 may be Ser.

Example 16

Effect of Hydrogen Bonding Potential (HBP) on Small Intestine Specificity

Small intestine specific GLP-2 analogues was also found to be governed by the parameters such as the hydrogen bonding potential of the above particular mentioned positions 11, 16, 20, 24, and 28. HBP for the individual amino acids are given in table 16.

TABLE 16

Effect of hydrogen bonding potential (HBP) on small intestine specificity

| | Compared to 1559 in % | | | | | | | | | | | | | | | |
|---|---|---|---|---|---|---|---|---|---|---|---|---|---|---|---|---|
| ZP no. | SI-BW | Colon-BW | Sto-BW | Sensitivity index Si/Co | Sensitivity index Stomach/Co | \multicolumn{5}{c}{Sequence} | \multicolumn{6}{c}{HBP} |
| | | | | | | 11 | 16 | 20 | 24 | 28 | 11 | 16 | 20 | 24 | 28 | ΣHBP |
| 2242 | 111.7 | 106.6 | 99.6 | 1.05 | 0.93 | S | A | R | A | A | 2 | 0 | 3 | 0 | 0 | 5 |
| 2411 | 117 | 111 | 106 | 1.05 | 0.95 | A | A | A | S | A | 0 | 0 | 0 | 2 | 0 | 2 |
| 2380 | 108 | 102 | 98 | 1.06 | 0.96 | S | S | S | S | S | 2 | 2 | 2 | 2 | 2 | 10 |
| 2384 | 128 | 118 | 100 | 1.08 | 0.85 | A | A | A | A | S | 0 | 0 | 0 | 0 | 2 | 2 |

TABLE 16-continued

Effect of hydrogen bonding potential (HBP) on small intestine specificity

Compared to 1559 in %

| ZP no. | SI-BW | Colon-BW | Sto-BW | Sensitivity index Si/Co | Sensitivity index Stomach/Co | Sequence 11 | 16 | 20 | 24 | 28 | HBP 11 | 16 | 20 | 24 | 28 | ΣHBP |
|---|---|---|---|---|---|---|---|---|---|---|---|---|---|---|---|---|
| 2268 | 123.6 | 112.5 | 87.4 | 1.10 | 0.78 | A | A | S | S | S | 0 | 0 | 2 | 2 | 2 | 6 |
| 2398 | 108 | 97 | 102 | 1.11 | 1.05 | S | A | S | S | S | 2 | 0 | 2 | 2 | 2 | 8 |
| 2420 | 112 | 101 | 90 | 1.11 | 0.89 | S | A | A | A | A | 2 | 0 | 0 | 0 | 0 | 2 |
| 2417 | 119 | 106 | 90 | 1.12 | 0.85 | A | A | S | A | A | 0 | 0 | 2 | 0 | 0 | 2 |
| 2272 | 118.1 | 104.7 | 96 | 1.13 | 0.92 | A | S | A | S | A | 0 | 2 | 0 | 2 | 0 | 4 |
| 2423 | 123 | 109 | 94 | 1.13 | 0.86 | A | A | S | A | A | 0 | 0 | 2 | 0 | 0 | 2 |
| 2264 | 125.7 | 109.5 | 87 | 1.15 | 0.79 | A | A | A | A | A | 0 | 0 | 0 | 0 | 0 | 0 |
| 2385 | 110 | 95 | 93 | 1.16 | 0.98 | S | A | S | S | S | 2 | 0 | 2 | 2 | 2 | 8 |
| 2399 | 119 | 103 | 115 | 1.16 | 1.12 | A | S | S | S | S | 0 | 2 | 2 | 2 | 2 | 8 |
| 2418 | 117 | 100 | 91 | 1.17 | 0.91 | A | A | A | S | A | 0 | 0 | 0 | 2 | 0 | 2 |
| 2381 | 123 | 104 | 92 | 1.18 | 0.88 | A | A | S | S | S | 0 | 0 | 2 | 2 | 2 | 6 |
| 2397 | 122 | 101 | 109 | 1.21 | 1.08 | A | A | A | A | S | 0 | 0 | 0 | 0 | 2 | 2 |
| | | | | | | | | | | | 0-2 | 0-2 | 0-3 | 0-2 | 0-2 | 0-11 |

According to the table the HBP intervals for the individual positions 11, 16, 20, 24 and 28 for the small intestine specific GLP-2 analogues should independently for all the positions be at least $0 \leq HBP_{11,16,20,24,28} \leq 2$.

Preferred analogues have the HBP interval for position 11 and 16 $HBP_{11,16}=0$ and the positions 20, 24, and 28 have independently the HBP interval of $0 \leq HBP_{20,24,28} \leq 2$.

More preferred GLP-2 analogues showing small intestine specificity are peptides with an HBP interval for position 11 and 16 of $HBP_{11,16}=0$, $HBP_{20}=0-2$, and $HBP_{24,28}=2$.

Certain substitution patterns are thus shown in Table 17.

TABLE 17

Small intestine specificity peptides
Small intestine specific GLP-2 analogues

| HBP | 11 | 16 | 20 | 24 | 28 |
|---|---|---|---|---|---|
| preferred | A | A | A | A | A |
| | S | S | S | S | S |
| | G | G | G | G | G |
| | T | T | T | T | T |
| HBP | 0-2 | 0-2 | 0-2 | 0-2 | 0-2 |
| more preferred | A | A | A | A | A |
| | S | S | S | S | S |
| | | | G | G | G |
| | | | T | T | T |

TABLE 17-continued

Small intestine specificity peptides
Small intestine specific GLP-2 analogues

| HBP | 0-2 | 0-2 | 0-2 | 0-2 | 0-2 |
|---|---|---|---|---|---|
| most preferred | A | A | A | A | A |
| | S | S | S | S | S |
| | | | G | G | G |
| | | | T | T | T |
| HBP | 0 | 0 | 0-2 | 0-2 | 0-2 |

Thus, in small intestine-selective compounds, each of X11, X16, X20, X24 and X28 may independently be Ala, Ser, Gly or Thr. For example, each of X11 and X16 may independently be Ala or Ser, and X20, X24 and X28 may independently be Ala, Ser, Gly or Thr. For example, X11 and X16 may both be Ala, and X20, X24 and X28 may independently be Ala, Ser, Gly or Thr.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

The invention claimed is:

1. A glucagon-like peptide 2 (GLP-2) analogue represented by the general Formula I:

$R^1$-$Z^1$-His-X2-X3-Gly-X5-X6-X7-X8-X9-X10-X11-X12-X13-X14-X15-X16-X17-X18-X19-X20-X21-Phe-Ile-X24-Trp-Leu-Ile-X28-Thr-Lys-X31-X32-X33-$Z^2$-$R^2$    (SEQ ID NO:2)

wherein:
$R^1$ is hydrogen, $C_{1-4}$ alkyl, methyl, acetyl, formyl, benzoyl or trifluoroacetyl;
X2 is Gly, Ala or Sar;
X3 is Glu or Asp;
X5 is Ser or Thr;
X6 is Phe or Pro or a conservative substitution;
X7 is Ser or Thr;
X8 is Asp or Ser or a conservative substitution;
X9 is Glu or Asp or a conservative substitution;
X10 is Met, Leu, Nle or an oxidatively stable Met-replacement amino acid;
X11 is Y1;
X12 is Thr or Lys or a conservative substitution;
X13 is Ile, Glu or Gln or a conservative substitutio;
X14 is Leu, Met or Nle or a conservative substitution;
X15 is Asp or Glu;
X16 is Y2;
X17 is Leu or Glu or a conservative substitution;
X18 is Ala or Aib or a non-conservative substitution;
X19 is Ala or Thr or a conservative substitution;
X20 is Y3;
X21 is Asp or Ile or a conservative substitution;
X24 is Y4;
X28 is Y5;
X31 is Pro, Ile or deleted;
X32 is Thr or deleted;
X33 is Asp, Asn or deleted;
$R^2$ is $NH_2$ or OH;
wherein
$Z^1$ and $Z^2$ are independently absent or a peptide sequence of 1-10 amino acid units selected from the group consisting of Ala, Leu, Ser, Thr, Tyr, Asn, Gln, Asp, Glu, Lys, Arg, His, Met and Orn; and
the hydrophaticity profile (HPP) of the residues X11, X16, X20, X24, X28 of formula I calculated as $$HPP=\Sigma hpi_{X11}+hpi_{X16}+hpi_{X20}+hpi_{X24}+hpi_{X28} \text{ is } \geq -10$$

wherein
$Y_1$, $Y_2$, $Y_4$, and $Y_5$ can individually be selected from the group consisting of Asn, Asp, Glu, Gln, Lys, His, Arg, Ala, Ser, Thr, Pro, Gly, Leu, Ile, Val, Met or Phe; and
$Y_3$ can be selected from the group consisting of Asn, Asp, Glu, Gln, His, Arg, Ala, Ser, Thr, Pro, Gly, Leu, Ile, Val, Met or Phe;
with the proviso that when X20 is Arg then X11 is Ser, X16 is Ala, X24 is Ala, X28 is Ala and Z2 is Lys, or a pharmaceutically acceptable salt thereof and with the proviso that if X15 is Asp then X8 is Ser.

2. A glucagon-like peptide 2 (GLP-2) analogue according to claim 1 wherein HPP is $\geq -4$.

3. A glucagon-like peptide 2 (GLP-2) analogue according to claim 1 wherein HPP$\geq 0$.

4. The GLP-2 analogue of claim 1, wherein said substitution at position X10 is Leu, Nle, or an oxidatively stable Met-replacement amino acid, such as Met(O) or Met(O)$_2$.

5. The GLP-2 analog of claim 1 which is:
 (i) 2263-HGEGSFSDELSTILESLAASDFISWL-ISTKITD-NH2 (SEQ ID NO: 7),
 (ii) 2264-HGEGSFSDELATILEALAAADFIAWLI-ATKITD-NH2 (SEQ ID NO:8),
 (iii) 2266-HGEGSFSDELETILEELAAEDFIEWLI-ETKITD-NH2 (SEQ ID NO:9),
 (iv) 2267-HGEGSFSDELSTILESLAAADFIAWLI-ATKITD-NH2 (SEQ ID NO:10),
 (v) 2268-HGEGSFSDELATILEALAASDFISWL-ISTKITD-NH2 (SEQ ID NO:11),
 (vi) 2269-HGEGSFSDELKTILESLAAAD-FIEWLIQTKITD-NH2 (SEQ ID NO:12),
 (vii) 2270-HGEGSFSDELNTILESLAASDFISWL-ISTKITD-NH2 (SEQ ID NO:13),
 (viii) 2272-HGEGSFSDELATILESLAAADFISWLI-ATKITD-NH2 (SEQ ID NO:14), or
 (ix) 2242-HGEGSFSSELSTILDALAARDFIAWLI-ATKITDK-OH (SEQ ID NO:15).

6. The GLP-2 analogue of claim 1 which is:
2264 HGEGSFSDELATILEALAAADFIAWLIATKITD-NH$_2$ (SEQ ID NO:8).

* * * * *

UNITED STATES PATENT AND TRADEMARK OFFICE
CERTIFICATE OF CORRECTION

PATENT NO. : 8,642,727 B2
APPLICATION NO. : 12/514042
DATED : February 4, 2014
INVENTOR(S) : Bjarne Due Larsen et al.

It is certified that error appears in the above-identified patent and that said Letters Patent is hereby corrected as shown below:

Claims

Column 139, Claim 1, Line 57, replace "substitutio" with --substitution--;

Line 64, replace "is Y3" with --is Y3;--.

Column 140, Claim 1, Line 45, replace "hydrophaticity" to --hydropathicity--;

Line 58, replace "Z2" with --$Z^2$--.

Column 141, Claim 5, Line 1, replace "analog" with --analogue--;

Line 3, replace "NH2" with --$NH_2$--;

Line 5, replace "NH2" with --$NH_2$--;

Line 7, replace "NH2" with --$NH_2$--;

Line 9, replace "NH2" with --$NH_2$--;

Line 11, replace "NH2" with --$NH_2$--;

Line 13, replace "NH2" with --$NH_2$--;

Line 15, replace "NH2" with --$NH_2$--;

Line 17, replace "NH2" with --$NH_2$--.

Signed and Sealed this
Sixth Day of October, 2015

Michelle K. Lee
*Director of the United States Patent and Trademark Office*